US011339204B2

(12) United States Patent
McKinnon et al.

(10) Patent No.: US 11,339,204 B2
(45) Date of Patent: May 24, 2022

(54) TRUNCATED VWF

(71) Applicant: Imperial College Innovations Ltd, London (GB)

(72) Inventors: Thomas McKinnon, London (GB); Mike Laffan, London (GB)

(73) Assignee: Imperial College Innovations Ltd., London (GB)

( * ) Notice: Subject to any disclaimer, the term of this patent is extended or adjusted under 35 U.S.C. 154(b) by 0 days.

(21) Appl. No.: 16/610,701

(22) PCT Filed: May 4, 2018

(86) PCT No.: PCT/GB2018/051212
§ 371 (c)(1),
(2) Date: Nov. 4, 2019

(87) PCT Pub. No.: WO2018/203086
PCT Pub. Date: Nov. 8, 2018

(65) Prior Publication Data
US 2020/0157186 A1 May 21, 2020

(30) Foreign Application Priority Data
May 4, 2017 (GB) .................................. 1707139

(51) Int. Cl.
*C07K 14/755* (2006.01)
*A61K 38/095* (2019.01)
*A61P 7/04* (2006.01)
*A61K 31/196* (2006.01)
*A61K 45/06* (2006.01)

(52) U.S. Cl.
CPC .......... *C07K 14/755* (2013.01); *A61K 31/196* (2013.01); *A61K 38/095* (2019.01); *A61P 7/04* (2018.01); *A61K 45/06* (2013.01)

(58) Field of Classification Search
CPC ........ C07K 14/755; A61K 38/095; A61P 7/04
See application file for complete search history.

(56) References Cited

U.S. PATENT DOCUMENTS

| 2012/0289468 A1* | 11/2012 | Barnett ...................... A61P 7/04 514/14.1 |
| 2015/0005473 A1 | 1/2015 | Choi et al. |
| 2015/0266943 A1* | 9/2015 | Chhabra ................ A61K 38/37 514/14.1 |

FOREIGN PATENT DOCUMENTS

| WO | 91/13093 | 9/1991 |
| WO | 2011/060242 | 5/2011 |
| WO | WO 2011/060242 | * 5/2011 |
| WO | 2015/106052 | 7/2015 |

OTHER PUBLICATIONS

Zhou et al., 2012, Sequence and structure relationships within von Willebrand factor, Blood, 120(2): 449-458.*
Bonthron et al., 1986, Nucleotide sequence of pre-pro-von Willebrand factor cDNA, Nucleic Acids Research, 14(17): 7125-7127.*
Karlin, S. et al. "Methods for assessing the statistical significance of molecular sequence features by using general scoring schemes", Proc. Natl. Acad. Sci. USA, vol. 87, Mar. 1990, pp. 2264-2268.
Pearson, W. R. et al. "Improved tools for biological sequence comparison", Proc. Natl. Acad. Sci. USA, vol. 85, Apr. 1988.
Devereux, John et al. "A comprehensive set of sequence analysis programs for the VAX", Nucleic Acid Research, vol. 12, No. 1, 1984, pp. 387-395.
Karlin, S. et al. "Applications and statistics for multiple high-scoring segments in molecular sequences", Proc. Natl. Acad. Sci. USA, vol. 90, Jun. 1993, pp. 5873-5877.
Torelli, A. et al., "ADVANCE and ADAM: two algorithms for the analysis of global similarity between homologous nformational sequences", Cabios, vol. 10, No. 1, 1994, pp. 3-5.
Myers, Eugene W. et al., "Optimal alignments in linear space", Cabios, vol. 4, No. 1, 1998, pp. 11-17.
International Search Report and Written Opinion dated Jun. 26, 2018, from International Application No. PCT/GB2018/051212, 17 pages.
Hommais, A. et al. "Impaired dimerization of von Willebrand factor subunit due to mutation A280ID in the CK domain Yesults in a recessive type 2A subtype 11D von Willebrand disease", Thromb Haemost 2006; 95: 776-81.
South, K. et al. "A model for the conformational activation of the structurally quiescent metalloprotease ADAMTS13 by von Willebrand factor", The Journal of Biological Chemistry, vol. 292, No. 14, pp. 5760-5769, 2017.
Combined Search and Examination Report under Sections 17 and 18(3) dated Feb. 7, 2018, from GB Application No. 1707139.0, 7 pages.
Breevoort, D. et al. "Proteomic Screen Identifies IGFBP7 as a Novel Component of Endothelial Cell-Specific Neibel-Palade Bodies", Journal of Proteome, 2012, pp. 2925-2936.
Voorberg, J. et al. "Biogenesis of Von Willebrand factor-containing organelles in heterologous transfected CV-1 cells", The EMBO Journal, vol. 12, No. 2, pp. 749-758, 1993.
Lenting, P. et al. "An Experimental Model to Study the in Vivo Survival of von Willebrand Factor", The Journal of Biological Chemistry, vol. 279, No. 13, pp. 12102-12109, 2004.
Ulrichts, H. et al. "Shielding of the A1 Domain by the D'D3 Domains of von Willebrand Factor Modulates Its nteraction with Platelet Glycoprotein Ib-IX-V", The Journal of Biological Chemistry, vol. 281, No. 8, pp. 4699-4707, 2006.
Shapiro, S. E., et al. "The von Willebrand factor predicted unpaired cysteines are essential for secretion." Journal of Thrombosis and Haemostasis 12.2 (Feb. 2014): 246-254.

(Continued)

*Primary Examiner* — Amber D Steele
(74) *Attorney, Agent, or Firm* — Meunier Carlin & Curfman LLC

(57) ABSTRACT

The present invention relates to novel truncated fragments of von Willebrand factor (VWF) and the use of such fragments and nucleic acids encoding such fragments in the treatment of von Willebrand disease (VWD) and haemophilia.

19 Claims, 4 Drawing Sheets
Specification includes a Sequence Listing.

(56) References Cited

OTHER PUBLICATIONS

Altschul, Stephen F., et al. "Gapped BLAST and PSI-BLAST: a new generation of protein database search programs." Nucleic acids research 25 17 (1997): 3389-3402.

* cited by examiner

Flow chamber coated with VWF – platelet capture direct to VWF

VWF perfused over collagen surface, $1500s^{-1}$

TRUNCATED VWF

FIELD OF THE INVENTION

The present invention relates to novel truncated fragments of von Willebrand factor (VWF) and the use of such fragments and nucleic acids encoding such fragments in the treatment of von Willebrand disease (VWD) and haemophilia.

BACKGROUND TO THE INVENTION

Von Willebrand Factor (VWF) is a large multimeric plasma glycoprotein that performs two essential roles in haemostasis. Firstly, VWF mediates platelet adhesion to sites of vessel injury under high shear stress and secondly, VWF is the carrier molecule of coagulation factor VIII (FVIII), prolonging its otherwise short half-life. FIG. 1 shows the domain organisation of the VWF molecule with various functional sites. Upon vessel injury VWF binds to the exposed sub endothelial matrix proteins; principally collagen via its A3 domain. This invokes a conformational change in the VWF molecule exposing the binding site in the A1 domain for glycoprotein Ib (GPIb) expressed on the surface of platelets. The FVIII binding site is located in the D'D3 domain and is essential for stabilising and prolonging the half-life of FVIII within the circulation. The present inventors have previously (Shapiro et al., Journal of Thrombosis and Haemostasis, 12: 246-254, 2014) determined that the cysteine residues that have been found to be free in a proportion of VWF monomers are essential for the normal synthesis and secretion of VWF. They also concluded that the C domains of VWF must be intact for normal synthesis and secretion of VWF.

Deficiency of VWF results in the bleeding disorder von Willebrand disease, which is the most common inherited bleeding disorder, affecting ~3-4 individuals in every 100,000 representing 1.3% of the population. Treatment of VWD is usually performed with either desmopressin to promote release of VWF or with replacement therapy involving the administration of VWF concentrates, at a cost to the NHS of approximately £10 million per year in drug alone.

Haemophilia is a mostly inherited bleeding disorder, which affects a patient's ability to form blood clots. Haemophilia A is caused by a lack of factor VIII and haemophilia B is caused by a lack of factor IX. Within haemophilia, the use of recombinant factor VIII for the treatment of Haemophilia A has required the co-delivery of full length VWF in order to stabilise the delivered FVIII. However, the half-life of FVIII is still an issue and prolongation of FVIII survival in plasma would have clear benefits for patients by reducing frequency of injection, elevating trough levels and providing better, more continuous protection from bleeding at reduced cost and inconvenience. Additionally, introduction of full length recombinant VWF into haemophiliacs who express native VWF can lead to complications including excessive clotting. Several recent attempts to circumvent the use of co-delivery of VWF using modified FVIII molecules have been reported recently but the results are universally disappointing.

There is therefore a need in the art for new treatments for VWF and haemophilia.

SUMMARY OF THE INVENTION

The present inventors have produced a novel truncated VWF variant in which the D4-C6 domains are deleted, and have surprisingly found that this variant shares the function of the full length protein. In particular, it demonstrates normal multimer formation and is able to interact with collagen under static conditions. Significantly, the ability of the variant to capture platelets under shear stress is not altered. The variant can therefore be used in place of the full length protein in the treatment of VWD or haemophilia.

Accordingly, in a first aspect the present invention provides a von Willebrand factor (VWF) polypeptide lacking the D4-C6 domains of the full length VWF protein, or a polypeptide having at least 70% sequence identity thereto.

DETAILED DESCRIPTION OF THE INVENTION

The present inventors have been investigating the functional role of the C-terminal domains of VWF (taken as D4-C6, i.e. D4, C1, C2, C3, C4, C5 and C6), since it is not fully understood how this region of the molecule mediates function. As part of this work a novel truncated VWF variant was designed, deleting the D4-C6 domains (residues 1875-2720). The removal of this region, which comprises 845 amino acids (2535 base pairs), reduces the size of VWF to 1968 amino acids (5904 base pairs). The final VWF construct termed VWF deletion D4C6 (VWF-ΔD4C6) is therefore comprised of residues 1-1874 (corresponding to the signal peptide and D1-D2-D'D3-A1-A2-A3 domains) and 2721-2813 (corresponding to the CK domain). FIG. 1 shows the domain structure of full length VWF, and FIG. 2 shows the domain structure of VWF-ΔD4C6. The amino acid and nucleotide sequence of full length human VWF are shown in SEQ ID NO: 1 and SEQ ID NO: 2 respectively. The amino acid sequence and cDNA sequence of VWF-ΔD4C6 are shown in SEQ ID NO: 3 and SEQ ID NO: 4 respectively. Amino acid residues 1-1874 of SEQ ID NO: 3 correspond to the signal peptide and D1-D2-D'D3-A1-A2-A3 domains and amino acid residues 1875 to 1967 of SEQ ID NO: 3 correspond to the CK domain. The individual domain sequences of VWF-ΔD4C6 are given later in this specification and are identified as SEQ ID NO: 23 to 31. The polypeptide of the invention is not naturally-occurring as it lacks the D4-C6 domains of the human VWF protein.

Accordingly, in a first aspect the present invention provides a von Willebrand factor (VWF) polypeptide lacking the D4-C6 domains of the full length VWF protein, or a polypeptide having at least 70% sequence identity thereto. The D4-C6 domains correspond to amino acid residues 1875-2720 of the full length VWF protein (SEQ ID NO: 1). The polypeptide of the first aspect of the invention may therefore lack amino acid residues 1875-2720 of the full length VWF protein (SEQ ID NO: 1). The amino acid sequence of VWF-ΔD4C6 is shown in SEQ ID NO: 3, and corresponds to amino acid residues 1-1874 and 2721-2813 of SEQ ID NO: 1. The polypeptide of the first aspect of the invention may therefore comprise the amino acid sequence of SEQ ID NO: 3, i.e. comprise the signal peptide and the following domains: D1-D2-D'D3-A1-A2-A3-CK. The polypeptide of the first aspect of the invention may consist of the amino acid sequence of SEQ ID NO: 3, i.e. consist of the signal peptide and the following domains: D1-D2-D'D3-A1-A2-A3-CK. The signal peptide is typically present.

The term "comprise" as used herein takes its usual meaning, and means that the claim encompasses all the listed elements or method steps, but may also include additional, unnamed elements or method steps. The polypeptide may comprise or consist of any of the amino acid sequences disclosed herein.

A "peptide" as used herein refers to a chain of amino acid residues linked by peptide bonds. A peptide is usually defined as molecules that consist of between 2 and 50 amino acids. A "polypeptide" is also a chain of amino acid residues linked by peptide bonds. However, a polypeptide is longer than a peptide. A polypeptide is usually defined as a molecule that consists of more than 50 amino acids. In contrast to peptides, polypeptides can adopt complex secondary, tertiary and quaternary structures. A "von Willebrand factor (VWF) polypeptide" as used herein refers to a polypeptide derived from the full length VWF protein. The polypeptide of the first aspect of the invention lacks the D4-C6 domains of the full length VWF protein, but typically retains the other domains of the full length VWF protein, i.e. the D1-D2-D'D3-A1-A2-A3 and CK domains.

Throughout this specification, amino acids may be referred to using the three letter and one letter codes as follows: glycine (G or Gly), alanine (A or Ala), valine (V or Val), leucine (L or Leu), isoleucine (I or Ile), proline (P or Pro), phenylalanine (F or Phe), tyrosine (Y or Tyr), tryptophan (W or Trp), lysine (K or Lys), arginine (R or Arg), histidine (H or His), aspartic acid (D or Asp), glutamic acid (E or Glu), asparagine (N or Asn), glutamine (Q or Gln), cysteine (C or Cys), methionine (M or Met), serine (S or Ser) and Threonine (T or Thr). Where a residue may be aspartic acid or asparagine, the symbols Asx or B may be used. Where a residue may be glutamic acid or glutamine, the symbols Glx or Z may be used. References to aspartic acid include aspartate, and references to glutamic acid include glutamate, unless the context specifies otherwise.

The polypeptide of the first aspect of the invention may have at least 70% identity, at the amino acid level, to the amino acid sequence of any of the polypeptides disclosed herein, for example a polypeptide lacking amino acid residues 1875-2720 of SEQ ID NO: 1, a polypeptide comprising or consisting of the amino acid sequence of SEQ ID NO: 3 or a polypeptide comprising or consisting of amino acid residues 1-1874 and 2721-2813 of SEQ ID NO: 1. Typically, the polypeptide has at least 75%, 80%, 85%, 90%, 91%, 92%, 93%, 94%, for example at least 95%, 96%, 97%, 98% or 99% identity, at the amino acid level, to any of the amino acid sequences disclosed herein.

The present inventors have found that VWF-ΔD4C6 having the domain structure D1-D2-D'D3-A1-A2-A3-CK is the minimal VWF molecule possible, and so typically no other domains of the full length VWF are missing from the polypeptide of the first aspect of the invention. However, parts of each of the domains of VWF-ΔD4C6 may be removed, as long as the polypeptide of the invention retains at least 70% identity to a polypeptide as defined herein, for example one having the sequence of SEQ ID NO: 3. For example, 1, 2, 3, 4, 5, 6, 7, 8, 9 or 10 amino acids may be removed from any one or more of the amino acid sequences of the D1D2, D', D3, A1, A2, A3 and/or CK domains having the sequences of SEQ ID Nos: 24, 25, 26, 27, 29, 30 and 31 respectively, as long as the polypeptide retains at least 70% identity to a polypeptide as defined herein.

"Identity" as known in the art is the relationship between two or more polypeptide sequences or two or more polynucleotide sequences, as determined by comparing the sequences. In the art, identity also means the degree of sequence relatedness between polypeptide or polynucleotide sequences, as the case may be, as determined by the match between strings of such sequences. While there exist a number of methods to measure identity between two polypeptide or two polynucleotide sequences, methods commonly employed to determine identity are codified in computer programs. Preferred computer programs to determine identity between two sequences include, but are not limited to, GCG program package (Devereux, et al., Nucleic Acids Research, 12, 387 (1984), BLASTP, BLASTN, and FASTA (Atschul et al., J. Molec. Biol. 215, 403 (1990)).

One can use a program such as the CLUSTAL program to compare amino acid sequences. This program compares amino acid sequences and finds the optimal alignment by inserting spaces in either sequence as appropriate. It is possible to calculate amino acid identity or similarity (identity plus conservation of amino acid type) for an optimal alignment. A program like BLASTx will align the longest stretch of similar sequences and assign a value to the fit. It is thus possible to obtain a comparison where several regions of similarity are found, each having a different score. Both types of identity analysis are contemplated in the present invention.

The percent identity of two amino acid sequences or of two nucleic acid sequences is determined by aligning the sequences for optimal comparison purposes (e.g., gaps can be introduced in the first sequence for best alignment with the sequence) and comparing the amino acid residues or nucleotides at corresponding positions. The "best alignment" is an alignment of two sequences which results in the highest percent identity. The percent identity is determined by the number of identical amino acid residues or nucleotides in the sequences being compared (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul (1990) Proc. Natl. Acad. Sci. USA 87:2264-2268, modified as in Karlin and Altschul (1993) Proc. Natl. Acad. Sci. USA 90:5873-5877. The NBLAST and XBLAST programs of Altschul, et al. (1990) J. Mol. Biol. 215:403-410 have incorporated such an algorithm. BLAST nucleotide searches can be performed with the NBLAST program, score=100, wordlength=12 to obtain nucleotide sequences homologous to nucleic acid molecules. BLAST protein searches can be performed with the XBLAST program, score=50, wordlength=3 to obtain amino acid sequences homologous to protein molecules for use in the invention. To obtain gapped alignments for comparison purposes, Gapped BLAST can be utilised as described in Altschul et al. (1997) Nucleic Acids Res. 25:3389-3402. Alternatively, PSI-Blast can be used to perform an iterated search which detects distant relationships between molecules (Id.). When utilising BLAST, Gapped BLAST, and PSI-Blast programs, the default parameters of the respective programs (e.g., XBLAST and NBLAST) can be used. Another example of a mathematical algorithm utilised for the comparison of sequences is the algorithm of Myers and Miller, CABIOS (1989). The ALIGN program (version 2.0) which is part of the CGC sequence alignment software package has incorporated such an algorithm. Other algorithms for sequence analysis known in the art include ADVANCE and ADAM as described in Torellis and Robotti (1994) Comput. Appl. Biosci., 10:3-5; and FASTA described in Pearson and Lipman (1988) Proc. Natl. Acad. Sci. 85:2444-8. Within FASTA, ktup is a control option that sets the sensitivity and speed of the search.

Polypeptides for use in the invention may have an amino acid sequence that is identical to one or more of the amino acid sequences disclosed herein apart from the substitution of one or more amino acids with one or more other amino acids. The skilled person is aware that various amino acids have similar properties, based on the nature of their side chains. One or more such amino acids of a protein, polypeptide or peptide can often be substituted by one or more other such amino acids without eliminating a desired activity of that protein, polypeptide or peptide.

Thus the amino acids glycine, alanine, valine, leucine and isoleucine can often be substituted for one another (amino acids having aliphatic side chains). Of these possible substitutions it is preferred that glycine and alanine are used to substitute for one another (since they have relatively short side chains) and that valine, leucine and isoleucine are used to substitute for one another (since they have larger aliphatic side chains which are hydrophobic). Other amino acids which can often be substituted for one another include: phenylalanine, tyrosine and tryptophan (amino acids having aromatic side chains); lysine, arginine and histidine (amino acids having basic side chains); aspartate and glutamate (amino acids having acidic side chains); asparagine and glutamine (amino acids having amide side chains); and cysteine and methionine (amino acids having sulphur containing side chains).

Substitutions of this nature are often referred to as "conservative" or "semi-conservative" amino acid substitutions. The present invention therefore extends to use of a polypeptide comprising an amino acid sequence described above but with one or more conservative substitutions in the sequence, such that the amino acid sequence has at least 70% identity, more typically at least 75%, 80%, 85%, 90%, 91%, 92%, 93%, 94%, for example at least 95%, 96%, 97%, 98% or 99% identity to those described herein.

It should be appreciated that amino acid substitutions or insertions to the sequences disclosed herein that are within the scope of the present invention can be made using naturally occurring or non-naturally occurring amino acids. For example, D-amino acids can be incorporated in the polypeptides of the invention. Derivatives of amino acids, such as methylated amino acids, may also be used.

Modifications to the amino acid sequence of the polypeptide of the first aspect of the invention may be made using any suitable technique, such as site-directed mutagenesis of the encoding DNA sequence or solid state synthesis.

The polypeptide of the first aspect of the invention may be isolated. "Isolated" refers to material removed from its original environment. The original environment could be a natural environment for example inside a cell.

The polypeptide of the first aspect of the invention may be purified. A "purified polypeptide" as used herein refers to a polypeptide which is at least 20% pure, typically at least 40% pure, more typically at least 50% pure, at least 60% pure, at least 70% pure, at least 80% pure, at least 90% pure, at least 95% pure, or at least 98% pure, as determined by SDS-PAGE.

The polypeptide of the first aspect of the invention may be fused to a heterologous peptide, polypeptide or protein. A "heterologous peptide, polypeptide or protein" as used herein refers to a peptide, polypeptide or protein that imparts desired characteristics to the polypeptide of the invention, for example increased stability, enhanced transport or simplified purification or detection. The heterologous peptide, polypeptide or protein is typically not VWF or derived from VWF.

For example, additional amino acid sequences may be incorporated at either the C- or the N-terminus of the sequence of the polypeptide of the first aspect of the invention, for example a polypeptide having the amino acid sequence of SEQ ID NO: 3, such that a fusion protein is produced with a heterologous polypeptide at one end of the polypeptide of the first aspect of the invention. Alternatively, additional sequences may be incorporated in the middle of the sequence of the polypeptide of the first aspect of the invention, for example a polypeptide having the amino acid sequence of SEQ ID NO: 3. For example, additional sequences may be incorporated between the sections of the sequence of SEQ ID NO: 3 which correspond to the D1-D2-D'D3-A1-A2-A3 (amino acid residues 1 to 1874) and CK domain (amino acid residues 1875 to 1967) respectively, such that amino acid residues 1 to 1874 and 1875 to 1967 of SEQ ID NO: 3 are non-contiguous. In this aspect, it is envisaged that any additional sequences would be short, so as not to interfere with the folding of the polypeptide.

Examples of heterologous peptides, polypeptides and proteins for use in the present invention include glutathione S-transferase, polyhistidine or myc tags to facilitate purification of the polypeptide, for example by affinity chromatography. Alternatively, the heterologous peptide, polypeptide or protein may be a fluorescent polypeptide, which enables detection of the polypeptide of the invention. Fluorescent polypeptides include but are not limited to green fluorescent protein, red fluorescent protein, yellow fluorescent protein, cyan fluorescent protein and their derivatives. Such tags for purification or detection are typically added to the C-terminus of the polypeptide of the invention.

Polypeptides of the invention may be modified to improve their characteristics such as their half-life, for example by the addition of polyethylene glycol (PEGylation), FC or albumin. Any such modifications are typically made either between the A3 and CK domain (between amino acid residues 1874 and 1875 of SEQ ID NO: 3) or at the C-terminus of the polypeptide of the invention Polypeptides of the invention may be produced by recombinant means, for example by expression of a nucleic acid as disclosed herein in a suitable vector, or by solid phase synthesis.

In a second aspect, the present invention provides a nucleic acid comprising a nucleotide sequence encoding a polypeptide according to the first aspect of the invention. The nucleotide sequence may lack nucleotides 5623 to 8160 of SEQ ID NO: 2. The nucleic acid may comprise or consist of the cDNA sequence of SEQ ID NO: 4, or a sequence having at least 70% identity thereto. The nucleic acid may comprise or consist of nucleotides 1 to 5622 and 8161 to 8442 of SEQ ID NO: 2. The nucleic acid of the second aspect of the invention may have at least 70% identity, at the nucleotide level, to any of the nucleotide sequences disclosed herein Typically, the nucleic acid has at least 75%, 80%, 85%, 90%, 91%, 92%, 93%, 94%, for example 95%, 96%, 97%, 98% or 99% identity, at the nucleotide level, to any of the nucleotide sequences disclosed herein. The nucleic acid may comprise or consist of any of the nucleotide sequences disclosed herein.

Methods for preparing a nucleic acid molecule encoding a polypeptide of the invention are known in the art. For example, the polymerase chain reaction (PCR) can be used. The nucleotide sequence may be codon optimised to ensure optimum expression of the polypeptide in a particular cell or tissue type in vitro. For example, the sequence may be optimised for expression in HEK293T, HEK293 or CHO cells. Such cells are typically used to manufacture the polypeptide for clinical use. This can be done using routine techniques that are known in the art.

In a third aspect, the present invention provides a construct comprising a nucleic acid according to the second aspect of the invention. The construct is conveniently a recombinant construct.

The term "construct" as used herein is shorthand for a "nucleic acid construct" and generally refers to any artificially produced length of nucleic acid which may be DNA, cDNA or RNA, such as mRNA, obtained for example by cloning or produced by chemical synthesis. The DNA may be single or double stranded. Single stranded DNA may be the coding sense strand, or it may be the non-coding or anti-sense strand. For therapeutic use, the construct is preferably in a form capable of being expressed in the subject to be treated.

The construct of the third aspect of the invention may be part of an expression cassette. An expression cassette is typically part of a vector and typically comprises a promoter (for expression of the desired sequence), an open reading frame and a 3' untranslated region. The construct typically includes suitable sequences that allow cloning and expression of the nucleic acid of the second aspect of the invention. For example, in the construct the nucleic acid of the second aspect of the invention may be flanked by restriction sites, to enable cloning, and may be operably linked to one or more sequences that control expression, such as a promoter, terminator, operator or enhancer sequence.

Methods for preparing a construct of the third aspect of the invention are known in the art. For example, the polymerase chain reaction (PCR) can be used.

In a fourth aspect, the present invention provides a vector comprising a nucleic acid according to the second aspect of the invention or a construct according to the third aspect of the invention.

A "vector" as used herein refers to a vehicle for introducing a nucleic acid sequence into a cell or a virus for expression of a polypeptide or cloning (replication) of the nucleic acid that encodes the polypeptide. It refers to a recombinant construct, for example a plasmid, a virus or any other construct capable of expression or replication of the nucleic acid sequence upon introduction into a cell or virus. Vectors are typically referred to as either expression vectors (for example mammalian expression vectors) or cloning vectors (for example an *E. coli* cloning vector). Examples of vectors include, among others, plasmids, cosmids, artificial chromosomes and viral vectors (for example retrovirus (e.g. lentivirus), adenovirus, and adeno-associated virus (AAV) vectors). Typically, the vector is a lentivirus or AAV vector. Generally, any vector suitable to maintain, propagate or express nucleic acid to express a polypeptide in a host, may be used for expression in this regard. The nucleic acid or construct of the invention may be inserted into the vector using any suitable method known in the art.

The nucleic acids, constructs and vectors of the invention may be present within a cell.

In a fifth aspect, the present invention provides a cell comprising a nucleic acid according to the second aspect of the invention, a construct according to the third aspect of the invention or a vector according to the fourth aspect of the invention. The cell may be a prokaryotic cell, such as a bacterial cell, or eukaryotic cell, such as an animal, plant or yeast cell. Prokaryotic cells are particularly useful for cloning the nucleic acid of the invention. If the polypeptide of the invention is to be produced by the cell, a eukaryotic cell may be preferred. Nucleic acids, constructs and vectors of the invention may be introduced into cells by any suitable method, for example transfection or transduction.

In a sixth aspect, the present invention provides a pharmaceutical composition comprising a polypeptide according to the first aspect of the invention, a nucleic acid according to the second aspect of the invention, a construct according to the third aspect of the invention, a vector according to the fourth aspect of the invention or a cell according to the fifth aspect of the invention and one or more pharmaceutically acceptable carriers, diluents or excipients.

A pharmaceutical composition according to the present invention may be presented in a form that is ready for immediate use. Alternatively, the composition may be presented in a form that requires some preparation prior to administration.

Pharmaceutical compositions of the invention may be adapted for administration by any appropriate route, but will typically be adapted for intravenous administration.

The pharmaceutically acceptable carrier, diluent or excipient that is present in the pharmaceutical compositions of the invention may be any suitable pharmaceutically acceptable carrier, diluent or excipient that is known in the art.

Pharmaceutical compositions adapted for intravenous administration may include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents.

Excipients which may be used for injectable solutions include water, alcohols, polyols, glycerine and vegetable oils, for example. The compositions may be presented in unit-dose or multidose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts, buffers, coating agents or antioxidants.

The pharmaceutical composition of the invention may also contain at least one second therapeutically active agent, in addition to the polypeptide, nucleic acid, construct, vector or cell of the present invention. The second therapeutically active agent is typically an agent that is useful in the treatment of VWD or haemophilia. Accordingly, the second therapeutically active agent may be, for example, factor VIII, desmopressin, or an antifibrinolytic agent such as tranexamic acid. For treatment of haemophilia, the second therapeutically active agent is typically factor VIII.

In a seventh aspect, the present invention provides a polypeptide according to the first aspect of the invention, a nucleic acid according to the second aspect of the invention, a construct according to the third aspect of the invention, a vector according to the fourth aspect of the invention, a cell according to the fifth aspect of the invention or a pharmaceutical composition according to the sixth aspect of the invention for use in medicine.

The invention is typically used in the treatment of von Willebrand disease (VWD) or haemophilia. The present invention provides a gene therapy or recombinant protein approach for the treatment of VWD or haemophilia.

In an eighth aspect, the present invention provides a polypeptide according to the first aspect of the invention, a nucleic acid according to the second aspect of the invention, a construct according to the third aspect of the invention, a vector according to the fourth aspect of the invention, a cell according to the fifth aspect of the invention or a pharmaceutical composition according to the sixth aspect of the invention for use in the treatment of von Willebrand disease or haemophilia.

Put another way, the eighth aspect of the invention also provides use of a polypeptide according to the first aspect of the invention, a nucleic acid according to the second aspect of the invention, a construct according to the third aspect of the invention, a vector according to the fourth aspect of the invention, a cell according to the fifth aspect of the invention or a pharmaceutical composition according to the sixth aspect of the invention in the manufacture of a medicament for the treatment of von Willebrand disease or haemophilia.

The eighth aspect of the invention also extends to a method for the treatment of von Willebrand disease or haemophilia comprising administering to a subject in need thereof a polypeptide according to the first aspect of the invention, a nucleic acid according to the second aspect of the invention, a construct according to the third aspect of the invention, a vector according to the fourth aspect of the invention, a cell according to the fifth aspect of the invention or a pharmaceutical composition according to the sixth aspect of the invention.

The polypeptide, nucleic acid, construct, vector, cell or pharmaceutical composition is typically administered to the subject in need thereof in a "therapeutically effective amount". By "therapeutically effective amount" is meant an amount sufficient to show a therapeutic benefit to the subject, i.e. to reduce or relieve the symptoms of von Willebrand disease or haemophilia.

The subject is typically a human subject, but the invention may also find use in veterinary medicine and the subject may therefore be an animal, typically a mammal, for example a companion animal such as a dog, cat, rabbit, rat or mouse or an agricultural animal such as a cow, sheep, pig, horse, deer, chicken or goat, or a primate such as a chimpanzee, gorilla or monkey.

As used herein, "treatment" is also intended to cover preventative treatment, i.e. prophylaxis.

The eighth aspect of the invention also encompasses combination therapy, wherein the polypeptide, nucleic acid, construct, vector, cell or pharmaceutical composition is administered in combination with at least one second therapeutically active agent. The second therapeutically active agent may be as described herein in relation to the sixth aspect of the invention. The second therapeutically active agent may be administered separately, sequentially or in combination with the polypeptide, nucleic acid, construct, vector, cell or pharmaceutical composition of the invention.

Von Willebrand disease (VWD) is the most common inherited bleeding disorder. There are three subtypes: Type 3, in which patients have no plasma VWF, which leads to severe bleeding; Type 1, in which patients have reduced plasma VWF, which leads to variable bleeding (mild to severe); and Type 2, in which patients have functional defects in VWF, which leads to variable bleeding (mild to severe). Within Type 2 VWD, there are a number of subtypes: Type 2A—Reduced multimers; Type 2B—Enhanced platelet capture—reduced levels/multimers; Type 2M—Reduced platelet or collagen binding; Type 2N—Reduced FVIII binding; VWD Vicenza—Enhanced clearance. The present invention therefore finds use in the treatment of any one or more of these subtypes of VWD, i.e. Type 1, Type 2 (including Type 2A, Type 2B, Type 2M, Type 2N and VWD Vicenza) and Type 3.

Haemophilia is a mostly inherited bleeding disorder, which affects a patient's ability to form blood clots. Haemophilia A is caused by a lack of factor VIII and haemophilia B is caused by a lack of factor IX. Since VWD is the carrier for factor VIII and prolongs its half-life, the present invention therefore typically finds use in the treatment of haemophilia A. The use of recombinant factor VIII for the treatment of Haemophilia A has previously required the co-delivery of full length VWF in order to stabilise the delivered FVIII, but introduction of full length recombinant VWF into haemophiliacs who express native VWF can lead to complications including excessive clotting. The present invention avoids these drawbacks and therefore provides an improved treatment for haemophilia, particularly haemophilia A.

In the treatment of haemophilia, the VWD is typically administered in combination with factor VIII. Accordingly, the eighth aspect of the invention may extend to:

A polypeptide according to the first aspect of the invention, a nucleic acid according to the second aspect of the invention, a construct according to the third aspect of the invention, a vector according to the fourth aspect of the invention, a cell according to the fifth aspect of the invention or a pharmaceutical composition according to the sixth aspect of the invention and factor VIII for use in the treatment of haemophilia.

Use of a polypeptide according to the first aspect of the invention, a nucleic acid according to the second aspect of the invention, a construct according to the third aspect of the invention, a vector according to the fourth aspect of the invention, a cell according to the fifth aspect of the invention or a pharmaceutical composition according to the sixth aspect of the invention and factor VIII in the manufacture of a medicament for the treatment of haemophilia.

A method for the treatment of haemophilia comprising administering to a subject in need thereof a polypeptide according to the first aspect of the invention, a nucleic acid according to the second aspect of the invention, a construct according to the third aspect of the invention, a vector according to the fourth aspect of the invention, a cell according to the fifth aspect of the invention or a pharmaceutical composition according to the sixth aspect of the invention and factor VIII.

The haemophilia is typically haemophilia A. The factor VIII is typically recombinant factor VIII. The factor VIII may be modified, for example by the addition of polyethylene glycol (PEGylation), FC or albumin. The factor VIII may be administered separately, sequentially or in combination with the polypeptide, nucleic acid, construct, vector, cell or pharmaceutical composition of the invention.

Dosages of the polypeptide, nucleic acid, construct, vector, cell or pharmaceutical composition of the invention can vary between wide limits, depending upon the disease or disorder to be treated, the age and condition of the individual to be treated, whether the treatment is prophylactic or therapeutic, the type, onset, progression, severity, frequency, duration, or probability of the disease to be treated, the clinical endpoint desired, previous or simultaneous treatments, etc. Dosages can be based upon current existing protocols, empirically determined, using animal disease models or optionally in human clinical trials. A physician will ultimately determine appropriate dosages to be used. The dosage may be increased or decreased depending on any adverse side effects, complications or other risk factors of the treatment or therapy and the status of the subject.

The inventors have produced a novel truncated VWF variant, VWF-ΔD4C6, and have surprisingly demonstrated that VWF-ΔD4C6 demonstrates normal multimer formation and is able to interact with collagen under static conditions. Analysis of intracellular storage has also been performed and shows that while retaining normal expression, VWF-ΔD4C6 forms significantly fewer pseudo Webiel-Palade bodies when transfected into HEK293T cells. Significantly, the ability of the variant to capture platelets under shear stress is not altered. This data demonstrates that deletion of the D4-C6 region of VWF does not affect the ability of the molecule to bind to collagen under flow or capture platelets, at least under the tested shear rate. These findings are surprising given the size of the region that is deleted in VWF-AD4C6. The fact that the variant is fully functional means that it can be used in a gene therapy or recombinant protein approach for the treatment of VWD, as well as in the treatment of haemophilia, as a carrier molecule for FVIII. Gene therapy has previously been used successfully in the treatment of haemophilia A and B. However, gene therapy for VWD has been unsuccessful thus far. A drawback of gene therapy for VWD is the dominant-negative effect of many VWD causing mutations; which result in heterogeneous VWF multimers. The major obstacle however is the large size of the VWF gene; 8.4 kb for the coding sequence, this prevents efficient packaging into many viral vector systems. The present invention overcomes these deficiencies of the current treatment regimes for MD, with the truncated VWF molecule showing normal activity in vitro and a 2-3 fold increase in expression levels, as shown in the Examples herein.

Preferred features of the second and subsequent aspects of the invention are as described for the first aspect of the invention mutatis mutandis.

Description of the Sequences

```
amino acid sequence of full length human VWF
(2813 amino acids) NCBI Reference
Sequence: NM_000552.4
                                            SEQ ID NO: 1
MIPARFAGVLLALALILPGTLCAEGTRGRSSTARCSLFGSDFVNTFDG

SMYSFAGYCSYLLAGGCQKRSFSIIGDFQNGKRVSLSVYLGEFFDIHL

FVNGTVTQGDQRVSMPYASKGLYLETEAGYYKLSGEAYGFVARIDSG

NFQVLLSDRYFNKTCGLCGNFNIFAEDDFMTQEGTLTSDPYDFANSWA

LSSGEQWCERASPPSSSCNISSGEMQKGLWEQCQLLKSTSVFARCHPL

VDPEPFVALCEKTLCEACGGLECACPALLEYARTCAQEGMVLYGWTDH

SACSPVCPAGMEYRQCVSPCARTCQSLHINEMCQERCVDGCSCPEGQL

LDEGLCVESTECPCVHSGKRYPPGTSLSRDCNTCICRNSQWICSNEEC

PGECLVTGQSHFKSFDNRYFTFSGICQYLLARDCQDHSFSIVIETVQC

ADDRDAVCTRSVTVRLPGLHNSLVKLKHGAGVAMDGQDIQLPLLKGDL

RIQHTVTASVRLSYGEDLQMDWDGRGRLLVKLSPVYAGKTCGLCGNYN

GNQGDDFLTPSGLAEPRVEDFGNAWKLHGDCQDLQKQHSDPCALNPRM

TRFSEEACAVLTSPTFEACHRAVSPLPYLRNCRYDVCSCSDGRECLCG

ALASYAAACAGRGVRVAWREPGRCELNCPKGQVYLQCGTPCNLTCRSL

SYPDEECNEACLEGCFCPPGLYMDERGDCVPKAQCPCYYDGEIFQPED

IFSDHHTMCYCEDGFMHCTMSGVPGSLLPDAVLSSPLSHRSKRSLSCR

PPMVKLVCPADNLRAEGLECTKTCQNYDLECMSMGCVSGCLCPPGMVR

HENRCVALERCPCFHQGKEYAPGETVKIGCNTCVCRDRKWNCTDHVCD

ATCSTIGMAHYLTFDGLKYLFPGECQYVLVQDYCGSNPGTFRILVGNK

GCSHPSVKCKKRVTILVEGGEIELFDGEVNVKRPMKDETHFEVVESGR

YIILLLGKALSVVWDRHLSISVVLKQTYQEKVCGLCGNFDGIQNNDLT

SSNLQVEEDPVDFGNSWKVSSQCADTRKVPLDSSPATCHNNIMKQTMV

DSSCRILTSDVFQDCNKLVDPEPYLDVCIYDTCSCESIGDCACFCDTI

AAYAHVCAQHGKVVTWRTATLCPQSCEERNLRENGYECEWRYNSCAPA

CQVTCQHPEPLACPVQCVEGCHAHCPPGKILDELLQTCVDPEDCPVCE

VAGRRFASGKKVTLNPSDPEHCQICHCDVVNLTCEACQEPGGLVVPPT

DAPVSPTTLYVEDISEPPLHDFYCSRLLDLVFLLDGSSRLSEAEFECL

KAFVVDMMERLRISQKWVRVAVVEYHDGSHAYIGLKDRKRPSELRRIA

SQVKYAGSQVASTSEVLKYTLFQIFSKIDRPEASRIALLLMASQEPQR

MSRNFVRYVQGLKKKKVIVIPVGIGPHANLKQIRLIEKQAPENKAFVL

SSVDELEQQRDEIVSYLCDLAPEAPPPTLPPHMAQVTVGPGLLGVSTL

GPKRNSMVLDVAFVLEGSDKIGEADFNRSKEFMEEVIQRMDVGQDSIH

VTVLQYSYMVTVEYPFSEAQSKGDILQRVREIRYQGGNRTNTGLALRY

LSDHSFLVSQGDREQAPNLVYMVTGNPASDEIKRLPGDIQVVPIGVGP

NANVQELERIGWPNAPILIQDFETLPREAPDLVLQRCCSGEGLQIPTL

SPAPDCSQPLDVILLLDGSSSFPASYFDEMKSFAKAFISKANIGPRLT

QVSVLQYGSITTIDVPWNVVPEKAHLLSLVDVMQREGGPSQIGDALGF

AVRYLTSEMHGARPGASKAVVILVTDVSVDSVDAAADAARSNRVTVFP

IGIGDRYDAAQLRILAGPAGDSNVVKLQRIEDLPTMVTLGNSFLHKLC

SGFVRICMDEDGNEKRPGDVWTLPDQCHTVTCQPDGQTLLKSHRVNCD

RGLRPSCPNSQSPVKVEETCGCRWTCPCVCTGSSTRHIVTFDGQNFKL

TGSCSYVLFQNKEQDLEVILHNGACSPGARQGCMKSIEVKHSALSVEL

HSDMEVTVNGRLVSVPYVGGNMEVNVYGAIMHEVRFNHLGHIFTFTPQ

NNEFQLQLSPKTFASKTYGLCGICDENGANDFMLRDGTVTTDWKTLVQ

EWTVQRPGQTCQPILEEQCLVPDSSHCQVLLLPLFAECHKVLAPATFY

AICQQDSCHQEQVCEVIASYAHLCRTNGVCVDWRTPDFCAMSCPPSLV

YNHCEHGCPRHCDGNVSSCGDHPSEGCFCPPDKVMLEGSCVPEEACTQ

CIGEDGVQHQFLEAWVPDHQPCQICTCLSGRKVNCTTQPCPTAKAPTC

GLCEVARLRQNADQCCPEYECVCDPVSCDLPPVPHCERGLQPTLTNPG

ECRPNFTCACRKEECKRVSPPSCPPHRLPTLRKTQCCDEYECACNCVN

STVSCPLGYLASTATNDCGCTTTTCLPDKVCVHRSTIYPVGQFWEEGC

DVCTCTDMEDAVMGLRVAQCSQKPCEDSCRSGFTYVLHEGECCGRCLP

SACEVVTGSPRGDSQSSWKSVGSAWASPENPCLINECVRVKEEVFIQQ
```

RNVSCPQLEVPVCPSGFQLSCKTSACCPSCRCERMEACMLNGTVIGPG

KTVMIDVCTTCRCMVQVGVISGFKLECRKTTCNPCPLGYKEENNTGEC

CGRCLPTACTIQLRGGQIMTLKRDETLQDGCDTHFCKVNERGEYFWEK

RVTGCPPFDEHKCLAEGGKIMKIPGTCCDTCEEPECNDITARLQYVKV

GSCKSEVEVDIHYCQGKCASKAMYSIDINDVQDQCSCCSPTRTEPMQV

ALHCTNGSVVYHEVLNAMECKCSPRKCSK

Within this sequence, the domain structure is as follows:

Amino acids 1-22: signal peptide (SEQ ID NO: 5)

MIPARFAGVLLALALILPGTLC

Amino acids 23-763: D1D2 domains (Propeptide)

(SEQ ID NO: 6)

AEGTRGRSSTARCSLFGSDFVNTFDGSMYSFAGYCSYLLAGGCQKRSFSIIGDFQNGKRVSLSVYLGEF

FDIHLFVNGTVTQGDQRVSMPYASKGLYLETEAGYYKLSGEAYGFVARIDGSGNFQVLLSDRYFNKTCG

LCGNFNIFAEDDFMTQEGTLTSDPYDFANSWALSSGEQWCERASPPSSSCNISSGEMQKGLWEQCQLLK

STSVFARCHPLVDPEPFVALCEKTLCECAGGLECACPALLEYARTCAQEGMVLYGWTDHSACSPVCPAG

MEYRQCVSPCARTCQSLHINEMCQERCVDGCSCPEGQLLDEGLCVESTECPCVHSGKRYPPGTSLSRDC

NTCICRNSQWICSNEECPGECLVTGQSHFKSFDNRYFTFSGICQYLLARDCQDHSFSIVIETVQCADDR

DAVCTRSVTVRLPGLHNSLVKLKHGAGVAMDGQDIQLPLLKGDLRIQHTVTASVRLSYGEDLQMDWDGR

GRLLVKLSPVYAGKTCGLCGNYNGNQGDDFLTPSGLAEPRVEDFGNAWKLHGDCQDLQKQHSDPCALNP

RMTRFSEEACAVLTSPTFEACHRAVSPLPYLRNCRYDVCSCSDGRECLCGALASYAAACAGRGVRVAWR

EPGRCELNCPKGQVYLQCGTPCNLTCRSLSYPDEECNEACLEGCFCPPGLYMDERGDCVPKAQCPCYYD

GEIFQPEDIFSDHHTMCYCEDGFMHCTMSGVPGSLLPDAVLSSPLSHRSKR

Amino acids 764-864: D' domain (SEQ ID NO: 7)

SLSCRPPMVKLVCPADNLRAEGLECTKTCQNYDLECMSMGCVSGCLCPPGMVRHENRCVALERCPCFHQ

GKEYAPGETVKIGCNTCVCRDRKWNCTDHVCD

Amino acids 865-1270: D3 domain (SEQ ID NO: 8)

ATCSTIGMAHYLTFDGLKYLFPGECQYVLVQDYCGS

NPGTFRILVGNKGCSHPSVKCKKRVTILVEGGEIELFDGEVNVKRPMKDETHFEVVESGR

YIILLLGKALSVVWDRHLSISVVLKQTYQEKVCGLCGNFDGIQNNDLTSSNLQVEEDPVD

FGNSWKVSSQCADTRKVPLDSSPATCHNNIMKQTMVDSSCRILTSDVFQDCNKLVDPEPY

LDVCIYDTCSCESIGDCACFCDTIAAYAHVCAQHGKVVTWRTATLCPQSCEERNLRENGY

ECEWRYNSCAPACQVTCQHPEPLACPVQCVEGCHAHCPPGKILDELLQTCVDPEDCPVCE

VAGRRFASGKKVTLNPSDPEHCQICHCDVVNLTCEACQEPGGLVVPPTDAPVSPTTLYVE

DISEPPLHDF

Amino acids 1271-1453: A1 domain (SEQ ID NO: 9)

YCSRLLDLVFLLDGSSRLSEAEFECLKAFVVDMMERLRISQKWVRVAVVE

YHDGSHAYIGLKDRKRPSELRRIASQVKYAGSQVASTSEVLKYTLFQIFSKIDRPEASRI

ALLLMASQEPQRMSRNFVRYVQGLKKKKVIVIPVGIGPHANLKQIRLIEKQAPENKAFVL

SSVDELEQQRDEI

Amino acids 1454-1497: A1 linker region (SEQ ID NO: 10)

VSYLCDLAPEAPPPTLPPHMAQVTVGPGLLGVSTLGPKRNSMVL

```
Amino acids 1498-1670: A2 domain
                                                                    (SEQ ID NO: 11)
DVAFVLEGSDKIGEADFNRSKEFMEEVIQRMDVGQDSIHVTVLQYSYMVTVEYPFSEAQSKGD
ILQRVREIRYQGGNRTNTGLALRYLSDHSFLVSQGDREQAPNLVYMVTGNPASDEIKRLP
GDIQVVPIGVGPNANVQELERIGWPNAPILIQDFETLPREAPDLVLQRCC Amino acids 1671-1874: A3 domain
                                                                    (SEQ ID NO: 12)
SGEGLQIPTLSPAPDCSQPLDVILLLDGSSSFPASYFDEMKSFAKAFISKANIGPRLTQVSVLQY
GSITTIDVPWNVVPEKAHLLSLVDVMQREGGPSQIGDALGFAVRYLTSEMHGARPGASKAVVILVTDVS
VDSVDAAADAARSNRVTVFPIGIGDRYDAAQLRILAGPAGDSNVVKLQRIEDLPTMVTLGNSFLHKLCS
G Amino acids 1875-2254: D4 domain
                                                                    (SEQ ID NO: 13)
FVRICMDEDGNEKRPGDVWTLPDQCHTVTCQPDGQTLLKSHRVNCDRGLRPSCPNSQSPVKVEETCGCR
WTCPCVCTGSSTRHIVTFDGQNFKLTGSCSYVLFQNKEQDLEVILHNGACSPGARQGCMKSIEVKHSAL
SVELHSDMEVTVNGRLVSVPYVGGNMEVNVYGAIMHEVRFNHLGHIFTFTPQNNEFQLQLSPKTFASKT
YGLCGICDENGANDFMLRDGTVTTDWKTLVQEWTVQRPGQTCQPILEEQCLVPDSSHCQVLLLPLFAEC
HKVLAPATFYAICQQDSCHQEQVCEVIASYAHLCRTNGVCVDWRTPDFCAMSCPPSLVYNHCEHGCPRH
CDGNVSSCGDHPSEGCFCPPDKVMLEGSCVPEEAC Amino acids 2255-2333: C1 domain
                                                                    (SEQ ID NO: 14)
TQCIGEDGVQHQFLEAWVPDHQPCQICTCLSGRKVNCTTQPCPTAKAPTCGLCEVARLRQNADQCCPEY
ECVCDPVSCD Amino acids 2334-2402: C2 domain
                                                                    (SEQ ID NO: 15)
LPPVPHCERGLQPTLTNPGECRPNFTCACRKEECKRVSPPSCPPHRLPTLRKTQCCDEYECACNCVNST Amino acids 2403-2428: C2C3 loop
                                                                    (SEQ ID NO: 16)
VSCPLGYLASTATNDCGCTTTTCLPD Amino acids 2429-2496: C3 domain
                                                                    (SEQ ID NO: 17)
KVCVHRSTIYPVGQFWEEGCDVCTCTDMEDAVMGLRVAQCSQKPCEDSCRSGFTYVLHEGECCGRCLP Amino acids 2497-2577: C4 domain
                                                                    (SEQ ID NO: 18)
SACEVVTGSPRGDSQSSWKSVGSQWASPENPCLINECVRVKEEVFIQQRNVSCPQLEVPVCPSGFQLSC
KTSACCPSCRCE Amino acids 2578-2646: C5 domain
                                                                    (SEQ ID NO: 19)
RMEACMLNGTVIGPGKTVMIDVCTTCRCMVQVGVISGFKLECRKTTCNPCPLGYKEENNTGECCGRCLP Amino acids 2647-2720: C6 domain
                                                                    (SEQ ID NO: 20)
TACTIQLRGGQIMTLKRDETLQDGCDTHFCKVNERGEYFWEKRVTGCPPFDEHKCLAEGGKIMKI
PGTCCDTCE Amino acids 2721-2813: CK domain
                                                                    (SEQ ID NO: 21)
EPECNDITARLQYVKVGSCKSEVEVDIHYCQGKCASKAMYSIDINDVQDQCSCCSPTRTEPMQVALHCT
NGSVVYHEVLNAMECKCSPRKCSK full length human VWF cDNA sequence (8442 base pairs)
                                                                    SEQ ID NO: 2
ATGATTCCTGCCAGATTTGCCGGGGTGCTGCTTGCTCTGGCCCTCATTTTGCCAGGGACCCTTTGTGCAGAAGGAA
CTCGCGGCAGGTCATCCACGGCCCGATGCAGCCTTTTCGGAAGTGACTTCGTCAACACCTTTGATGGGAGCATGTA
CAGCTTTGCGGGATACTGCAGTTACCTCCTGGCAGGGGGCTGCCAGAAACGCTCCTTCTCGATTATTGGGGACTTC
```

-continued

```
CAGAATGGCAAGAGAGTGAGCCTCTCCGTGTATCTTGGGGAATTTTTTGACATCCATTTGTTTGTCAATGGTACCGT

GACACAGGGGGACCAAAGAGTCTCCATGCCCTATGCCTCCAAAGGGCTGTATCTAGAAACTGAGGCTGGGTACTA

CAAGCTGTCCGGTGAGGCCTATGGCTTTGTGGCCAGGATCGATGGCAGCGGCAACTTTCAAGTCCTGCTGTCAGAC

AGATACTTCAACAAGACCTGCGGGCTGTGTGGCAACTTTAACATCTTTGCTGAAGATGACTTTATGACCCAAGAAG

GGACCTTGACCTCGGACCCTTATGACTTTGCCAACTCATGGGCTCTGAGCAGTGGAGAACAGTGGTGTGAACGGGC

ATCTCCTCCCAGCAGCTCATGCAACATCTCCTCTGGGGAAATGCAGAAGGGCCTGTGGGAGCAGTGCCAGCTTCTG

AAGAGCACCTCGGTGTTTGCCCGCTGCCACCCTCTGGTGGACCCCGAGCCTTTTGTGGCCCTGTGTGAGAAGACTT

TGTGTGAGTGTGCTGGGGGGCTGGAGTGCGCCTGCCCTGCCCTCCTGGAGTACGCCCGGACCTGTGCCCAGGAGG

GAATGGTGCTGTACGGCTGGACCGACCACAGCGCGTGCAGCCCAGTGTGCCCTGCTGGTATGGAGTATAGGCAGT

GTGTGTCCCCTTGCGCCAGGACCTGCCAGAGCCTGCACATCAATGAAATGTGTCAGGAGCGATGCGTGGATGGCT

GCAGCTGCCCTGAGGGACAGCTCCTGGATGAAGGCCTCTGCGTGGAGAGCACCGAGTGTCCCTGCGTGCATTCCG

GAAAGCGCTACCCTCCCGGCACCTCCCTCTCGAGACTGCAACACCTGCATTTGCCGAAACAGCCAGTGGATCTG

CAGCAATGAAGAATGTCCAGGGGAGTGCCTTGTCACTGGTCAATCCCACTTCAAGAGCTTTGACAACAGATACTTC

ACCTTCAGTGGGATCTGCCAGTACCTGCTGGCCCGGGATTGCCAGGACCACTCCTTCTCCATTGTCATTGAGACTGT

CCAGTGTGCTGATGACCGCGACGCTGTGTGCACCCGCTCCGTCACCGTCCGGCTGCCTGGCCTGCACAACAGCCTT

GTGAAACTGAAGCATGGGGCAGGAGTTGCCATGGATGGCCAGGACATCCAGCTCCCCCTCCTGAAAGGTGACCTC

CGCATCCAGCATACAGTGACGGCCTCCGTGCGCCTCAGCTACGGGGAGGACCTGCAGATGGACTGGGATGGCCGC

GGGAGGCTGCTGGTGAAGCTGTCCCCCGTCTACGCCGGGAAGACCTGCGGCCTGTGTGGGAATTACAATGGCAAC

CAGGGCGACGACTTCCTTACCCCCTCTGGGCTGGCAGAGCCCCGGGTGGAGGACTTCGGGAACGCCTGGAAGCTG

CACGGGGACTGCCAGGACCTGCAGAAGCAGCACAGCGATCCCTGCGCCCTCAACCCGCGCATGACCAGGTTCTCC

GAGGAGGCGTGCGCGGTCCTGACGTCCCCCACATTCGAGGCCTGCCATCGTGCCGTCAGCCCGCTGCCCTACCTGC

GGAACTGCCGCTACGACGTGTGCTCCTGCTCGGACGGCCGCGAGTGCCTGTGCGGCGCCCTGGCCAGCTATGCCGC

GGCCTGCGCGGGAGAGGCGTGCGCGTCGCGTGGCGCGAGCCAGGCCGCTGTGAGCTGAACTGCCCGAAAGGCC

AGGTGTACCTGCAGTGCGGGACCCCCTGCAACCTGACCTGCCGCTCTCTCTCTTACCCGGATGAGGAATGCAATGA

GGCCTGCCTGGAGGGCTGCTTCTGCCCCCCAGGGCTCTACATGGATGAGAGGGGGACTGCGTGCCCAAGGCCCA

GTGCCCCTGTTACTATGACGGTGAGATCTTCCAGCCAGAAGACATCTTCTCAGACCATCACACCATGTGCTACTGT

GAGGATGGCTTCATGCACTGTACCATGAGTGGAGTCCCCGGAAGCTTGCTGCCTGACGCTGTCCTCAGCAGTCCCC

TGTCTCATCGCAGCAAAAGGAGCCTATCCTGTCGGCCCCCATGGTCAAGCTGGTGTGTCCCGCTGACAACCTGCG

GGCTGAAGGGCTCGAGTGTACCAAAACGTGCCAGAACTATGACCTGGAGTGCATGAGCATGGGCTGTGTCTCTGG

CTGCCTCTGCCCCCCGGGCATGGTCCGGCATGAGAACAGATGTGTGGCCCTGGAAAGGTGTCCCTGCTTCCATCAG

GGCAAGGAGTATGCCCCTGGAGAAACAGTGAAGATTGGCTGCAACACTTGTGTCTGTCGGGACCGGAAGTGGAAC

TGCACAGACCATGTGTGTGATGCCACGTGCTCCACGATCGGCATGGCCCACTACCTCACCTTCGACGGGCTCAAAT

ACCTGTTCCCCGGGGAGTGCCAGTACGTTCTGGTGCAGGATTACTGCGGCAGTAACCCTGGGACCTTTCGGATCCT

AGTGGGGAATAAGGGATGCAGCCACCCCTCAGTGAAATGCAAGAAACGGGTCACCATCCTGGTGGAGGGAGGAG

AGATTGAGCTGTTTGACGGGGAGGTGAATGTGAAGAGGCCCATGAAGGATGAGACTCACTTTGAGGTGGTGGAGT

CTGGCCGGTACATCATTCTGCTGCTGGGCAAAGCCCTCTCCGTGGTCTGGGACCGCCACCTGAGCATCTCCGTGGT

CCTGAAGCAGACATACCAGGAGAAAGTGTGTGGCCTGTGTGGGAATTTTGATGGCATCCAGAACAATGACCTCAC

CAGCAGCAACCTCCAAGTGGAGGAAGACCCTGTGGACTTTGGGAACTCCTGGAAAGTGAGCTCGCAGTGTGCTGA

CACCAGAAAAGTGCCTCTGGACTCATCCCCTGCCACCTGCCATAACAACATCATGAAGCAGACGATGGTGGATTCC

TCCTGTAGAATCCTTACCAGTGACGTCTTCCAGGACTGCAACAAGCTGGTGGACCCCGAGCCATATCTGGATGTCT

GCATTTACGACACCTGCTCCTGTGAGTCCATTGGGGACTGCGCCTGCTTCTGCGACACCATTGCTGCCTATGCCCAC
```

-continued

```
GTGTGTGCCCAGCATGGCAAGGTGGTGACCTGGAGGACGGCCACATTGTGCCCCCAGAGCTGCGAGGAGAGGAAT
CTCCGGGAGAACGGGTATGAGTGTGAGTGGCGCTATAACAGCTGTGCACCTGCCTGTCAAGTCACGTGTCAGCAC
CCTGAGCCACTGGCCTGCCCTGTGCAGTGTGTGGAGGGCTGCCATGCCCACTGCCCTCCAGGGAAAATCCTGGATG
AGCTTTTGCAGACCTGCGTTGACCCTGAAGACTGTCCAGTGTGTGAGGTGGCTGGCCGGCGTTTTGCCTCAGGAAA
GAAAGTCACCTTGAATCCCAGTGACCCTGAGCACTGCCAGATTTGCCACTGTGATGTTGTCAACCTCACCTGTGAA
GCCTGCCAGGAGCCGGGAGGCCTGGTGGTGCCTCCCACAGATGCCCCGGTGAGCCCCACCACTCTGTATGTGGAG
GACATCTCGGAACCGCCGTTGCACGATTTCTACTGCAGCAGGCTACTGGACCTGGTCTTCCTGCTGGATGGCTCCT
CCAGGCTGTCCGAGGCTGAGTTTGAAGTGCTGAAGGCCTTTGTGGTGGACATGATGGAGCGGCTGCGCATCTCCCA
GAAGTGGGTCCGCGTGGCCGTGGTGGAGTACCACGACGGCTCCCACGCCTACATCGGGCTCAAGGACCGGAAGCG
ACCGTCAGAGCTGCGGCGCATTGCCAGCCAGGTGAAGTATGCGGGCAGCCAGGTGGCCTCCACCAGCGAGGTCTT
GAAATACACACTGTTCCAAATCTTCAGCAAGATCGACCGCCCTGAAGCCTCCCGCATCGCCCTGCTCCTGATGGCC
AGCCAGGAGCCCCAACGGATGTCCCGGAACTTTGTCCGCTACGTCCAGGGCCTGAAGAAGAAGAAGGTCATTGTG
ATCCCGGTGGGCATTGGGCCCCATGCCAACCTCAAGCAGATCCGCCTCATCGAGAAGCAGGCCCCTGAGAACAAG
GCCTTCGTGCTGAGCAGTGTGGATGAGCTGGAGCAGCAAAGGGACGAGATCGTTAGCTACCTCTGTGACCTTGCCC
CTGAAGCCCCTCCTCCTACTCTGCCCCCCCACATGGCACAAGTCACTGTGGGCCCGGGGCTCTTGGGGGTTTCGAC
CCTGGGGCCCAAGAGGAACTCCATGGTTCTGGATGTGGCGTTCGTCCTGGAAGGATCGGACAAAATTGGTGAAGC
CGACTTCAACAGGAGCAAGGAGTTCATGGAGGAGGTGATTCAGCGGATGGATGTGGGCCAGGACAGCATCCACGT
CACGGTGCTGCAGTACTCCTACATGGTGACCGTGGAGTACCCCTTCAGCGAGGCACAGTCCAAAGGGGACATCCT
GCAGCGGGTGCGAGAGATCCGCTACCAGGGCGGCAACAGGACCAACACTGGGCTGGCCCTGCGGTACCTCTCTGA
CCACAGCTTCTTGGTCAGCCAGGGTGACCGGGAGCAGGCGCCCAACCTGGTCTACATGGTCACCGGAAATCCTGC
CTCTGATGAGATCAAGAGGCTGCCTGGAGACATCCAGGTGGTGCCCATTGGAGTGGGCCCTAATGCCAACGTGCA
GGAGCTGGAGAGGATTGGCTGGCCCAATGCCCCTATCCTCATCCAGGACTTTGAGACGCTCCCCCGAGAGGCTCCT
GACCTGGTGCTGCAGAGGTGCTGCTCCGGAGAGGGGCTGCAGATCCCCACCCTCTCCCCTGCACCTGACTGCAGCC
AGCCCCTGGACGTGATCCTTCTCCTGGATGGCTCCTCCAGTTTCCCAGCTTCTTATTTTGATGAAATGAAGAGTTTC
GCCAAGGCTTTCATTTCAAAAGCCAATATAGGGCCTCGTCTCACTCAGGTGTCAGTGCTGCAGTATGGAAGCATCA
CCACCATTGACGTGCCATGGAACGTGGTCCCGGAGAAAGCCCATTTGCTGAGCCTTGTGGACGTCATGCAGCGGG
AGGGAGGCCCCAGCCAAATCGGGGATGCCTTGGGCTTTGCTGTGCGATACTTGACTTCAGAAATGCATGGTGCCA
GGCCGGGAGCCTCAAAGGCGGTGGTCATCCTGGTCACGGACGTCTCTGTGGATTCAGTGGATGCAGCAGCTGATG
CCGCCAGGTCCAACAGAGTGACAGTGTTCCCTATTGGAATTGGAGATCGCTACGATGCAGCCCAGCTACGGATCTT
GGCAGGCCCAGCAGGCGACTCCAACGTGGTGAAGCTCCAGCGAATCGAAGACCTCCCTACCATGGTCACCTTGGG
CAATTCCTTCCTCCACAAACTGTGCTCTGGATTTGTTAGGATTTGCATGGATGAGGATGGGAATGAGAAGAGGCCC
GGGGACGTCTGGACCTTGCCAGACCAGTGCCACACCGTGACTTGCCAGCCAGATGGCCAGACCTTGCTGAAGAGT
CATCGGGTCAACTGTGACCGGGGGCTGAGGCCTTCGTGCCCTAACAGCCAGTCCCTGTTAAAGTGGAAGAGACC
TGTGGCTGCCGCTGGACCTGCCCCTGCGTGTGCACAGGCAGCTCCACTCGGCACATCGTGACCTTTGATGGGCAGA
ATTTCAAGCTGACTGGCAGCTGTTCTTATGTCCTATTTCAAAACAAGGAGCAGGACCTGGAGGTGATTCTCCATAA
TGGTGCCTGCAGCCCTGGAGCAAGGCAGGGCTGCATGAAATCCATCGAGGTGAAGCACAGTGCCCTCTCCGTCGA
GCTGCACAGTGACATGGAGGTGACGGTGAATGGGAGACTGGTCTCTGTTCCTTACGTGGGTGGGAACATGGAAGT
CAACGTTTATGGTGCCATCATGCATGAGGTCAGATTCAATCACCTTGGTCACATCTTCACATTCACTCCACAAAAC
AATGAGTTCCAACTGCAGCTCAGCCCCAAGACTTTTGCTTCAAAGACGTATGGTCTGTGTGGGATCTGTGATGAGA
ACGGAGCCAATGACTTCATGCTGAGGGATGGCACAGTCACCACAGACTGGAAAACACTTGTTCAGGAATGGACTG
```

```
TGCAGCGGCCAGGGCAGACGTGCCAGCCCATCCTGGAGGAGCAGTGTCTTGTCCCGACAGCTCCCACTGCCAGG
TCCTCCTCTTACCACTGTTTGCTGAATGCCACAAGGTCCTGGCTCCAGCCACATTCTATGCCATCTGCCAGCAGGAC
AGTTGCCACCAGGAGCAAGTGTGTGAGGTGATCGCCTCTTATGCCCACCTCTGTCGGACCAACGGGGTCTGCGTTG
ACTGGAGGACACCTGATTTCTGTGCTATGTCATGCCCACCATCTCTGGTCTACAACCACTGTGAGCATGGCTGTCCC
CGGCACTGTGATGGCAACGTGAGCTCCTGTGGGGACCATCCCTCCGAAGGCTGTTTCTGCCCTCCAGATAAAGTCA
TGTTGGAAGGCAGCTGTGTCCCTGAAGAGGCCTGCACTCAGTGCATTGGTGAGGATGGAGTCCAGCACCAGTTCCT
GGAAGCCTGGGTCCCGGACCACCAGCCCTGTCAGATCTGCACATGCCTCAGCGGGCGGAAGGTCAACTGCACAAC
GCAGCCCTGCCCCACGGCCAAAGCTCCCACGTGTGGCCTGTGTGAAGTAGCCCGCCTCCGCCAGAATGCAGACCA
GTGCTGCCCCGAGTATGAGTGTGTGTGACCCAGTGAGCTGTGACCTGCCCCAGTGCCTCACTGTGAACGTGGC
CTCCAGCCCACACTGACCAACCCTGGCGAGTGCAGACCCAACTTCACCTGCGCCTGCAGGAAGGAGGAGTGCAAA
AGAGTGTCCCCACCCTCCTGCCCCCGCACCGTTTGCCCACCCTTCGGAAGACCCAGTGCTGTGATGAGTATGAGT
GTGCCTGCAACTGTGTCAACTCCACAGTGAGCTGTCCCCTTGGGTACTTGGCCTCAACCGCCACCAATGACTGTGG
CTGTACCACAACCACCTGCCTTCCCGACAAGGTGTGTGTCCACCGAAGCACCATCTACCCTGTGGGCCAGTTCTGG
GAGGAGGGCTGCGATGTGTGCACCTGCACCGACATGGAGGATGCCGTGATGGGCCTCCGCGTGGCCCAGTGCTCC
CAGAAGCCCTGTGAGGACAGCTGTCGGTCGGGCTTCACTTACGTTCTGCATGAAGGCGAGTGCTGTGGAAGGTGC
CTGCCATCTGCCTGTGAGGTGGTGACTGGCTCACCGCGGGGGACTCCCAGTCTTCCTGGAAGAGTGTCGGCTCCC
AGTGGGCCTCCCCGGAGAACCCCTGCCTCATCAATGAGTGTGTCCGAGTGAAGGAGGAGGTCTTTATACAACAAA
GGAACGTCTCCTGCCCCCAGCTGGAGGTCCCTGTCTGCCCCTCGGCTTTCAGCTGAGCTGTAAGACCTCAGCGTG
CTGCCCAAGCTGTCGCTGTGAGCGCATGGAGGCCTGCATGCTCAATGGCACTGTCATTGGGCCCGGGAAGACTGTG
ATGATCGATGTGTGCACGACCTGCCGCTGCATGGTGCAGGTGGGGGTCATCTCTGGATTCAAGCTGGAGTGCAGG
AAGACCACCTGCAACCCCTGCCCCCTGGGTTACAAGGAAGAAAATAACACAGGTGAATGTTGTGGGAGATGTTTG
CCTACGGCTTGCACCATTCAGCTAAGAGGAGGACAGATCATGACACTGAAGCGTGATGAGACGCTCCAGGATGGC
TGTGATACTCACTTCTGCAAGGTCAATGAGAGAGGAGAGTACTTCTGGGAGAAGAGGGTCACAGGCTGCCCACCC
TTTGATGAACACAAGTGTCTGGCTGAGGGAGGTAAAATTATGAAAATTCCAGGCACCTGCTGTGACACATGTGAG
GAGCCTGAGTGCAACGACATCACTGCCAGGCTGCAGTATGTCAAGGTGGGAAGCTGTAAGTCTGAAGTAGAGGTG
GATATCCACTACTGCCAGGGCAAATGTGCCAGCAAAGCCATGTACTCCATTGACATCAACGATGTGCAGGACCAG
TGCTCCTGCTGCTCTCCGACACGGACGGAGCCCATGCAGGTGGCCCTGCACTGCACCAATGGCTCTGTTGTGTACC
ATGAGGTTCTCAATGCCATGGAGTGCAAATGCTCCCCCAGGAAGTGCAGCAAGTGA
```

Within the sequence of SEQ ID NO: 2, nucleotides 5623-8160 (underlined) encode the D4-D6 domains (SEQ ID NO: 22)

```
VWF deletion D4C6 amino acid sequence
(1967 amino acids)
                                            SEQ ID NO: 3
MIPARFAGVLLALALILPGTLCAEGTRGRSSTARCSLFGSDFVNTFDG
SMYSFAGYCSYLLAGGCQKRSFSIIGDFQNGKRVSLSVYLGEFFDIHL
FVNGTVTQGDQRVSMPYASKGLYLETEAGYYKLSGEAYGFVARIDGSG
NFQVLLSDRYFNKTCGLCGNFNIFAEDDFMTQEGTLTSDPYDFANSWA
LSSGEQWCERASPPSSSCNISSGEMQKGLWEQCQLLKSTSVFARCHPL
VDPEPFVALCEKTLCECAGGLECACPALLEYARTCAQEGMVLYGWTDH
SACSPVCPAGMEYRQCVSPCARTCQSLHINEMCQERCVDGCSCPEGQL
LDEGLCVESTECPCVHSGKRYPPGTSLSRDCNTCICRNSQWICSNEEC
PGECLVTGQSHFKSFDNRYFTFSGICQYLLARDCQDHSFSIVIETVQC
ADDRDAVCTRSVTVRLPGLHNSLVKLKHGGAVAMDGQDIQLPLLKGDL
RIQHTVTASVRLSYGEDLQMDWDGRGRLLVKLSPVYAGKTCGLCGNYN
GNQGDDFLTPSGLAEPRVEDFGNAWKLHGDCQDLQKQHSDPCALNPRM
TRFSEEACAVLTSPTFEACHRAVSPLPYLRNCRYDVCSCSDGRECLCG
ALASYAAACAGRGVRVAWREPGRCELNCPKGQVYLQCGTPCNLTCRSL
SYPDEECNEACLEGCFCPPGLYMDERGDCVPKAQCPCYYDGEIFQPED
IFSDHHTMCYCEDGFMHCTMSGVPGSLLPDAVLSSPLSHRSKRSLSCR
PPMVKLVCPADNLRAEGLECTKTCQNYDLECMSMGCVSGCLCPPGMVR
HENRCVALERCPCFHQGKEYAPGETVKIGCNTCVCRDRKWNCTDHVCD
ATCSTIGMAHYLTFDGLKYLFPGECQYVLVQDYCGSNPGTFRILVGNK
```

```
GCSHPSVKCKKRVTILVEGGEIELFDGEVNVKRPMKDETHFEVVESGR

YIILLLGKALSVVWDRHLSISVVLKQTYQEKVCGLCGNFDGIQNNDLT

SSNLQVEEDPVDFGNSWKVSSQCADTRKVPLDSSPATCHNNIMKQTMV

DSSCRILTSDVFQDCNKLVDPEPYLDVCIYDTCSCESIGDCACFCDTI

AAYAHVCAQHGKVVTWRTATLCPQSCEERNLRENGYECEWRYNSCAPA

CQVTCQHPEPLACPVQCVEGCHAHCPPGKILDELLQTCVDPEDCPVCE

VAGRRFASGKKVTLNPSDPEHCQICHCDVVNLTCEACQEPGGLVVPPT

DAPVSPTTLYVEDISEPPLHDFYCSRLLDLVFLLDGSSRLSEAEFEVL

KAFVVDMMERLRISQKWVRVAVVEYHDGSHAYIGLKDRKRPSELRRIA

SQVKYAGSQVASTSEVLKYTLFQIFSKIDRPEASRIALLLMASQEPQR

MSRNFVRYVQGLKKKKVIVIPVGIGPHANLKQIRLIEKQAPENKAFVL
```

```
Amino acids 1-22: signal peptide
                                                        (SEQ ID NO: 23)
MIPARFAGVLLALALILPGTLC Amino acids 23-763: D1D2 domains (Propeptide)
                                                        (SEQ ID NO: 24)
AEGTRGRSSTARCSLFGSDFVNTFDGSMYSFAGYCSYL

LAGGCQKRSFSIIGDFQNGKRVSLSVYLGEFFDIHLFVNGTVTQGDQRVSMPYASKGLYL

ETEAGYYKLSGEAYGFVARIDSGNFQVLLSDRYFNKTCGLCGNFNIFAEDDFMTQEGTL

TSDPYDFANSWALSSGEQWCERASPPSSSCNISSGEMQKGLWEQCQLLKSTSVFARCHPL

VDPEPFVALCEKTLCECAGGLECACPALLEYARTCAQEGMVLYGWTDHSACSPVCPAGME

YRQCVSPCARTCQSLHINEMCQERCVDGCSCPEGQLLDEGLCVESTECPCVHSGKRYPPG

TSLSRDCNTCICRNSQWICSNEECPGECLVTGQSHFKSFDNRYFTFSGICQYLLARDCQD

HSFSIVIETVQCADDRDAVCTRSVTVRLPGLHNSLVKLKHGAGVAMDGQDIQLPLLKGDL

RIQHTVTASVRLSYGEDLQMDWDGRGRLLVKLSPVYAGKTCGLCGNYNGNQGDDFLTPSG

LAEPRVEDFGNAWKLHGDCQDLQKQHSDPCALNPRMTRFSEEACAVLTSPTFEACHRAVS

PLPYLRNCRYDVCSCSDGRECLCGALASYAAACAGRGVRVAWREPGRCELNCPKGQVYLQ

CGTPCNLTCRSLSYPDEECNEACLEGCFCPPGLYMDERGDCVPKAQCPCYYDGEIFQPED

IFSDHHTMCYCEDGFMHCTMSGVPGSLLPDAVLSSPLSHRSKR

Amino acids 764-864: D' domain
                                                        (SEQ ID NO: 25)
SLSCRPPMVKLVCPADNLRAEGLECTKTCQNYDLECMSMGCVSGCLCPPGMVRHENRCVALERCPCFHQ

GKEYAPGETVKIGCNTCVCRDRKWNCTDHVCD

Amino acids 865-1270: D3 domain
                                                        (SEQ ID NO: 26)
ATCSTIGMAHYLTFDGLKYLFPGECQYVLVQDYCGS

NPGTFRILVGNKGCSHPSVKCKKRVTILVEGGEIELFDGEVNVKRPMKDETHFEVVESGR

YIILLLGKALSVVWDRHLSISVVLKQTYQEKVCGLCGNFDGIQNNDLTSSNLQVEEDPVD

FGNSWKVSSQCADTRKVPLDSSPATCHNNIMKQTMVDSSCRILTSDVFQDCNKLVDPEPY

LDVCIYDTCSCESIGDCACFCDTIAAYAHVCAQHGKVVTWRTATLCPQSCEERNLRENGY
```

```
SSVDELEQQRDEIVSYLCDLAPEAPPPTLPPHMAQVTVGPGLLGVSTL

GPKRNSMVLDVAFVLEGSDKIGEADFNRSKEFMEEVIQRMDVGQDSIH

VTVLQYSYMVTVEYPFSEAQSKGDILQRVREIRYQGGNRTNTGLALRY

LSDHSFLVSQGDREQAPNLVYMVTGNPASDEIKRLPGDIQVVPIGVGP

NANVQELERIGWPNAPILIQDFETLPREAPDLVLQRCCSGEGLQIPTL

SPAPDCSQPLDVILLLDGSSSFPASYFDEMKSFAKAFISKANIGPRLT

QVSVLQYGSITTIDVPWNVVPEKAHLLSLVDVMQREGGPSQIGDALGF

AVRYLTSEMHGARPGASKAVVILVTDVSVDSVDAAADAARSNRVTVFP

IGIGDRYDAAQLRILAGPAGDSNVVKLQRIEDLPTMVTLGNSFLHKLC

SGEPECNDITARLQYVKVGSCKSEVEVDIHYCQGKCASKAMYSIDIND

VQDQCSCCSPTRTEPMQVALHCTNGSVVYHEVLNAMECKCSPRKCSK
```

Within this sequence, the domain structure is as follows:

-continued

ECEWRYNSCAPACQVTCQHPEPLACPVQCVEGCHAHCPPGKILDELLQTCVDPEDCPVCE

VAGRRFASGKKVTLNPSDPEHCQICHCDVVNLTCEACQEPGGLVVPPTDAPVSPTTLYVE

DISEPPLHDF

Amino acids 1271-1453: A1 domain
(SEQ ID NO: 27)

YCSRLLDLVFLLDGSSRLSEAEFEVLKAFVVDMMERLRISQKWVRVAVVE

YHDGSHAYIGLKDRKRPSELRRIASQVKYAGSQVASTSEVLKYTLFQIFSKIDRPEASRI

ALLLMASQEPQRMSRNFVRYVQGLKKKKVIVIPVGIGPHANLKQIRLIEKQAPENKAFVL

SSVDELEQQRDEI

Amino acids 1454-1497: A1 linker region
(SEQ ID NO: 28)

VSYLCDLAPEAPPPTLPPHMAQVTVGPGLLGVSTLGPKRNSMVL

Amino acids 1498-1670: A2 domain
(SEQ ID NO: 29)

DVAFVLEGSDKIGEADFNRSKEFMEEVIQRMDVGQDSIHVTVLQYSYMVTVEYPFSEAQSKGD

ILQRVREIRYQGGNRTNTGLALRYLSDHSFLVSQGDREQAPNLVYMVTGNPASDEIKRLP

GDIQVVPIGVGPNANVQELERIGWPNAPILIQDFETLPREAPDLVLQRCC

Amino acids 1671-1874: A3 domain
(SEQ ID NO: 30)

SGEGLQIPTLSPAPDCSQPLDVILLLDGSSSFPASYFDEMKSFAKAFISKANIGPRLTQVSVLQYGSIT

TIDVPWNVVPEKAHLLSLVDVMQREGGPSQIGDALGFAVRYLTSEMHGARPGASKAVVILVTDVSVDSV

DAAADAARSNRVTVFPIGIGDRYDAAQLRILAGPAGDSNVVKLQRIEDLPTMVTLGNSFLHKLCSG

Amino acids 1875 to 1967: CK domain
(SEQ ID NO: 31)

EPECNDITARLQYVKVGSCKSEVEVDIHYCQGKCASKAMYSIDINDVQDQCSCCSPTRTEPMQVALHCT

NGSVVYHEVLNAMECKCSPRKCSK

VWF deletion D4C6 cDNA sequence (5904 base pairs)
SEQ ID NO: 4

ATGATTCCTGCCAGATTTGCCGGGGTGCTGCTTGCTCTGGCCCTCATTTTGCCAGGGACCCTTTGTGCAGAAGGAA

CTCGCGGCAGGTCATCCACGGCCCGATGCAGCCTTTTCGGAAGTGACTTCGTCAACACCTTTGATGGGAGCATGTA

CAGCTTTGCGGGATACTGCAGTTACCTCCTGGCAGGGGGCTGCCAGAAACGCTCCTTCTCGATTATTGGGGACTTC

CAGAATGGCAAGAGAGTGAGCCTCTCCGTGTATCTTGGGGAATTTTTTGACATCCATTTGTTTGTCAATGGTACGG

TGACACAGGGGGACCAAAGAGTCTCCATGCCCTATGCCTCCAAAGGGCTGTATCTAGAAACTGAGGCTGGGTACT

ACAAGCTGTCCGGTGAGGCCTATGGCTTTGTGGCCAGGATCGATGGCAGCGGCAACTTTCAAGTCCTGCTGTCAGA

CAGATACTTCAACAAGACCTGCGGGCTGTGTGGCAACTTTAACATCTTTGCTGAAGATGACTTTATGACCCAAGAA

GGGACCTTGACCTCGGACCCTTATGACTTTGCCAACTCATGGGCTCTGAGCAGTGGAGAACAGTGGTGTGAACGG

GCATCTCCTCCCAGCAGCTCATGCAACATCTCCTCTGGGGAAATGCAGAAGGGCCTGTGGGAGCAGTGCCAGCTTC

TGAAGAGCACCTCGGTGTTTGCCCGCTGCCACCCTCTGGTGGACCCCGAGCCTTTTGTGGCCCTGTGTGAGAAGAC

TTTGTGTGAGTGTGCTGGGGGCTGGAGTGCGCCTGCCCTGCCCTCCTGGAGTACGCCCGGACCTGTGCCCAGGAG

GGAATGGTGCTGTACGGCTGGACCGACCACAGCGCGTGCAGCCCAGTGTGCCCTGCTGGTATGGAGTATAGGCAG

TGTGTGTCCCCTTGCGCCAGGACCTGCCAGAGCCTGCACATCAATGAAATGTGTCAGGAGCGATGCGTGGATGGCT

GCAGCTGCCCTGAGGGACAGCTCCTGGATGAAGGCCTCTGCGTGGAGAGCACCGAGTGTCCCTGCGTGCATTCCG

GAAAGCGCTACCCTCCCGGCACCTCCCTCTCGAGACTGCAACACCTGCATTTGCCGAAACAGCCAGTGGATCTG

CAGCAATGAAGAATGTCCAGGGGAGTGCCTTGTCACTGGTCAATCCCACTTCAAGAGCTTTGACAACAGATACTTC

ACCTTCAGTGGGATCTGCCAGTACCTGCTGGCCCGGGATTGCCAGGACCACTCCTTCTCCATTGTCATTGAGACTGT

CCAGTGTGCTGATGACCGCGACGCTGTGTGCACCCGCTCCGTCACCGTCCGGCTGCCTGGCCTGCACAACAGCCTT

-continued

```
GTGAAACTGAAGCATGGGGCAGGAGTTGCCATGGATGGCCAGGACATCCAGCTCCCCCTCCTGAAAGGTGACCTC

CGCATCCAGCATACAGTGACGGCCTCCGTGCGCCTCAGCTACGGGGAGGACCTGCAGATGGACTGGGATGGCCGC

GGGAGGCTGCTGGTGAAGCTGTCCCCCGTCTACGCCGGGAAGACCTGCGGCCTGTGTGGGAATTACAATGGCAAC

CAGGGCGACGACTTCCTTACCCCCTCTGGGCTGGCAGAGCCCCGGGTGGAGGACTTCGGGAACGCCTGGAAGCTG

CACGGGGACTGCCAGGACCTGCAGAAGCAGCACAGCGATCCCTGCGCCCTCAACCCGCGCATGACCAGGTTCTCC

GAGGAGGCGTGCGCGGTCCTGACGTCCCCCACATTCGAGGCCTGCCATCGTGCCGTCAGCCCGCTGCCCTACCTGC

GGAACTGCCGCTACGACGTGTGCTCCTGCTCGGACGGCCGCGAGTGCCTGTGCGGCGCCCTGGCCAGCTATGCCGC

GGCCTGCGCGGGGAGAGGCGTGCGCGTCGCGTGGCGCGAGCCAGGCCGCTGTGAGCTGAACTGCCCGAAAGGCC

AGGTGTACCTGCAGTGCGGGACCCCCTGCAACCTGACCTGCCGCTCTCTCTCTTACCCGGATGAGGAATGCAATGA

GGCCTGCCTGGAGGGCTGCTTCTGCCCCCCAGGGCTCTACATGGATGAGAGGGGGACTGCGTGCCCAAGGCCCA

GTGCCCCTGTTACTATGACGGTGAGATCTTCCAGCCAGAAGACATCTTCTCAGACCATCACACCATGTGCTACTGT

GAGGATGGCTTCATGCACTGTACCATGAGTGGAGTCCCCGGAAGCTTGCTGCCTGACGCTGTCCTCAGCAGTCCCC

TGTCTCATCGCAGCAAAAGGAGCCTATCCTGTCGGCCCCCCATGGTCAAGCTGGTGTGTCCCGCTGACAACCTGCG

GGCTGAAGGGCTCGAGTGTACCAAAACGTGCCAGAACTATGACCTGGAGTGCATGAGCATGGGCTGTGTCTCTGG

CTGCCCTCTGCCCCCGGGCATGGTCCGGCATGAGAACAGATGTGTGGCCCTGGAAAGGTGTCCCTGCTTCCATCAG

GGCAAGGAGTATGCCCCTGGAGAAACAGTGAAGATTGGCTGCAACACTTGTGTCTGTCGGGACCGGAAGTGGAAC

TGCACAGACCATGTGTGTGATGCCACGTGCTCCACGATCGGCATGGCCCACTACCTCACCTTCGACGGGCTCAAAT

ACCTGTTCCCCGGGGAGTGCCAGTACGTTCTGGTGCAGGATTACTGCGGCAGTAACCCTGGGACCTTTC

GGATCCTAGTGGGGAATAAGGGATGCAGCCACCCCTCAGTGAAATGCAAGAAACGGGTCACCATCCTGGTGGAGG

GAGGAGAGATTGAGCTGTTTGACGGGGAGGTGAATGTGAAGAGGCCCATGAAGGATGAGACTCACTTTGAGGTGG

TGGAGTCTGGCCGGTACATCATTCTGCTGCTGGGCAAAGCCCTCTCCGTGGTCTGGGACCGCCACCTGAGCATCTC

CGTGGTCCTGAAGCAGACATACCAGGAGAAAGTGTGTGGCCTGTGTGGGAATTTTGATGGCATCCAGAACAATGA

CCTCACCAGCAGCAACCTCCAAGTGGAGGAAGACCCTGTGGACTTTGGGAACTCCTGGAAAGTGAGCTCGCAGTG

TGCTGACACCAGAAAAGTGCCTCTGGACTCATCCCCTGCCACCTGCCATAACAACATCATGAAGCAGACGATGGT

GGATTCCTCCTGTAGAATCCTTACCAGTGACGTCTTCCAGGACTGCAACAAGCTGGTGGACCCCGAGCCATATCTG

GATGTCTGCATTTACGACACCTGCTCCTGTGAGTCCATTGGGGACTGCGCCTGCTTCTGCGACACCATTGCTGCCTA

TGCCCACGTGTGTGCCCAGCATGGCAAGGTGGTGACCTGGAGGACGGCCACATTGTGCCCCCAGAGCTGCGAGGA

GAGGAATCTCCGGGAGAACGGGTATGAGTGTGAGTGGCGCTATAACAGCTGTGCACCTGCCTGTCAAGTCACGTG

TCAGCACCCTGAGCCACTGGCCTGCCCTGTGCAGTGTGTGGAGGGCTGCCATGCCCACTGCCCTCCAGGGAAAATC

CTGGATGAGCTTTTGCAGACCTGCGTTGACCCTGAAGACTGTCCAGTGTGTGAGGTGGCTGGCCGGCGTTTTGCCT

CAGGAAAGAAAGTCACCTTGAATCCCAGTGACCCTGAGCACTGCCAGATTTGCCACTGTGATGTTGTCAACCTCAC

CTGTGAAGCCTGCCAGGAGCCGGGAGGCCTGGTGGTGCCTCCCACAGATGCCCCGGTGAGCCCCACCACTCTGTAT

GTGGAGGACATCTCGGAACCGCCGTTGCACGATTTCTACTGCAGCAGGCTACTGGACCTGGTCTTCCTGCTGGATG

GCTCCTCCAGGCTGTCCGAGGCTGAGTTTGAAGTGCTGAAGGCCTTTGTGGTGGACATGATGGAGCGGCTGCGCAT

CTCCCAGAAGTGGGTCCGCGTGGCCGTGGTGGAGTACCACGACGGCTCCCACGCCTACATCGGGCTCAAGGACCG

GAAGCGACCGTCAGAGCTGCGGCGCATTGCCAGCCAGGTGAAGTATGCGGGCAGCCAGGTGGCCTCCACCAGCGA

GGTCTTGAAATACACACTGTTCCAAATCTTCAGCAAGATCGACCGCCCTGAAGCCTCCCGCATCGCCCTGCTCCTG

ATGGCCAGCCAGGAGCCCCAACGGATGTCCCGGAACTTTGTCCGCTACGTCCAGGGCCTGAAGAAGAAGAAGGTC

ATTGTGATCCCGGTGGGCATTGGGCCCCATGCCAACCTCAAGCAGATCCGCCTCATCGAGAAGCAGGCCCCTGAG

AACAAGGCCTTCGTGCTGAGCAGTGTGGATGAGCTGGAGCAGCAAAGGGACGAGATCGTTAGCTACCTCTGTGAC

CTTGCCCCTGAAGCCCCTCCTCCTACTCTGCCCCCCCACATGGCACAAGTCACTGTGGGCCCGGGGCTCTTGGGGG
```

-continued

```
TTTCGACCCTGGGGCCCAAGAGGAACTCCATGGTTCTGGATGTGGCGTTCGTCCTGGAAGGATCGGACAAAATTGG
TGAAGCCGACTTCAACAGGAGCAAGGAGTTCATGGAGGAGGTGATTCAGCGGATGGATGTGGGCCAGGACAGCA
TCCACGTCACGGTGCTGCAGTACTCCTACATGGTGACCGTGGAGTACCCCTTCAGCGAGGCACAGTCCAAAGGGG
ACATCCTGCAGCGGGTGCGAGAGATCCGCTACCAGGGCGGCAACAGGACCAACACTGGGCTGGCCCTGCGGTACC
TCTCTGACCACAGCTTCTTGGTCAGCCAGGGTGACCGGGAGCAGGCGCCCAACCTGGTCTACATGGTCACCGGAA
ATCCTGCCTCTGATGAGATCAAGAGGCTGCCTGGAGACATCCAGGTGGTGCCCATTGGAGTGGGCCCTAATGCCA
ACGTGCAGGAGCTGGAGAGGATTGGCTGGCCCAATGCCCCTATCCTCATCCAGGACTTTGAGACGCTCCCCCGAG
AGGCTCCTGACCTGGTGCTGCAGAGGTGCTGCTCCGGAGAGGGGCTGCAGATCCCCACCCTCTCCCCTGCACCTGA
CTGCAGCCAGCCCCTGGACGTGATCCTTCTCCTGGATGGCTCCTCCAGTTTCCCAGCTTCTTATTTTGATGAAATGA
AGAGTTTCGCCAAGGCTTTCATTTCAAAAGCCAATATAGGGCCTCGTCTCACTCAGGTGTCAGTGCTGCAGTATGG
AAGCATCACCACCATTGACGTGCCATGGAACGTGGTCCCGGAGAAAGCCCATTTGCTGAGCCTTGTGGACGTCATG
CAGCGGGAGGGAGGCCCCAGCCAAATCGGGGATGCCTTGGGCTTTGCTGTGCGATACTTGACTTCAGAAATGCAT
GGTGCCAGGCCGGGAGCCTCAAAGGCGGTGGTCATCCTGGTCACGGACGTCTCTGTGGATTCAGTGGATGCAGCA
GCTGATGCCGCCAGGTCCAACAGAGTGACAGTGTTCCCTATTGGAATTGGAGATCGCTACGATGCAGCCCAGCTAC
GGATCTTGGCAGGCCCAGCAGGCGACTCCAACGTGGTGAAGCTCCAGCGAATCGAAGACCTCCCTACCATGGTCA
CCTTGGGCAATTCCTTCCTCCACAAACTGTGCTCTGGAGAGCCTGAGTGCAACGACATCACTGCCAGGCTGCAGTA
TGTCAAGGTGGGAAGCTGTAAGTCTGAAGTAGAGGTGGATATCCACTACTGCCAGGGCAAATGTGCCAGCAAAGC
CATGTACTCCATTGACATCAACGATGTGCAGGACCAGTGCTCCTGCTGCTCTCCGACACGGACGGAGCCCATGCAG
GTGGCCCTGCACTGCACCAATGGCTCTGTTGTGTACCATGAGGTTCTCAATGCCATGGAGTGCAAATGCTCCCCCA
GGAAGTGCAGCAAGTGA
```

BRIEF DESCRIPTION OF THE FIGURES

Reference is made to a number of drawings in which.

The invention will now be further described by way of reference to the following Examples which are present for the purposes of reference only and are not to be construed as being limiting on the invention.

EXAMPLES

Figure 1:
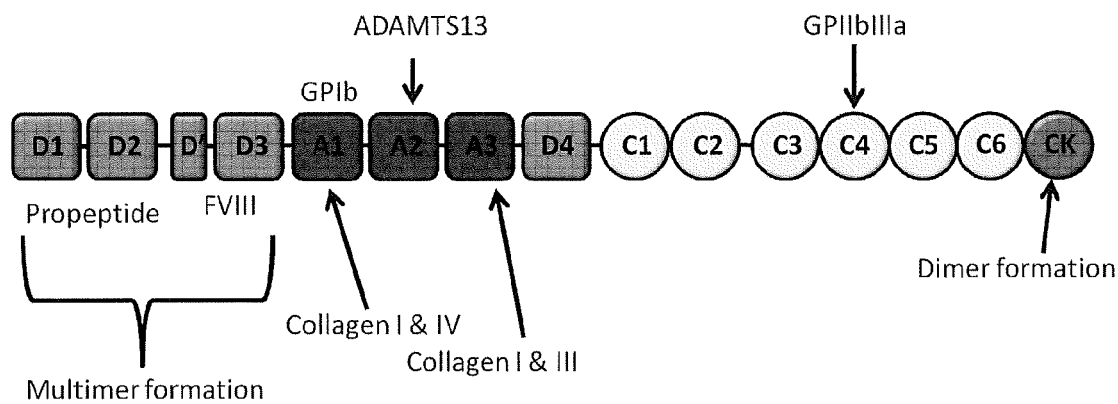
FIG. 1 shows the domain structure of VWF. Full length VWF comprises 2813 amino acids (8439 bp cDNA, excluding the stop codon shown in SEQ ID NO: 2 above) organised in functional domains as shown. The CK domain is required for dimer formation in the ER, while the propeptide and D'D3 domains form multimers in the Golgi body.
Figure 2:
FIG. 2 shows the domain structure of the truncated VWF variant of the present invention, which lacks the D4 and C1-C6 domains.
Figure 3A:
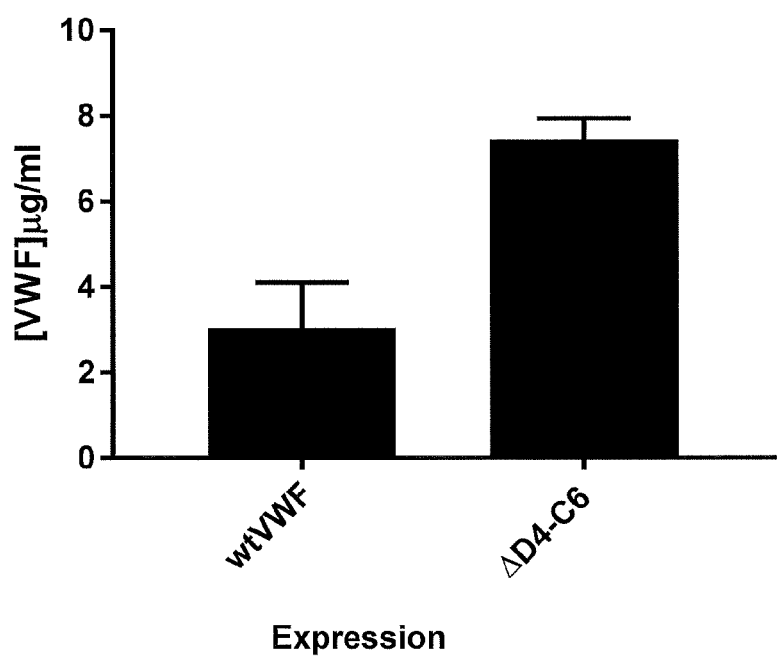
FIGS. 3A, 3B, and 3C show VWF mediated platelet capture to type III collagen at 1500 s$^{-1}$.
Figure 3B:
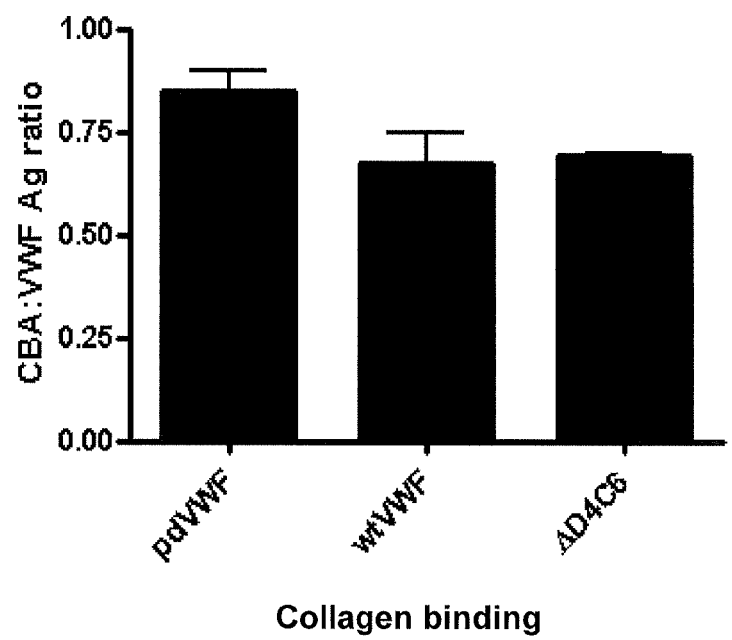
Figure 3C:
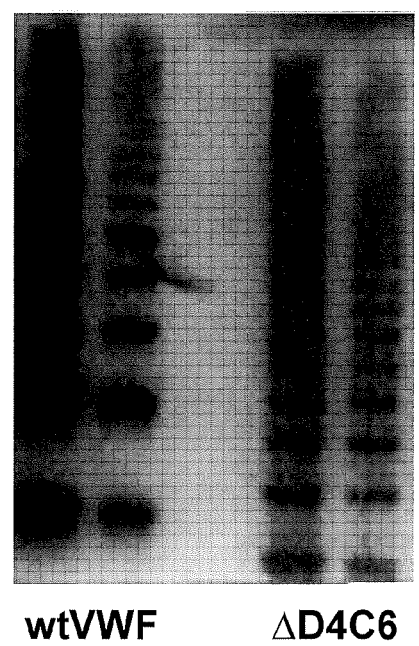

Example 1—Expression and Collagen Binding (A) HEK293T cells were transiently transfected with expression vectors for either full length wild type VWF or VWF-ΔD4C6 and media and cell lysate samples collected 3 days post transfection and VWF expressed assed by VWF ELISA. The media to lysate ratios are similar indicating normal expression. The results are shown in FIG. 3A. (B) Recombinant VWF expressed as in (A) was incubated with plates coated with human type III collagen and bound VWF detected with polyclonal anti-VWF antibodies. Data was calculated as the VWF antigen to collagen binding ratio and compared to VWF derived from normal human plasma. As can be seen from FIG. 3B, a similar ratio is observed between all samples indicating normal collagen binding, indicative of normal multimerisation. (C) The multimeric content of recombinant full length VWF or VWF-ΔD4C6 was determined by electrophoresis in 1% agarose gels followed by western blotting and probing with anti-VWF-HRP antibodies. The results are shown in FIG. 3C. As can be seen from the Figure, the VWF-ΔD4C6 variant forms a normal range of multimers comparable to full length recombinant VWF.

Example 2—VWF-ΔD4C6 has Normal Platelet Capture Under Shear Stress

Figure 4A:
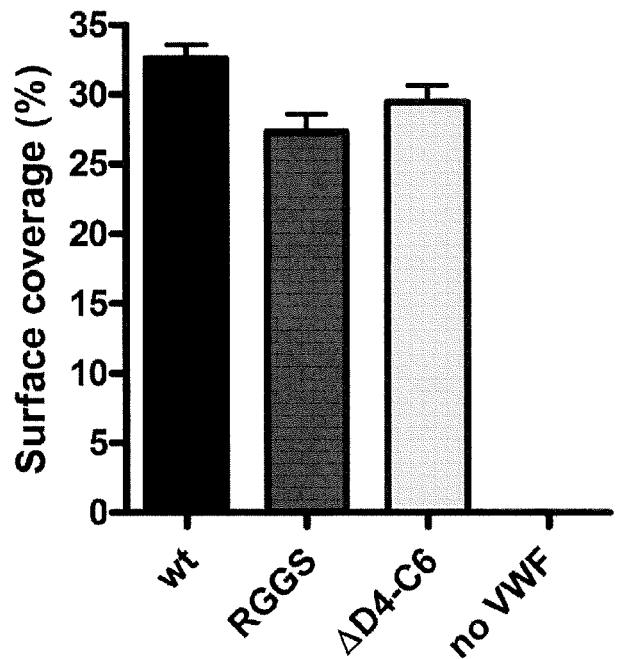
FIGS. 4A and 4B show that the truncated VWF variant of the present invention has normal platelet capture under shear stress.

FIG. 4A—Flow chamber slides were coated directly with either wild type VWF, the deletion variant or a VWF variant lacking an intact RGD sequence and surfaces were perfused with plasma free blood at 1500 s$^{-1}$ for 5 mins. The immobilised VWF molecules showed no difference in their ability to capture platelets.

Flow chamber slides were coated with human type III collagen and perfused at high shear stress (1500 s$^{-1}$) with plasma free blood supplemented with either wtVWF, VWF-ΔD4C6, or a VWF mutant lacking an intact RGDS (SEQ ID NO: 32) sequence (mutated to RGGS (SEQ ID NO: 33)).

Figure 4B:
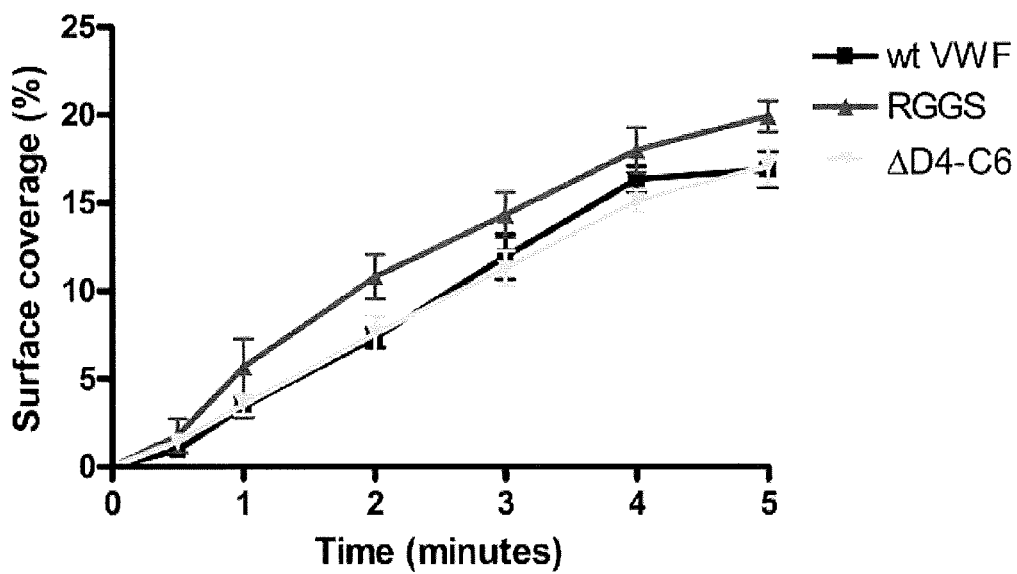

Plasma free blood is comprised of washed red blood cells, labelled platelets and HEPES/Tyrode's buffer to give a normal platelet count and haematocrit. Without the addition of soluble VWF no platelet capture to collagen at high shear stress is observed. Platelets were washed and activation in part inhibited by the addition of PGE1 and apyrase. The results are shown in FIG. 4B.

This data demonstrates that deletion of the D4-C6 region of VWF does not affect the ability of the molecule to bind to collagen under flow or capture platelets, at least under the tested shear rate.

Example 3—VWF-ΔD4C6—Normal Clearance in Mice

Figure 5:
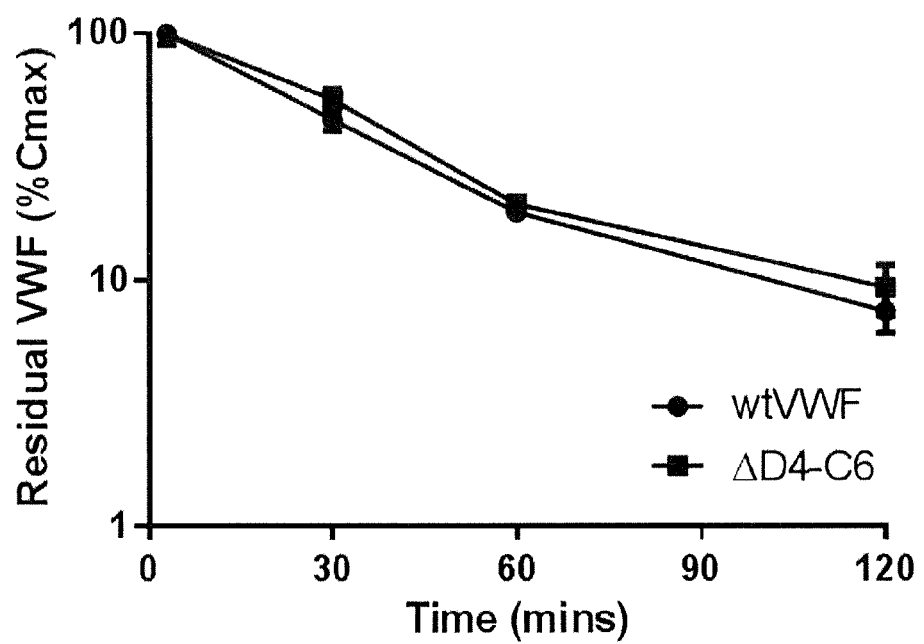
FIG. 5 shows that the truncated VWF variant of the present invention demonstrates normal clearance in mice.

Full length recombinant VWF or VWF-ΔD4C6 protein was injected into the tail vein of VWF deficient mice and at designated time points plasma samples obtained for the mice to determine VWF recovery. The results are shown in FIG. 5. As can be seen from the Figure, both proteins were recovered to a similar extent at all times indicating a similar clearance profile.

---

The invention claimed is:

1. A von Willebrand factor (vWF) polypeptide lacking amino acid residues 1875-2720 (D4-C6 domains) of the full length vWF protein (SEQ ID NO: 1) comprising:
   (a) the amino acid sequence consisting of SEQ ID NO: 3, or
   (b) an amino acid sequence with at least 70% sequence identity to SEQ ID NO: 3;
wherein the amino acid sequence retains the CK domain (SEQ ID NO: 31) or a CK domain (SEQ ID NO: 31) with up to ten amino acid deletions.

2. The polypeptide according to claim 1, wherein the polypeptide is fused to a heterologous peptide, polypeptide or protein.

3. A method of treating von Willebrand disease or haemophilia in a subject comprising administering to the subject the polypeptide according to claim 1.

4. A pharmaceutical composition comprising a polypeptide according to claim 1 and one or more pharmaceutically acceptable carriers, diluents or excipients.

5. A pharmaceutical composition according to claim 4, further comprising at least one second therapeutically active agent.

6. A pharmaceutical composition according to claim 5, wherein said therapeutically active agent is factor VIII, desmopressin, or an antifibrinolytic agent.

7. A pharmaceutical composition according to claim 6 wherein the antifibrinolytic agent is tranexamic acid.

8. A method for the treatment of von Willebrand disease or haemophilia comprising administering to a subject in need thereof a pharmaceutical composition according to claim 4.

9. A nucleic acid comprising a nucleotide sequence encoding a polypeptide according to claim 1.

10. The nucleic acid according to claim 9, wherein the nucleotide sequence lacks nucleotides 5623 to 8160 of SEQ ID NO: 2.

11. The nucleic acid according to claim 9, wherein the nucleotide sequence comprises or consists of the cDNA sequence of SEQ ID NO: 4, or a sequence having at least 70% identity thereto.

12. A method of treating von Willebrand disease or haemophilia in a subject comprising administering to the subject the nucleic acid according to claim 9.

13. A pharmaceutical composition comprising a nucleic acid according to claim 9 and one or more pharmaceutically acceptable carriers, diluents or excipients.

14. A construct comprising the nucleic acid according to claim 9.

15. A method for the treatment of von Willebrand disease or haemophilia comprising administering to a subject in need thereof a construct according to claim 14.

16. A vector comprising a nucleic acid according to claim 9.

17. A method for the treatment of von Willebrand disease or haemophilia comprising administering to a subject in need thereof a vector according to claim 16.

18. A cell comprising a nucleic acid according to claim 9.

19. A method for the treatment of von Willebrand disease or haemophilia comprising administering to a subject in need thereof a cell according to claim 18.

* * * * *

SEQUENCE LISTING

<160> NUMBER OF SEQ ID NOS: 33

<210> SEQ ID NO 1
<211> LENGTH: 2813
<212> TYPE: PRT
<213> ORGANISM: Artificial Sequence
<220> FEATURE:
<223> OTHER INFORMATION: Synthetic construct

<400> SEQUENCE: 1

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
```

-continued

```
                275                 280                 285
    Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
    305                 310                 315                 320

Cys Gln Glu Arg Cys Val Asp Gly Cys Ser Cys Pro Glu Gly Gln Leu
                    325                 330                 335

Leu Asp Glu Gly Leu Cys Val Glu Ser Thr Glu Cys Pro Cys Val His
                    340                 345                 350

Ser Gly Lys Arg Tyr Pro Pro Gly Thr Ser Leu Ser Arg Asp Cys Asn
                    355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
    385                 390                 395                 400

Asn Arg Tyr Phe Thr Phe Ser Gly Ile Cys Gln Tyr Leu Leu Ala Arg
                    405                 410                 415

Asp Cys Gln Asp His Ser Phe Ser Ile Val Ile Glu Thr Val Gln Cys
                    420                 425                 430

Ala Asp Asp Arg Asp Ala Val Cys Thr Arg Ser Val Thr Val Arg Leu
                    435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
    465                 470                 475                 480

Arg Ile Gln His Thr Val Thr Ala Ser Val Arg Leu Ser Tyr Gly Glu
                    485                 490                 495

Asp Leu Gln Met Asp Trp Asp Gly Arg Gly Arg Leu Leu Val Lys Leu
                    500                 505                 510

Ser Pro Val Tyr Ala Gly Lys Thr Cys Gly Leu Cys Gly Asn Tyr Asn
                    515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
    545                 550                 555                 560

Asp Leu Gln Lys Gln His Ser Asp Pro Cys Ala Leu Asn Pro Arg Met
                    565                 570                 575

Thr Arg Phe Ser Glu Glu Ala Cys Ala Val Leu Thr Ser Pro Thr Phe
                    580                 585                 590

Glu Ala Cys His Arg Ala Val Ser Pro Leu Pro Tyr Leu Arg Asn Cys
                    595                 600                 605

Arg Tyr Asp Val Cys Ser Cys Ser Asp Gly Arg Glu Cys Leu Cys Gly
            610                 615                 620

Ala Leu Ala Ser Tyr Ala Ala Ala Cys Ala Gly Arg Gly Val Arg Val
    625                 630                 635                 640

Ala Trp Arg Glu Pro Gly Arg Cys Glu Leu Asn Cys Pro Lys Gly Gln
                    645                 650                 655

Val Tyr Leu Gln Cys Gly Thr Pro Cys Asn Leu Thr Cys Arg Ser Leu
                    660                 665                 670

Ser Tyr Pro Asp Glu Glu Cys Asn Glu Ala Cys Leu Glu Gly Cys Phe
                    675                 680                 685

Cys Pro Pro Gly Leu Tyr Met Asp Glu Arg Gly Asp Cys Val Pro Lys
    690                 695                 700
```

```
Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
            725                 730                 735

His Cys Thr Met Ser Gly Val Pro Gly Ser Leu Leu Pro Asp Ala Val
        740                 745                 750

Leu Ser Ser Pro Leu Ser His Arg Ser Lys Arg Ser Leu Ser Cys Arg
    755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
            805                 810                 815

His Glu Asn Arg Cys Val Ala Leu Glu Arg Cys Pro Cys Phe His Gln
        820                 825                 830

Gly Lys Glu Tyr Ala Pro Gly Glu Thr Val Lys Ile Gly Cys Asn Thr
    835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
            885                 890                 895

Tyr Cys Gly Ser Asn Pro Gly Thr Phe Arg Ile Leu Val Gly Asn Lys
        900                 905                 910

Gly Cys Ser His Pro Ser Val Lys Cys Lys Arg Val Thr Ile Leu
    915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
            965                 970                 975

His Leu Ser Ile Ser Val Val Leu Lys Gln Thr Tyr Gln Glu Lys Val
        980                 985                 990

Cys Gly Leu Cys Gly Asn Phe Asp Gly Ile Gln Asn Asn Asp Leu Thr
    995                 1000                1005

Ser Ser Asn Leu Gln Val Glu Glu Asp Pro Val Asp Phe Gly Asn
    1010                1015                1020

Ser Trp Lys Val Ser Ser Gln Cys Ala Asp Thr Arg Lys Val Pro
    1025                1030                1035

Leu Asp Ser Ser Pro Ala Thr Cys His Asn Asn Ile Met Lys Gln
    1040                1045                1050

Thr Met Val Asp Ser Ser Cys Arg Ile Leu Thr Ser Asp Val Phe
    1055                1060                1065

Gln Asp Cys Asn Lys Leu Val Asp Pro Glu Pro Tyr Leu Asp Val
    1070                1075                1080

Cys Ile Tyr Asp Thr Cys Ser Cys Glu Ser Ile Gly Asp Cys Ala
    1085                1090                1095

Cys Phe Cys Asp Thr Ile Ala Ala Tyr Ala His Val Cys Ala Gln
    1100                1105                1110
```

```
His Gly Lys Val Val Thr Trp Arg Thr Ala Thr Leu Cys Pro Gln
1115                1120                1125

Ser Cys Glu Glu Arg Asn Leu Arg Glu Asn Gly Tyr Glu Cys Glu
1130                1135                1140

Trp Arg Tyr Asn Ser Cys Ala Pro Ala Cys Gln Val Thr Cys Gln
1145                1150                1155

His Pro Glu Pro Leu Ala Cys Pro Val Gln Cys Val Glu Gly Cys
1160                1165                1170

His Ala His Cys Pro Pro Gly Lys Ile Leu Asp Glu Leu Leu Gln
1175                1180                1185

Thr Cys Val Asp Pro Glu Asp Cys Pro Val Cys Glu Val Ala Gly
1190                1195                1200

Arg Arg Phe Ala Ser Gly Lys Lys Val Thr Leu Asn Pro Ser Asp
1205                1210                1215

Pro Glu His Cys Gln Ile Cys His Cys Asp Val Val Asn Leu Thr
1220                1225                1230

Cys Glu Ala Cys Gln Glu Pro Gly Gly Leu Val Val Pro Pro Thr
1235                1240                1245

Asp Ala Pro Val Ser Pro Thr Thr Leu Tyr Val Glu Asp Ile Ser
1250                1255                1260

Glu Pro Pro Leu His Asp Phe Tyr Cys Ser Arg Leu Leu Asp Leu
1265                1270                1275

Val Phe Leu Leu Asp Gly Ser Ser Arg Leu Ser Glu Ala Glu Phe
1280                1285                1290

Glu Val Leu Lys Ala Phe Val Val Asp Met Met Glu Arg Leu Arg
1295                1300                1305

Ile Ser Gln Lys Trp Val Arg Val Ala Val Val Glu Tyr His Asp
1310                1315                1320

Gly Ser His Ala Tyr Ile Gly Leu Lys Asp Arg Lys Arg Pro Ser
1325                1330                1335

Glu Leu Arg Arg Ile Ala Ser Gln Val Lys Tyr Ala Gly Ser Gln
1340                1345                1350

Val Ala Ser Thr Ser Glu Val Leu Lys Tyr Thr Leu Phe Gln Ile
1355                1360                1365

Phe Ser Lys Ile Asp Arg Pro Glu Ala Ser Arg Ile Ala Leu Leu
1370                1375                1380

Leu Met Ala Ser Gln Glu Pro Gln Arg Met Ser Arg Asn Phe Val
1385                1390                1395

Arg Tyr Val Gln Gly Leu Lys Lys Lys Lys Val Ile Val Ile Pro
1400                1405                1410

Val Gly Ile Gly Pro His Ala Asn Leu Lys Gln Ile Arg Leu Ile
1415                1420                1425

Glu Lys Gln Ala Pro Glu Asn Lys Ala Phe Val Leu Ser Ser Val
1430                1435                1440

Asp Glu Leu Glu Gln Gln Arg Asp Glu Ile Val Ser Tyr Leu Cys
1445                1450                1455

Asp Leu Ala Pro Glu Ala Pro Pro Pro Thr Leu Pro Pro His Met
1460                1465                1470

Ala Gln Val Thr Val Gly Pro Gly Leu Leu Gly Val Ser Thr Leu
1475                1480                1485

Gly Pro Lys Arg Asn Ser Met Val Leu Asp Val Ala Phe Val Leu
1490                1495                1500

Glu Gly Ser Asp Lys Ile Gly Glu Ala Asp Phe Asn Arg Ser Lys
```

```
              1505                1510                1515

Glu  Phe  Met  Glu  Glu  Val  Ile  Gln  Arg  Met  Asp  Val  Gly  Gln  Asp
              1520                1525                1530

Ser  Ile  His  Val  Thr  Val  Leu  Gln  Tyr  Ser  Tyr  Met  Val  Thr  Val
              1535                1540                1545

Glu  Tyr  Pro  Phe  Ser  Glu  Ala  Gln  Ser  Lys  Gly  Asp  Ile  Leu  Gln
              1550                1555                1560

Arg  Val  Arg  Glu  Ile  Arg  Tyr  Gln  Gly  Gly  Asn  Arg  Thr  Asn  Thr
              1565                1570                1575

Gly  Leu  Ala  Leu  Arg  Tyr  Leu  Ser  Asp  His  Ser  Phe  Leu  Val  Ser
              1580                1585                1590

Gln  Gly  Asp  Arg  Glu  Gln  Ala  Pro  Asn  Leu  Val  Tyr  Met  Val  Thr
              1595                1600                1605

Gly  Asn  Pro  Ala  Ser  Asp  Glu  Ile  Lys  Arg  Leu  Pro  Gly  Asp  Ile
              1610                1615                1620

Gln  Val  Val  Pro  Ile  Gly  Val  Gly  Pro  Asn  Ala  Asn  Val  Gln  Glu
              1625                1630                1635

Leu  Glu  Arg  Ile  Gly  Trp  Pro  Asn  Ala  Pro  Ile  Leu  Ile  Gln  Asp
              1640                1645                1650

Phe  Glu  Thr  Leu  Pro  Arg  Glu  Ala  Pro  Asp  Leu  Val  Leu  Gln  Arg
              1655                1660                1665

Cys  Cys  Ser  Gly  Glu  Gly  Leu  Gln  Ile  Pro  Thr  Leu  Ser  Pro  Ala
              1670                1675                1680

Pro  Asp  Cys  Ser  Gln  Pro  Leu  Asp  Val  Ile  Leu  Leu  Leu  Asp  Gly
              1685                1690                1695

Ser  Ser  Ser  Phe  Pro  Ala  Ser  Tyr  Phe  Asp  Glu  Met  Lys  Ser  Phe
              1700                1705                1710

Ala  Lys  Ala  Phe  Ile  Ser  Lys  Ala  Asn  Ile  Gly  Pro  Arg  Leu  Thr
              1715                1720                1725

Gln  Val  Ser  Val  Leu  Gln  Tyr  Gly  Ser  Ile  Thr  Thr  Ile  Asp  Val
              1730                1735                1740

Pro  Trp  Asn  Val  Val  Pro  Glu  Lys  Ala  His  Leu  Leu  Ser  Leu  Val
              1745                1750                1755

Asp  Val  Met  Gln  Arg  Glu  Gly  Gly  Pro  Ser  Gln  Ile  Gly  Asp  Ala
              1760                1765                1770

Leu  Gly  Phe  Ala  Val  Arg  Tyr  Leu  Thr  Ser  Glu  Met  His  Gly  Ala
              1775                1780                1785

Arg  Pro  Gly  Ala  Ser  Lys  Ala  Val  Val  Ile  Leu  Val  Thr  Asp  Val
              1790                1795                1800

Ser  Val  Asp  Ser  Val  Asp  Ala  Ala  Ala  Asp  Ala  Ala  Arg  Ser  Asn
              1805                1810                1815

Arg  Val  Thr  Val  Phe  Pro  Ile  Gly  Ile  Gly  Asp  Arg  Tyr  Asp  Ala
              1820                1825                1830

Ala  Gln  Leu  Arg  Ile  Leu  Ala  Gly  Pro  Ala  Gly  Asp  Ser  Asn  Val
              1835                1840                1845

Val  Lys  Leu  Gln  Arg  Ile  Glu  Asp  Leu  Pro  Thr  Met  Val  Thr  Leu
              1850                1855                1860

Gly  Asn  Ser  Phe  Leu  His  Lys  Leu  Cys  Ser  Gly  Phe  Val  Arg  Ile
              1865                1870                1875

Cys  Met  Asp  Glu  Asp  Gly  Asn  Glu  Lys  Arg  Pro  Gly  Asp  Val  Trp
              1880                1885                1890

Thr  Leu  Pro  Asp  Gln  Cys  His  Thr  Val  Thr  Cys  Gln  Pro  Asp  Gly
              1895                1900                1905
```

-continued

Gln Thr Leu Leu Lys Ser His Arg Val Asn Cys Asp Arg Gly Leu
    1910            1915            1920

Arg Pro Ser Cys Pro Asn Ser Gln Ser Pro Val Lys Val Glu Glu
    1925            1930            1935

Thr Cys Gly Cys Arg Trp Thr Cys Pro Cys Val Cys Thr Gly Ser
    1940            1945            1950

Ser Thr Arg His Ile Val Thr Phe Asp Gly Gln Asn Phe Lys Leu
    1955            1960            1965

Thr Gly Ser Cys Ser Tyr Val Leu Phe Gln Asn Lys Glu Gln Asp
    1970            1975            1980

Leu Glu Val Ile Leu His Asn Gly Ala Cys Ser Pro Gly Ala Arg
    1985            1990            1995

Gln Gly Cys Met Lys Ser Ile Glu Val Lys His Ser Ala Leu Ser
    2000            2005            2010

Val Glu Leu His Ser Asp Met Glu Val Thr Val Asn Gly Arg Leu
    2015            2020            2025

Val Ser Val Pro Tyr Val Gly Gly Asn Met Glu Val Asn Val Tyr
    2030            2035            2040

Gly Ala Ile Met His Glu Val Arg Phe Asn His Leu Gly His Ile
    2045            2050            2055

Phe Thr Phe Thr Pro Gln Asn Asn Glu Phe Gln Leu Gln Leu Ser
    2060            2065            2070

Pro Lys Thr Phe Ala Ser Lys Thr Tyr Gly Leu Cys Gly Ile Cys
    2075            2080            2085

Asp Glu Asn Gly Ala Asn Asp Phe Met Leu Arg Asp Gly Thr Val
    2090            2095            2100

Thr Thr Asp Trp Lys Thr Leu Val Gln Glu Trp Thr Val Gln Arg
    2105            2110            2115

Pro Gly Gln Thr Cys Gln Pro Ile Leu Glu Glu Gln Cys Leu Val
    2120            2125            2130

Pro Asp Ser Ser His Cys Gln Val Leu Leu Leu Pro Leu Phe Ala
    2135            2140            2145

Glu Cys His Lys Val Leu Ala Pro Ala Thr Phe Tyr Ala Ile Cys
    2150            2155            2160

Gln Gln Asp Ser Cys His Gln Glu Gln Val Cys Glu Val Ile Ala
    2165            2170            2175

Ser Tyr Ala His Leu Cys Arg Thr Asn Gly Val Cys Val Asp Trp
    2180            2185            2190

Arg Thr Pro Asp Phe Cys Ala Met Ser Cys Pro Pro Ser Leu Val
    2195            2200            2205

Tyr Asn His Cys Glu His Gly Cys Pro Arg His Cys Asp Gly Asn
    2210            2215            2220

Val Ser Ser Cys Gly Asp His Pro Ser Glu Gly Cys Phe Cys Pro
    2225            2230            2235

Pro Asp Lys Val Met Leu Glu Gly Ser Cys Val Pro Glu Glu Ala
    2240            2245            2250

Cys Thr Gln Cys Ile Gly Glu Asp Gly Val Gln His Gln Phe Leu
    2255            2260            2265

Glu Ala Trp Val Pro Asp His Gln Pro Cys Gln Ile Cys Thr Cys
    2270            2275            2280

Leu Ser Gly Arg Lys Val Asn Cys Thr Thr Gln Pro Cys Pro Thr
    2285            2290            2295

-continued

```
Ala Lys Ala Pro Thr Cys Gly Leu Cys Glu Val Ala Arg Leu Arg
    2300                2305                2310

Gln Asn Ala Asp Gln Cys Cys Pro Glu Tyr Glu Cys Val Cys Asp
    2315                2320                2325

Pro Val Ser Cys Asp Leu Pro Pro Val Pro His Cys Glu Arg Gly
    2330                2335                2340

Leu Gln Pro Thr Leu Thr Asn Pro Gly Glu Cys Arg Pro Asn Phe
    2345                2350                2355

Thr Cys Ala Cys Arg Lys Glu Glu Cys Lys Arg Val Ser Pro Pro
    2360                2365                2370

Ser Cys Pro Pro His Arg Leu Pro Thr Leu Arg Lys Thr Gln Cys
    2375                2380                2385

Cys Asp Glu Tyr Glu Cys Ala Cys Asn Cys Val Asn Ser Thr Val
    2390                2395                2400

Ser Cys Pro Leu Gly Tyr Leu Ala Ser Thr Ala Thr Asn Asp Cys
    2405                2410                2415

Gly Cys Thr Thr Thr Thr Cys Leu Pro Asp Lys Val Cys Val His
    2420                2425                2430

Arg Ser Thr Ile Tyr Pro Val Gly Gln Phe Trp Glu Glu Gly Cys
    2435                2440                2445

Asp Val Cys Thr Cys Thr Asp Met Glu Asp Ala Val Met Gly Leu
    2450                2455                2460

Arg Val Ala Gln Cys Ser Gln Lys Pro Cys Glu Asp Ser Cys Arg
    2465                2470                2475

Ser Gly Phe Thr Tyr Val Leu His Glu Gly Glu Cys Cys Gly Arg
    2480                2485                2490

Cys Leu Pro Ser Ala Cys Glu Val Val Thr Gly Ser Pro Arg Gly
    2495                2500                2505

Asp Ser Gln Ser Ser Trp Lys Ser Val Gly Ser Gln Trp Ala Ser
    2510                2515                2520

Pro Glu Asn Pro Cys Leu Ile Asn Glu Cys Val Arg Val Lys Glu
    2525                2530                2535

Glu Val Phe Ile Gln Gln Arg Asn Val Ser Cys Pro Gln Leu Glu
    2540                2545                2550

Val Pro Val Cys Pro Ser Gly Phe Gln Leu Ser Cys Lys Thr Ser
    2555                2560                2565

Ala Cys Cys Pro Ser Cys Arg Cys Glu Arg Met Glu Ala Cys Met
    2570                2575                2580

Leu Asn Gly Thr Val Ile Gly Pro Gly Lys Thr Val Met Ile Asp
    2585                2590                2595

Val Cys Thr Thr Cys Arg Cys Met Val Gln Val Gly Val Ile Ser
    2600                2605                2610

Gly Phe Lys Leu Glu Cys Arg Lys Thr Thr Cys Asn Pro Cys Pro
    2615                2620                2625

Leu Gly Tyr Lys Glu Glu Asn Asn Thr Gly Glu Cys Cys Gly Arg
    2630                2635                2640

Cys Leu Pro Thr Ala Cys Thr Ile Gln Leu Arg Gly Gly Gln Ile
    2645                2650                2655

Met Thr Leu Lys Arg Asp Glu Thr Leu Gln Asp Gly Cys Asp Thr
    2660                2665                2670

His Phe Cys Lys Val Asn Glu Arg Gly Glu Tyr Phe Trp Glu Lys
    2675                2680                2685

Arg Val Thr Gly Cys Pro Pro Phe Asp Glu His Lys Cys Leu Ala
```

```
                         2690                2695                2700
Glu Gly Gly Lys Ile Met Lys Ile Pro Gly Thr Cys Cys Asp Thr
    2705                2710                2715
Cys Glu Glu Pro Glu Cys Asn Asp Ile Thr Ala Arg Leu Gln Tyr
    2720                2725                2730
Val Lys Val Gly Ser Cys Lys Ser Glu Val Glu Val Asp Ile His
    2735                2740                2745
Tyr Cys Gln Gly Lys Cys Ala Ser Lys Ala Met Tyr Ser Ile Asp
    2750                2755                2760
Ile Asn Asp Val Gln Asp Gln Cys Ser Cys Cys Ser Pro Thr Arg
    2765                2770                2775
Thr Glu Pro Met Gln Val Ala Leu His Cys Thr Asn Gly Ser Val
    2780                2785                2790
Val Tyr His Glu Val Leu Asn Ala Met Glu Cys Lys Cys Ser Pro
    2795                2800                2805
Arg Lys Cys Ser Lys
    2810

<210> SEQ ID NO 2
<211> LENGTH: 8442
<212> TYPE: DNA
<213> ORGANISM: Artificial Sequence
<220> FEATURE:
<223> OTHER INFORMATION: Synthetic construct

<400> SEQUENCE: 2
atgattcctg ccagatttgc cggggtgctg cttgctctgg ccctcatttt gccagggacc      60
ctttgtgcag aaggaactcg cggcaggtca tccacggccc gatgcagcct tttcggaagt     120
gacttcgtca acacctttga tgggagcatg tacagctttg cgggatactg cagttacctc     180
ctggcagggg gctgccagaa cgctccttc tcgattattg gggacttcca gaatggcaag     240
agagtgagcc tctccgtgta tcttggggaa ttttttgaca tccatttgtt tgtcaatggt     300
accgtgacac aggggggacca aagagtctcc atgccctatg cctccaaagg gctgtatcta     360
gaaactgagg ctgggtacta caagctgtcc ggtgaggcct atggctttgt ggccaggatc     420
gatggcagcg gcaactttca gtcctgctg tcagacagat acttcaacaa gacctgcggg     480
ctgtgtggca ctttaacat cttttgctgaa gatgacttta tgacccaaga agggaccttg     540
acctcggacc cttatgactt tgccaactca tgggctctga gcagtggaga acagtggtgt     600
gaacgggcat ctcctcccag cagctcatgc aacatctcct ctggggaaat gcagaagggc     660
ctgtgggagc agtgccagct tctgaagagc acctcggtgt ttgcccgctg ccaccctctg     720
gtggaccccg agccttttgt ggcccctgtgt gagaagactt tgtgtgagtg tgctgggggg     780
ctggagtgcg cctgccctgc cctcctggag tacgcccgga cctgtgccca ggagggaatg     840
gtgctgtacg gctggaccga ccacagcgcg tgcagcccag tgtgccctgc tggtatggag     900
tataggcagt gtgtgtcccc ttgcgccagg acctgccaga gctgcacat caatgaaatg     960
tgtcaggagc gatgcgtgga tggctgcagc tgccctgagg acagctcct ggatgaaggc    1020
ctctgcgtgg agagcaccga gtgtccctgc gtgcattccg aaagcgcta ccctcccggc    1080
acctccctct ctcgagactg caacacctgc atttgccgaa acagccagtg gatctgcagc    1140
aatgaagaat gtccagggga gtgccttgtc actggtcaat cccacttcaa gagctttgac    1200
aacagatact tcaccttcag tgggatctgc cagtacctgc tggcccggga ttgccaggac    1260
cactccttct ccattgtcat tgagactgtc cagtgtgctg atgaccgcga cgctgtgtgc    1320
```

```
acccgctccg tcaccgtccg gctgcctggc ctgcacaaca gccttgtgaa actgaagcat   1380
ggggcaggag ttgccatgga tggccaggac atccagctcc ccctcctgaa aggtgacctc   1440
cgcatccagc atacagtgac ggcctccgtg cgcctcagct acggggagga cctgcagatg   1500
gactgggatg gccgcgggag gctgctggtg aagctgtccc ccgtctacgc cgggaagacc   1560
tgcggcctgt gtgggaatta caatggcaac cagggcgacg acttccttac cccctctggg   1620
ctggcagagc ccgggtgga ggacttcggg aacgcctgga agctgcacgg ggactgccag   1680
gacctgcaga agcagcacag cgatccctgc gccctcaacc cgcgcatgac caggttctcc   1740
gaggaggcgt gcgcggtcct gacgtccccc acattcgagg cctgccatcg tgccgtcagc   1800
ccgctgccct acctgcggaa ctgccgctac gacgtgtgct cctgctcgga cggccgcgag   1860
tgcctgtgcg gcgccctggc cagctatgcc gcggcctgcg cggggagagg cgtgcgcgtc   1920
gcgtggcgcg agccaggccg ctgtgagctg aactgcccga aaggccaggt gtacctgcag   1980
tgcgggaccc cctgcaacct gacctgccgc tctctctctt acccggatga ggaatgcaat   2040
gaggcctgcc tggagggctg cttctgcccc ccagggctct acatggatga gaggggggac   2100
tgcgtgccca aggcccagtg cccctgttac tatgacggtg agatcttcca gccagaagac   2160
atcttctcag accatcacac catgtgctac tgtgaggatg gcttcatgca ctgtaccatg   2220
agtggagtcc ccggaagctt gctgcctgac gctgtcctca gcagtcccct gtctcatcgc   2280
agcaaaagga gcctatcctg tcggcccccc atggtcaagc tggtgtgtcc cgctgacaac   2340
ctgcgggctg aagggctcga gtgtaccaaa acgtgccaga actatgacct ggagtgcatg   2400
agcatgggct gtgtctctgg ctgcctctgc cccccgggca tggtccggca tgagaacaga   2460
tgtgtggccc tggaaaggtg tccctgcttc catcagggca aggagtatgc ccctggagaa   2520
acagtgaaga ttggctgcaa cacttgtgtc tgtcgggacc ggaagtggaa ctgcacagac   2580
catgtgtgtg atgccacgtg ctccacgatc ggcatggccc actacctcac cttcgacggg   2640
ctcaaatacc tgttccccgg ggagtgccag tacgttctgg tgcaggatta ctgcggcagt   2700
aaccctggga cctttcggat cctagtgggg aataagggat gcagccaccc ctcagtgaaa   2760
tgcaagaaac gggtcaccat cctggtggag ggaggagaga ttgagctgtt tgacggggag   2820
gtgaatgtga agaggcccat gaaggatgag actcactttg aggtggtgga gtctggccgg   2880
tacatcattc tgctgctggg caaagccctc tccgtggtct gggaccgcca cctgagcatc   2940
tccgtggtcc tgaagcagac ataccaggag aaagtgtgtg gcctgtgtgg aattttgat   3000 ggcatccaga acaatgacct caccagcagc aacctccaag tggaggaaga ccctgtggac   3060
tttgggaact cctggaaagt gagctcgcag tgtgctgaca ccagaaaagt gcctctggac   3120
tcatcccctg ccacctgcca taacaacatc atgaagcaga cgatggtgga ttcctcctgt   3180
agaatcctta ccagtgacgt cttccaggac tgcaacaagc tggtggaccc cgagccatat   3240
ctggatgtct gcatttacga cacctgctcc tgtgagtcca ttgggactg cgcctgcttc   3300 tgcgacacca ttgctgccta tgcccacgtg tgtgcccagc atggcaaggt ggtgacctgg   3360
aggacggcca cattgtgccc ccagagctgc gaggagagga tctccgggga aacgggtat   3420 gagtgtgagt ggcgctataa cagctgtgca cctgcctgtc aagtcacgtg tcagcaccct   3480
gagccactgg cctgccctgt gcagtgtgtg gagggctgcc atgcccactg ccctccaggg   3540
aaaatcctgg atgagctttt gcagacctgc gttgaccctg aagactgtcc agtgtgtgag   3600
gtggctggcc ggcgttttgc ctcaggaaag aaagtcacct tgaatcccag tgaccctgag   3660
```

```
cactgccaga tttgccactg tgatgttgtc aacctcacct gtgaagcctg ccaggagccg    3720
ggaggcctgg tggtgcctcc cacagatgcc ccggtgagcc ccaccactct gtatgtggag    3780
gacatctcgg aaccgccgtt gcacgatttc tactgcagca ggctactgga cctggtcttc    3840
ctgctggatg gctcctccag gctgtccgag gctgagtttg aagtgctgaa ggcctttgtg    3900
gtggacatga tggagcggct gcgcatctcc cagaagtggg tccgcgtggc cgtggtggag    3960
taccacgacg gctcccacgc ctacatcggg ctcaaggacc ggaagcgacc gtcagagctg    4020
cggcgcattg ccagccaggt gaagtatgcg ggcagccagg tggcctccac cagcgaggtc    4080
ttgaaataca cactgttcca aatcttcagc aagatcgacc gccctgaagc ctcccgcatc    4140
gccctgctcc tgatggccag ccaggagccc aacggatgt cccggaactt tgtccgctac    4200
gtccagggcc tgaagaagaa gaaggtcatt gtgatcccgg tgggcattgg gcccatgcc    4260 aacctcaagc agatccgcct catcgagaag caggcccctg agaacaaggc cttcgtgctg    4320
agcagtgtgg atgagctgga gcagcaaagg gacgagatcg ttagctacct ctgtgacctt    4380
gcccctgaag cccctcctcc tactctgccc cccacatgg cacaagtcac tgtgggcccg    4440
gggctcttgg gggtttcgac cctggggccc aagaggaact ccatggttct ggatgtggcg    4500
ttcgtcctgg aaggatcgga caaaattggt gaagccgact tcaacaggag caaggagttc    4560
atggaggagg tgattcagcg gatggatgtg ggccaggaca gcatccacgt cacggtgctg    4620
cagtactcct acatggtgac cgtggagtac cccttcagcg aggcacagtc caaaggggac    4680
atcctgcagc gggtgcgaga gatccgctac cagggcggca acaggaccaa cactgggctg    4740
gccctgcggt acctctctga ccacagcttc ttggtcagcc agggtgaccg ggagcaggcg    4800
cccaacctgg tctacatggt caccggaaat cctgcctctg atgagatcaa gaggctgcct    4860
ggagacatcc agtggtgcc cattggagtg ggccctaatg ccaacgtgca ggagctggag    4920
aggattggct ggcccaatgc ccctatcctc atccaggact ttgagacgct ccccgagag    4980 gctcctgacc tggtgctgca gaggtgctgc tccggagagg ggctgcagat ccccacccct    5040
tcccctgcac ctgactgcag ccagcccctg gacgtgatcc ttctcctgga tggctcctcc    5100
agtttcccag cttcttattt tgatgaaatg aagagtttcg ccaaggcttt catttcaaaa    5160
gccaatatag ggcctcgtct cactcaggtg tcagtgctgc agtatggaag catcaccacc    5220
attgacgtgc catggaacgt ggtcccggag aaagcccatt tgctgagcct tgtgacgtc    5280 atgcagcggg agggaggccc cagccaaatc ggggatgcct gggctttgc tgtgcgatac    5340 ttgacttcag aaatgcatgg tgccaggccg ggagcctcaa aggcggtggt catcctggtc    5400
acggacgtct ctgtggattc agtggatgca gcagctgatg ccgccaggtc caacagagtg    5460
acagtgttcc ctattggaat tggagatcgc tacgatgcag cccagctacg gatcttggca    5520
ggcccagcag gcgactccaa cgtggtgaag ctccagcgaa tcgaagacct ccctaccatg    5580
gtcaccttgg gcaattcctt cctccacaaa ctgtgctctg gatttgttag gatttgcatg    5640
gatgaggatg ggaatgagaa gaggcccggg gacgtctgga ccttgccaga ccagtgccac    5700
accgtgactt gccagccaga tggccagacc ttgctgaaga gtcatcgggt caactgtgac    5760
cgggggctga ggccttcgtg ccctaacagc cagtcccctg ttaaagtgga agagacctgt    5820
ggctgccgct ggacctgccc ctgcgtgtgc acaggcagct ccactcggca catcgtgacc    5880
tttgatgggc agaatttcaa gctgactggc agctgttctt atgtcctatt tcaaaacaag    5940
gagcaggacc tggaggtgat tctccataat ggtgcctgca gccctggagc aaggcagggc    6000
tgcatgaaat ccatcgaggt gaagcacagt gccctctccg tcgagctgca cagtgacatg    6060
```

```
gaggtgacgg tgaatgggag actggtctct gttccttacg tgggtgggaa catggaagtc    6120
aacgtttatg gtgccatcat gcatgaggtc agattcaatc accttggtca catcttcaca    6180
ttcactccac aaaacaatga gttccaactg cagctcagcc ccaagacttt tgcttcaaag    6240
acgtatggtc tgtgtgggat ctgtgatgag aacggagcca atgacttcat gctgagggat    6300
ggcacagtca ccacagactg gaaaacactt gttcaggaat ggactgtgca gcggccaggg    6360
cagacgtgcc agcccatcct ggaggagcag tgtcttgtcc ccgacagctc ccactgccag    6420
gtcctcctct taccactgtt tgctgaatgc acaaggtcc tggctccagc cacattctat    6480
gccatctgcc agcaggacag ttgccaccag gagcaagtgt gtgaggtgat cgcctcttat    6540
gcccacctct gtcggaccaa cggggtctgc gttgactgga ggacacctga tttctgtgct    6600
atgtcatgcc caccatctct ggtctacaac cactgtgagc atggctgtcc ccggcactgt    6660
gatggcaacg tgagctcctg tggggaccat ccctccgaag gctgtttctg ccctccagat    6720
aaagtcatgt tggaaggcag ctgtgtccct gaagaggcct gcactcagtg cattggtgag    6780
gatggagtcc agcaccagtt cctggaagcc tgggtcccgg accaccagcc ctgtcagatc    6840
tgcacatgcc tcagcgggcg gaaggtcaac tgcacaacgc agccctgccc cacggccaaa    6900
gctcccacgt gtggcctgtg tgaagtagcc cgcctccgcc agaatgcaga ccagtgctgc    6960
cccgagtatg agtgtgtgtg tgacccagtg agctgtgacc tgccccagt gcctcactgt    7020 gaacgtggcc tccagcccac actgaccaac cctggcgagt gcagacccaa cttcacctgc    7080
gcctgcagga aggaggagtg caaaagagtg tccccaccct cctgcccccc gcaccgtttg    7140 cccaccccttc ggaagaccca gtgctgtgat gagtatgagt gtgcctgcaa ctgtgtcaac    7200
tccacagtga gctgtcccct tgggtacttg gcctcaaccg ccaccaatga ctgtggctgt    7260
accacaacca cctgccttcc cgacaaggtg tgtgtccacc gaagcaccat ctaccctgtg    7320
ggccagttct gggaggaggg ctgcgatgtg tgcacctgca ccgacatgga ggatgccgtg    7380
atgggcctcc gcgtggccca gtgctcccag aagccctgtg aggacagctg tcggtcgggc    7440
ttcacttacg ttctgcatga aggcgagtgc tgtggaaggt gcctgccatc tgcctgtgag    7500
gtggtgactg gctcaccgcg gggggactcc cagtcttcct ggaagagtgt cggctcccag    7560
tgggcctccc cggagaaccc ctgcctcatc aatgagtgtg tccgagtgaa ggaggaggtc    7620
tttatacaac aaaggaacgt ctcctgcccc cagctggagg tccctgtctg ccctcgggc    7680 tttcagctga gctgtaagac ctcagcgtgc tgcccaagct gtcgctgtga gcgcatggag    7740
gcctgcatgc tcaatggcac tgtcattggg cccgggaaga ctgtgatgat cgatgtgtgc    7800
acgacctgcc gctgcatggt gcaggtgggg gtcatctctg gattcaagct ggagtgcagg    7860
aagaccacct gcaaccctg ccccctgggt tacaaggaag aaaataacac aggtgaatgt    7920
tgtgggagat gtttgcctac ggcttgcacc attcagctaa gaggaggaca gatcatgaca    7980
ctgaagcgtg atgagacgct ccaggatggc tgtgatactc acttctgcaa ggtcaatgag    8040
agaggagagt acttctggga gaagagggtc acaggctgcc cacccttga tgaacacaag    8100 tgtctggctg agggaggtaa aattatgaaa attccaggca cctgctgtga cacatgtgag    8160
gagcctgagt gcaacgacat cactgccagg ctgcagtatg tcaaggtggg aagctgtaag    8220
tctgaagtag aggtggatat ccactactgc cagggcaaat gtgccagcaa agccatgtac    8280
tccattgaca tcaacgatgt gcaggaccag tgctcctgct gctctccgac acggacggag    8340
cccatgcagg tggccctgca ctgcaccaat ggctctgttg tgtaccatga ggttctcaat    8400
```

```
gccatggagt gcaaatgctc ccccaggaag tgcagcaagt ga                    8442
```

<210> SEQ ID NO 3
<211> LENGTH: 1967
<212> TYPE: PRT
<213> ORGANISM: Artificial Sequence
<220> FEATURE:
<223> OTHER INFORMATION: Synthetic construct

<400> SEQUENCE: 3

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
```

```
                355                 360                 365
Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
    610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
    690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
    770                 775                 780
```

-continued

```
Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
        835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
        915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                 1005

Ser Ser  Asn Leu Gln Val Glu  Glu Asp Pro Val Asp  Phe Gly Asn
    1010                 1015                 1020

Ser Trp  Lys Val Ser Ser Gln  Cys Ala Asp Thr Arg  Lys Val Pro
    1025                 1030                 1035

Leu Asp  Ser Ser Pro Ala Thr  Cys His Asn Asn Ile  Met Lys Gln
    1040                 1045                 1050

Thr Met  Val Asp Ser Ser Cys  Arg Ile Leu Thr Ser  Asp Val Phe
    1055                 1060                 1065

Gln Asp  Cys Asn Lys Leu Val  Asp Pro Glu Pro Tyr  Leu Asp Val
    1070                 1075                 1080

Cys Ile  Tyr Asp Thr Cys Ser  Cys Glu Ser Ile Gly  Asp Cys Ala
    1085                 1090                 1095

Cys Phe  Cys Asp Thr Ile Ala  Ala Tyr Ala His Val  Cys Ala Gln
    1100                 1105                 1110

His Gly  Lys Val Val Thr Trp  Arg Thr Ala Thr Leu  Cys Pro Gln
    1115                 1120                 1125

Ser Cys  Glu Glu Arg Asn Leu  Arg Glu Asn Gly Tyr  Glu Cys Glu
    1130                 1135                 1140

Trp Arg  Tyr Asn Ser Cys Ala  Pro Ala Cys Gln Val  Thr Cys Gln
    1145                 1150                 1155

His Pro  Glu Pro Leu Ala Cys  Pro Val Gln Cys Val  Glu Gly Cys
    1160                 1165                 1170

His Ala  His Cys Pro Pro Gly  Lys Ile Leu Asp Glu  Leu Leu Gln
    1175                 1180                 1185
```

```
Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Gly Gly Leu Val Val Pro Pro Thr
    1235                1240                1245

Asp Ala Pro Val Ser Pro Thr Thr Leu Tyr Val Glu Asp Ile Ser
    1250                1255                1260

Glu Pro Pro Leu His Asp Phe Tyr Cys Ser Arg Leu Leu Asp Leu
    1265                1270                1275

Val Phe Leu Leu Asp Gly Ser Ser Arg Leu Ser Glu Ala Glu Phe
    1280                1285                1290

Glu Val Leu Lys Ala Phe Val Val Asp Met Met Glu Arg Leu Arg
    1295                1300                1305

Ile Ser Gln Lys Trp Val Arg Val Ala Val Val Glu Tyr His Asp
    1310                1315                1320

Gly Ser His Ala Tyr Ile Gly Leu Lys Asp Arg Lys Arg Pro Ser
    1325                1330                1335

Glu Leu Arg Arg Ile Ala Ser Gln Val Lys Tyr Ala Gly Ser Gln
    1340                1345                1350

Val Ala Ser Thr Ser Glu Val Leu Lys Tyr Thr Leu Phe Gln Ile
    1355                1360                1365

Phe Ser Lys Ile Asp Arg Pro Glu Ala Ser Arg Ile Ala Leu Leu
    1370                1375                1380

Leu Met Ala Ser Gln Glu Pro Gln Arg Met Ser Arg Asn Phe Val
    1385                1390                1395

Arg Tyr Val Gln Gly Leu Lys Lys Lys Val Ile Val Ile Pro
    1400                1405                1410

Val Gly Ile Gly Pro His Ala Asn Leu Lys Gln Ile Arg Leu Ile
    1415                1420                1425

Glu Lys Gln Ala Pro Glu Asn Lys Ala Phe Val Leu Ser Ser Val
    1430                1435                1440

Asp Glu Leu Glu Gln Gln Arg Asp Glu Ile Val Ser Tyr Leu Cys
    1445                1450                1455

Asp Leu Ala Pro Glu Ala Pro Pro Pro Thr Leu Pro Pro His Met
    1460                1465                1470

Ala Gln Val Thr Val Gly Pro Gly Leu Leu Gly Val Ser Thr Leu
    1475                1480                1485

Gly Pro Lys Arg Asn Ser Met Val Leu Asp Val Ala Phe Val Leu
    1490                1495                1500

Glu Gly Ser Asp Lys Ile Gly Glu Ala Asp Phe Asn Arg Ser Lys
    1505                1510                1515

Glu Phe Met Glu Glu Val Ile Gln Arg Met Asp Val Gly Gln Asp
    1520                1525                1530

Ser Ile His Val Thr Val Leu Gln Tyr Ser Tyr Met Val Thr Val
    1535                1540                1545

Glu Tyr Pro Phe Ser Glu Ala Gln Ser Lys Gly Asp Ile Leu Gln
    1550                1555                1560

Arg Val Arg Glu Ile Arg Tyr Gln Gly Gly Asn Arg Thr Asn Thr
    1565                1570                1575

Gly Leu Ala Leu Arg Tyr Leu Ser Asp His Ser Phe Leu Val Ser
```

```
               1580                1585                1590
Gln Gly Asp Arg Glu Gln Ala Pro Asn Leu Val Tyr Met Val Thr
    1595                1600                1605
Gly Asn Pro Ala Ser Asp Glu Ile Lys Arg Leu Pro Gly Asp Ile
    1610                1615                1620
Gln Val Val Pro Ile Gly Val Gly Pro Asn Ala Asn Val Gln Glu
    1625                1630                1635
Leu Glu Arg Ile Gly Trp Pro Asn Ala Pro Ile Leu Ile Gln Asp
    1640                1645                1650
Phe Glu Thr Leu Pro Arg Glu Ala Pro Asp Leu Val Leu Gln Arg
    1655                1660                1665
Cys Cys Ser Gly Glu Gly Leu Gln Ile Pro Thr Leu Ser Pro Ala
    1670                1675                1680
Pro Asp Cys Ser Gln Pro Leu Asp Val Ile Leu Leu Leu Asp Gly
    1685                1690                1695
Ser Ser Ser Phe Pro Ala Ser Tyr Phe Asp Glu Met Lys Ser Phe
    1700                1705                1710
Ala Lys Ala Phe Ile Ser Lys Ala Asn Ile Gly Pro Arg Leu Thr
    1715                1720                1725
Gln Val Ser Val Leu Gln Tyr Gly Ser Ile Thr Thr Ile Asp Val
    1730                1735                1740
Pro Trp Asn Val Val Pro Glu Lys Ala His Leu Leu Ser Leu Val
    1745                1750                1755
Asp Val Met Gln Arg Glu Gly Gly Pro Ser Gln Ile Gly Asp Ala
    1760                1765                1770
Leu Gly Phe Ala Val Arg Tyr Leu Thr Ser Glu Met His Gly Ala
    1775                1780                1785
Arg Pro Gly Ala Ser Lys Ala Val Val Ile Leu Val Thr Asp Val
    1790                1795                1800
Ser Val Asp Ser Val Asp Ala Ala Ala Asp Ala Ala Arg Ser Asn
    1805                1810                1815
Arg Val Thr Val Phe Pro Ile Gly Ile Gly Asp Arg Tyr Asp Ala
    1820                1825                1830
Ala Gln Leu Arg Ile Leu Ala Gly Pro Ala Gly Asp Ser Asn Val
    1835                1840                1845
Val Lys Leu Gln Arg Ile Glu Asp Leu Pro Thr Met Val Thr Leu
    1850                1855                1860
Gly Asn Ser Phe Leu His Lys Leu Cys Ser Gly Glu Pro Glu Cys
    1865                1870                1875
Asn Asp Ile Thr Ala Arg Leu Gln Tyr Val Lys Val Gly Ser Cys
    1880                1885                1890
Lys Ser Glu Val Glu Val Asp Ile His Tyr Cys Gln Gly Lys Cys
    1895                1900                1905
Ala Ser Lys Ala Met Tyr Ser Ile Asp Ile Asn Asp Val Gln Asp
    1910                1915                1920
Gln Cys Ser Cys Cys Ser Pro Thr Arg Thr Glu Pro Met Gln Val
    1925                1930                1935
Ala Leu His Cys Thr Asn Gly Ser Val Val Tyr His Glu Val Leu
    1940                1945                1950
Asn Ala Met Glu Cys Lys Cys Ser Pro Arg Lys Cys Ser Lys
    1955                1960                1965

<210> SEQ ID NO 4
```

<211> LENGTH: 5904
<212> TYPE: DNA
<213> ORGANISM: Artificial Sequence
<220> FEATURE:
<223> OTHER INFORMATION: Synthetic construct

<400> SEQUENCE: 4

| | |
|---|---:|
| atgattcctg ccagatttgc cggggtgctg cttgctctgg ccctcatttt gccagggacc | 60 |
| ctttgtgcag aaggaactcg cggcaggtca tccacggccc gatgcagcct tttcggaagt | 120 |
| gacttcgtca acacctttga tgggagcatg tacagctttg cgggatactg cagttacctc | 180 |
| ctggcagggg gctgccagaa acgctccttc tcgattattg gggacttcca gaatggcaag | 240 |
| agagtgagcc tctccgtgta tcttggggaa ttttttgaca tccatttgtt tgtcaatggt | 300 |
| acggtgacac aggggaccaa aagagtctcc atgccctatg cctccaaagg ctgtatctca | 360 |
| gaaactgagg ctgggtacta caagctgtcc ggtgaggcct atggctttgt ggccaggatc | 420 |
| gatggcagcg gcaactttca gtcctgctgt cagacagat acttcaacaa gacctgcggg | 480 |
| ctgtgtggca actttaacat ctttgctgaa gatgacttta tgacccaaga agggaccttg | 540 |
| acctcggacc cttatgactt tgccaactca tgggctctga gcagtggaga acagtggtgt | 600 |
| gaacgggcat ctcctcccag cagctcatgc aacatctcct ctggggaaat gcagaagggc | 660 |
| ctgtgggagc agtgccagct tctgaagagc acctcggtgt tgcccgctg ccaccctctg | 720 |
| gtggaccccg agcttttgt ggccctgtgt gagaagactt tgtgtgagtg tgctgggggg | 780 |
| ctggagtgcg cctgccctgc cctcctggag tacgcccgga cctgtgccca ggagggaatg | 840 |
| gtgctgtacg gctggaccga ccacagcgcg tgcagcccag tgccctgc tggtatggag | 900 |
| tataggcagt gtgtgtcccc ttgcgccagg acctgccaga gcctgcacat caatgaaatg | 960 |
| tgtcaggagc gatgcgtgga tggctgcagc tgccctgagg acagctcct ggatgaaggc | 1020 |
| ctctgcgtgg agagcaccga gtgtcctgc gtgcattccg aaagcgcta ccctcccggc | 1080 |
| acctccctct ctcgagactg caacacctgc atttgccgaa acagccagtg gatctgcagc | 1140 |
| aatgaagaat gtccagggga gtgccttgtc actggtcaat cccacttcaa gagctttgac | 1200 |
| aacagatact tcaccttcag tgggatctgc cagtacctgc tggcccggga ttgccaggac | 1260 |
| cactccttct ccattgtcat tgagactgtc cagtgtgctg atgaccgcga cgctgtgtgc | 1320 |
| acccgctccg tcaccgtccg gctgcctggc ctgcacaaca gccttgtgaa actgaagcat | 1380 |
| ggggcaggag ttgccatgga tggccaggac atccagctcc ccctcctgaa aggtgacctc | 1440 |
| cgcatccagc atacagtgac ggcctccgtg cgcctcagct acgggagga cctgcagatg | 1500 |
| gactgggatg gccgcggag gctgctggtg aagctgtccc ccgtctacgc cgggaagacc | 1560 |
| tgcggcctgt gtgggaatta caatggcaac cagggcgacg acttccttac cccctctggg | 1620 |
| ctggcagagc ccggggtgga ggacttcggg aacgcctgga agctgcacgg ggactgccag | 1680 |
| gacctgcaga agcagcacag cgatcccgc gccctcaacc gcgcatgac caggttctcc | 1740 |
| gaggaggcgt gcgcggtcct gacgtccccc acattcgagg cctgccatcg tgccgtcagc | 1800 |
| ccgctgccct acctgcggaa ctgccgctac gacgtgtgct cctgctcgga cggccgcgag | 1860 |
| tgcctgtgcg gcgccctggc cagctatgcc gcggcctgcg cggggagagg cgtgcgcgtc | 1920 |
| gcgtggcgcg agccaggccg ctgtgagctg aactgcccga aaggccaggt gtacctgcag | 1980 |
| tgcgggaccc cctgcaacct gacctgccgc tctctctctt acccggatga ggaatgcaat | 2040 |
| gaggcctgcc tggagggctg cttctgcccc ccagggctct acatggatga gggggggac | 2100 |
| tgcgtgccca aggcccagtg cccctgttac tatgacggtg agatcttcca gccagaagac | 2160 |

```
atcttctcag accatcacac catgtgctac tgtgaggatg gcttcatgca ctgtaccatg    2220
agtggagtcc ccggaagctt gctgcctgac gctgtcctca gcagtcccct gtctcatcgc    2280
agcaaaagga gcctatcctg tcggcccccc atggtcaagc tggtgtgtcc cgctgacaac    2340
ctgcgggctg aagggctcga gtgtaccaaa acgtgccaga actatgacct ggagtgcatg    2400
agcatgggct gtgtctctgg ctgcctctgc cccccgggca tggtccggca tgagaacaga    2460
tgtgtggccc tggaaaggtg tccctgcttc catcagggca aggagtatgc ccctggagaa    2520
acagtgaaga ttggctgcaa cacttgtgtc tgtcgggacc ggaagtggaa ctgcacagac    2580
catgtgtgtg atgccacgtg ctccacgatc ggcatggccc actacctcac cttcgacggg    2640
ctcaaatacc tgttccccgg ggagtgccag tacgttctgg tgcaggatta ctgcggcagt    2700
aaccctggga cctttcggat cctagtgggg aataagggat gcagccaccc ctcagtgaaa    2760
tgcaagaaac gggtcaccat cctggtggag ggaggagaga ttgagctgtt tgacggggag    2820
gtgaatgtga agaggcccat gaaggatgag actcactttg aggtggtgga gtctggccgg    2880
tacatcattc tgctgctggg caaagccctc tccgtggtct gggaccgcca cctgagcatc    2940
tccgtggtcc tgaagcagac ataccaggag aaagtgtgtg gcctgtgtgg gaattttgat    3000
ggcatccaga acaatgacct caccagcagc aacctccaag tggaggaaga ccctgtggac    3060
tttgggaact cctggaaagt gagctcgcag tgtgctgaca ccagaaaagt gcctctggac    3120
tcatcccctg ccacctgcca taacaacatc atgaagcaga cgatggtgga ttcctcctgt    3180
agaatcctta ccagtgacgt cttccaggac tgcaacaagc tggtggaccc cgagccatat    3240
ctggatgtct gcatttacga cacctgctcc tgtgagtcca ttggggactg cgcctgcttc    3300
tgcgacacca ttgctgccta tgcccacgtg tgtgcccagc atggcaaggt ggtgacctgg    3360
aggacggcca cattgtgccc ccagagctgc gaggagagga atctccggga gaacgggtat    3420
gagtgtgagt ggcgctataa cagctgtgca cctgcctgtc aagtcacgtg tcagcaccct    3480
gagccactgg cctgccctgt gcagtgtgtg gagggctgcc atgcccactg ccctccaggg    3540
aaaatcctgg atgagctttt gcagacctgc gttgaccctg aagactgtcc agtgtgtgag    3600
gtggctggcc ggcgttttgc ctcaggaaag aaagtcacct tgaatcccag tgaccctgag    3660
cactgccaga tttgccactg tgatgttgtc aacctcacct gtgaagcctg ccaggagccg    3720
ggaggcctgc tggtgcctcc cacagatgcc ccggtgagcc ccaccactct gtatgtggag    3780
gacatctcgg aaccgccgtt gcacgatttc tactgcagca ggctactgga cctggtcttc    3840
ctgctggatg ctcctccag gctgtccgag gctgagtttg aagtgctgaa ggcctttgtg    3900
gtggacatga tggagcggct gcgcatctcc cagaagtggg tccgcgtggc cgtggtggag    3960
taccacgacg gctcccacgc ctacatcggg ctcaaggacc ggaagcgacc gtcagagctg    4020
cggcgcattg ccagccaggt gaagtatgcg ggcagccagg tggcctccac cagcgaggtc    4080
ttgaaataca cactgttcca aatcttcagc aagatcgacc gccctgaagc ctcccgcatc    4140
gccctgctcc tgatggccag ccaggagccc caacggatgt cccggaactt tgtccgctac    4200
gtccagggcc tgaagaagaa gaaggtcatt gtgatcccgg tgggcattgg gccccatgcc    4260
aacctcaagc agatccgcct catcgagaag caggcccctg agaacaaggc cttcgtgctg    4320
agcagtgtgg atgagctgga gcagcaaagg gacgagatcg ttagctacct ctgtgacctt    4380 gccccctgaag cccctcctcc tactctgccc cccacatgg cacaagtcac tgtgggcccg    4440
gggctcttgg gggtttcgac cctggggccc aagaggaact ccatggttct ggatgtggcg    4500
```

```
ttcgtcctgg aaggatcgga caaaattggt gaagccgact tcaacaggag caaggagttc    4560
atggaggagg tgattcagcg gatggatgtg ggccaggaca gcatccacgt cacggtgctg    4620
cagtactcct acatggtgac cgtggagtac cccttcagcg aggcacagtc caaaggggac    4680
atcctgcagc gggtgcgaga gatccgctac cagggcggca acaggaccaa cactgggctg    4740
gccctgcggt acctctctga ccacagcttc ttggtcagcc agggtgaccg ggagcaggcg    4800
cccaacctgg tctacatggt caccggaaat cctgcctctg atgagatcaa gaggctgcct    4860
ggagacatcc aggtggtgcc cattggagtg ggccctaatg ccaacgtgca ggagctggag    4920
aggattggct ggcccaatgc ccctatcctc atccaggact tgagacgct  ccccgagag    4980 gctcctgacc tggtgctgca gaggtgctgc tccggagagg ggctgcagat ccccacccctc   5040 tccctgcac ctgactgcag ccagcccctg acgtgatcc ttctcctgga tggctcctcc     5100
agtttcccag cttcttattt tgatgaaatg aagagtttcg ccaaggcttt catttcaaaa    5160
gccaatatag ggcctcgtct cactcaggtg tcagtgctgc agtatggaag catcaccacc    5220
attgacgtgc catggaacgt ggtcccggag aaagcccatt tgctgagcct tgtggacgtc    5280
atgcagcggg agggaggccc cagccaaatc ggggatgcct tgggctttgc tgtgcgatac    5340
ttgacttcag aaatgcatgg tgccaggccg ggagcctcaa aggcggtggt catcctggtc    5400
acggacgtct ctgtggattc agtggatgca gcagctgatg ccgccaggtc caacagagtg    5460
acagtgttcc ctattggaat tggagatcgc tacgatgcag cccagctacg atcttggca    5520 ggcccagcag gcgactccaa cgtggtgaag ctccagcgaa tcgaagacct ccctaccatg    5580
gtcaccttgg gcaattcctt cctccacaaa ctgtgctctg gagagcctga gtgcaacgac    5640
atcactgcca ggctgcagta tgtcaaggtg ggaagctgta agtctgaagt agaggtggat    5700
atccactact gccagggcaa atgtgccagc aaagccatgt actccattga catcaacgat    5760
gtgcaggacc agtgctcctg ctgctctccg acacggacgg agcccatgca ggtggccctg    5820
cactgcacca atggctctgt tgtgtaccat gaggttctca atgccatgga gtgcaaatgc    5880
tcccccagga agtgcagcaa gtga                                          5904
```

<210> SEQ ID NO 5
<211> LENGTH: 22
<212> TYPE: PRT
<213> ORGANISM: Artificial Sequence
<220> FEATURE:
<223> OTHER INFORMATION: Synthetic construct

<400> SEQUENCE: 5

Met Ile Pro Ala Arg Phe Ala Gly Val Leu Leu Ala Leu Ala Leu Ile
1               5                   10                  15

Leu Pro Gly Thr Leu Cys
            20

<210> SEQ ID NO 6
<211> LENGTH: 741
<212> TYPE: PRT
<213> ORGANISM: Artificial Sequence
<220> FEATURE:
<223> OTHER INFORMATION: Synthetic construct

<400> SEQUENCE: 6

Ala Glu Gly Thr Arg Gly Arg Ser Ser Thr Ala Arg Cys Ser Leu Phe
1               5                   10                  15

Gly Ser Asp Phe Val Asn Thr Phe Asp Gly Ser Met Tyr Ser Phe Ala
            20                  25                  30

```
Gly Tyr Cys Ser Tyr Leu Leu Ala Gly Gly Cys Gln Lys Arg Ser Phe
        35                  40                  45

Ser Ile Ile Gly Asp Phe Gln Asn Gly Lys Arg Val Ser Leu Ser Val
    50                  55                  60

Tyr Leu Gly Glu Phe Phe Asp Ile His Leu Phe Val Asn Gly Thr Val
65                  70                  75                  80

Thr Gln Gly Asp Gln Arg Val Ser Met Pro Tyr Ala Ser Lys Gly Leu
                85                  90                  95

Tyr Leu Glu Thr Glu Ala Gly Tyr Tyr Lys Leu Ser Gly Glu Ala Tyr
            100                 105                 110

Gly Phe Val Ala Arg Ile Asp Gly Ser Gly Asn Phe Gln Val Leu Leu
            115                 120                 125

Ser Asp Arg Tyr Phe Asn Lys Thr Cys Gly Leu Cys Gly Asn Phe Asn
    130                 135                 140

Ile Phe Ala Glu Asp Asp Phe Met Thr Gln Glu Gly Thr Leu Thr Ser
145                 150                 155                 160

Asp Pro Tyr Asp Phe Ala Asn Ser Trp Ala Leu Ser Ser Gly Glu Gln
                165                 170                 175

Trp Cys Glu Arg Ala Ser Pro Pro Ser Ser Ser Cys Asn Ile Ser Ser
            180                 185                 190

Gly Glu Met Gln Lys Gly Leu Trp Glu Gln Cys Gln Leu Leu Lys Ser
            195                 200                 205

Thr Ser Val Phe Ala Arg Cys His Pro Leu Val Asp Pro Glu Pro Phe
    210                 215                 220

Val Ala Leu Cys Glu Lys Thr Leu Cys Glu Cys Ala Gly Gly Leu Glu
225                 230                 235                 240

Cys Ala Cys Pro Ala Leu Leu Glu Tyr Ala Arg Thr Cys Ala Gln Glu
                245                 250                 255

Gly Met Val Leu Tyr Gly Trp Thr Asp His Ser Ala Cys Ser Pro Val
            260                 265                 270

Cys Pro Ala Gly Met Glu Tyr Arg Gln Cys Val Ser Pro Cys Ala Arg
            275                 280                 285

Thr Cys Gln Ser Leu His Ile Asn Glu Met Cys Gln Glu Arg Cys Val
    290                 295                 300

Asp Gly Cys Ser Cys Pro Glu Gly Gln Leu Leu Asp Glu Gly Leu Cys
305                 310                 315                 320

Val Glu Ser Thr Glu Cys Pro Cys Val His Ser Gly Lys Arg Tyr Pro
                325                 330                 335

Pro Gly Thr Ser Leu Ser Arg Asp Cys Asn Thr Cys Ile Cys Arg Asn
            340                 345                 350

Ser Gln Trp Ile Cys Ser Asn Glu Glu Cys Pro Gly Glu Cys Leu Val
            355                 360                 365

Thr Gly Gln Ser His Phe Lys Ser Phe Asp Asn Arg Tyr Phe Thr Phe
    370                 375                 380

Ser Gly Ile Cys Gln Tyr Leu Leu Ala Arg Asp Cys Gln Asp His Ser
385                 390                 395                 400

Phe Ser Ile Val Ile Glu Thr Val Gln Cys Ala Asp Asp Arg Asp Ala
                405                 410                 415

Val Cys Thr Arg Ser Val Thr Val Arg Leu Pro Gly Leu His Asn Ser
            420                 425                 430

Leu Val Lys Leu Lys His Gly Ala Gly Val Ala Met Asp Gly Gln Asp
            435                 440                 445
```

-continued

```
Ile Gln Leu Pro Leu Leu Lys Gly Asp Leu Arg Ile Gln His Thr Val
    450                 455                 460
Thr Ala Ser Val Arg Leu Ser Tyr Gly Glu Asp Leu Gln Met Asp Trp
465                 470                 475                 480
Asp Gly Arg Gly Arg Leu Leu Val Lys Leu Ser Pro Val Tyr Ala Gly
                485                 490                 495
Lys Thr Cys Gly Leu Cys Gly Asn Tyr Asn Gly Asn Gln Gly Asp Asp
            500                 505                 510
Phe Leu Thr Pro Ser Gly Leu Ala Glu Pro Arg Val Glu Asp Phe Gly
        515                 520                 525
Asn Ala Trp Lys Leu His Gly Asp Cys Gln Asp Leu Gln Lys Gln His
530                 535                 540
Ser Asp Pro Cys Ala Leu Asn Pro Arg Met Thr Arg Phe Ser Glu Glu
545                 550                 555                 560
Ala Cys Ala Val Leu Thr Ser Pro Thr Phe Glu Ala Cys His Arg Ala
                565                 570                 575
Val Ser Pro Leu Pro Tyr Leu Arg Asn Cys Arg Tyr Asp Val Cys Ser
                580                 585                 590
Cys Ser Asp Gly Arg Glu Cys Leu Cys Gly Ala Leu Ala Ser Tyr Ala
        595                 600                 605
Ala Ala Cys Ala Gly Arg Gly Val Arg Val Ala Trp Arg Glu Pro Gly
    610                 615                 620
Arg Cys Glu Leu Asn Cys Pro Lys Gly Gln Val Tyr Leu Gln Cys Gly
625                 630                 635                 640
Thr Pro Cys Asn Leu Thr Cys Arg Ser Leu Ser Tyr Pro Asp Glu Glu
                645                 650                 655
Cys Asn Glu Ala Cys Leu Glu Gly Cys Phe Cys Pro Pro Gly Leu Tyr
                660                 665                 670
Met Asp Glu Arg Gly Asp Cys Val Pro Lys Ala Gln Cys Pro Cys Tyr
        675                 680                 685
Tyr Asp Gly Glu Ile Phe Gln Pro Glu Asp Ile Phe Ser Asp His His
    690                 695                 700
Thr Met Cys Tyr Cys Glu Asp Gly Phe Met His Cys Thr Met Ser Gly
705                 710                 715                 720
Val Pro Gly Ser Leu Leu Pro Asp Ala Val Leu Ser Ser Pro Leu Ser
                725                 730                 735
His Arg Ser Lys Arg
            740

<210> SEQ ID NO 7
<211> LENGTH: 101
<212> TYPE: PRT
<213> ORGANISM: Artificial Sequence
<220> FEATURE:
<223> OTHER INFORMATION: Synthetic construct

<400> SEQUENCE: 7

Ser Leu Ser Cys Arg Pro Met Val Lys Leu Val Cys Pro Ala Asp
1               5                   10                  15
Asn Leu Arg Ala Glu Gly Leu Glu Cys Thr Lys Thr Cys Gln Asn Tyr
                20                  25                  30
Asp Leu Glu Cys Met Ser Met Gly Cys Val Ser Gly Cys Leu Cys Pro
            35                  40                  45
Pro Gly Met Val Arg His Glu Asn Arg Cys Val Ala Leu Glu Arg Cys
        50                  55                  60
```

```
Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp
            100

<210> SEQ ID NO 8
<211> LENGTH: 406
<212> TYPE: PRT
<213> ORGANISM: Artificial Sequence
<220> FEATURE:
<223> OTHER INFORMATION: Synthetic construct

<400> SEQUENCE: 8

Ala Thr Cys Ser Thr Ile Gly Met Ala His Tyr Leu Thr Phe Asp Gly
1               5                   10                  15

Leu Lys Tyr Leu Phe Pro Gly Glu Cys Gln Tyr Val Leu Val Gln Asp
                20                  25                  30

Tyr Cys Gly Ser Asn Pro Gly Thr Phe Arg Ile Leu Val Gly Asn Lys
            35                  40                  45

Gly Cys Ser His Pro Ser Val Lys Cys Lys Lys Arg Val Thr Ile Leu
50                  55                  60

Val Glu Gly Gly Glu Ile Glu Leu Phe Asp Gly Glu Val Asn Val Lys
65                  70                  75                  80

Arg Pro Met Lys Asp Glu Thr His Phe Glu Val Val Glu Ser Gly Arg
                85                  90                  95

Tyr Ile Ile Leu Leu Leu Gly Lys Ala Leu Ser Val Val Trp Asp Arg
            100                 105                 110

His Leu Ser Ile Ser Val Val Leu Lys Gln Thr Tyr Gln Glu Lys Val
        115                 120                 125

Cys Gly Leu Cys Gly Asn Phe Asp Gly Ile Gln Asn Asn Asp Leu Thr
130                 135                 140

Ser Ser Asn Leu Gln Val Glu Glu Asp Pro Val Asp Phe Gly Asn Ser
145                 150                 155                 160

Trp Lys Val Ser Ser Gln Cys Ala Asp Thr Arg Lys Val Pro Leu Asp
                165                 170                 175

Ser Ser Pro Ala Thr Cys His Asn Asn Ile Met Lys Gln Thr Met Val
            180                 185                 190

Asp Ser Ser Cys Arg Ile Leu Thr Ser Asp Val Phe Gln Asp Cys Asn
        195                 200                 205

Lys Leu Val Asp Pro Glu Pro Tyr Leu Asp Val Cys Ile Tyr Asp Thr
210                 215                 220

Cys Ser Cys Glu Ser Ile Gly Asp Cys Ala Cys Phe Cys Asp Thr Ile
225                 230                 235                 240

Ala Ala Tyr Ala His Val Cys Ala Gln His Gly Lys Val Val Thr Trp
                245                 250                 255

Arg Thr Ala Thr Leu Cys Pro Gln Ser Cys Glu Glu Arg Asn Leu Arg
            260                 265                 270

Glu Asn Gly Tyr Glu Cys Glu Trp Arg Tyr Asn Ser Cys Ala Pro Ala
        275                 280                 285

Cys Gln Val Thr Cys Gln His Pro Glu Pro Leu Ala Cys Pro Val Gln
290                 295                 300

Cys Val Glu Gly Cys His Ala His Cys Pro Pro Gly Lys Ile Leu Asp
305                 310                 315                 320
```

```
Glu Leu Leu Gln Thr Cys Val Asp Pro Glu Asp Cys Pro Val Cys Glu
                325                 330                 335

Val Ala Gly Arg Arg Phe Ala Ser Gly Lys Lys Val Thr Leu Asn Pro
            340                 345                 350

Ser Asp Pro Glu His Cys Gln Ile Cys His Cys Asp Val Val Asn Leu
        355                 360                 365

Thr Cys Glu Ala Cys Gln Pro Gly Gly Leu Val Val Pro Pro Thr
370                 375                 380

Asp Ala Pro Val Ser Pro Thr Thr Leu Tyr Val Glu Asp Ile Ser Glu
385                 390                 395                 400

Pro Pro Leu His Asp Phe
            405

<210> SEQ ID NO 9
<211> LENGTH: 183
<212> TYPE: PRT
<213> ORGANISM: Artificial Sequence
<220> FEATURE:
<223> OTHER INFORMATION: Synthetic construct

<400> SEQUENCE: 9

Tyr Cys Ser Arg Leu Leu Asp Leu Val Phe Leu Leu Asp Gly Ser Ser
1               5                   10                  15

Arg Leu Ser Glu Ala Glu Phe Glu Val Leu Lys Ala Phe Val Val Asp
            20                  25                  30

Met Met Glu Arg Leu Arg Ile Ser Gln Lys Trp Val Arg Val Ala Val
        35                  40                  45

Val Glu Tyr His Asp Gly Ser His Ala Tyr Ile Gly Leu Lys Asp Arg
    50                  55                  60

Lys Arg Pro Ser Glu Leu Arg Arg Ile Ala Ser Gln Val Lys Tyr Ala
65                  70                  75                  80

Gly Ser Gln Val Ala Ser Thr Ser Glu Val Leu Lys Tyr Thr Leu Phe
                85                  90                  95

Gln Ile Phe Ser Lys Ile Asp Arg Pro Glu Ala Ser Arg Ile Ala Leu
            100                 105                 110

Leu Leu Met Ala Ser Gln Glu Pro Gln Arg Met Ser Arg Asn Phe Val
        115                 120                 125

Arg Tyr Val Gln Gly Leu Lys Lys Lys Lys Val Ile Val Ile Pro Val
    130                 135                 140

Gly Ile Gly Pro His Ala Asn Leu Lys Gln Ile Arg Leu Ile Glu Lys
145                 150                 155                 160

Gln Ala Pro Glu Asn Lys Ala Phe Val Leu Ser Ser Val Asp Glu Leu
                165                 170                 175

Glu Gln Gln Arg Asp Glu Ile
            180

<210> SEQ ID NO 10
<211> LENGTH: 44
<212> TYPE: PRT
<213> ORGANISM: Artificial Sequence
<220> FEATURE:
<223> OTHER INFORMATION: Synthetic construct

<400> SEQUENCE: 10

Val Ser Tyr Leu Cys Asp Leu Ala Pro Glu Ala Pro Pro Pro Thr Leu
1               5                   10                  15

Pro Pro His Met Ala Gln Val Thr Val Gly Pro Gly Leu Leu Gly Val
            20                  25                  30
```

Ser Thr Leu Gly Pro Lys Arg Asn Ser Met Val Leu
        35                  40

<210> SEQ ID NO 11
<211> LENGTH: 173
<212> TYPE: PRT
<213> ORGANISM: Artificial Sequence
<220> FEATURE:
<223> OTHER INFORMATION: Synthetic construct

<400> SEQUENCE: 11

Asp Val Ala Phe Val Leu Glu Gly Ser Asp Lys Ile Gly Glu Ala Asp
1               5                   10                  15

Phe Asn Arg Ser Lys Glu Phe Met Glu Val Ile Gln Arg Met Asp
            20                  25                  30

Val Gly Gln Asp Ser Ile His Val Thr Val Leu Gln Tyr Ser Tyr Met
        35                  40                  45

Val Thr Val Glu Tyr Pro Phe Ser Glu Ala Gln Ser Lys Gly Asp Ile
    50                  55                  60

Leu Gln Arg Val Arg Glu Ile Arg Tyr Gln Gly Gly Asn Arg Thr Asn
65                  70                  75                  80

Thr Gly Leu Ala Leu Arg Tyr Leu Ser Asp His Ser Phe Leu Val Ser
                85                  90                  95

Gln Gly Asp Arg Glu Gln Ala Pro Asn Leu Val Tyr Met Val Thr Gly
            100                 105                 110

Asn Pro Ala Ser Asp Glu Ile Lys Arg Leu Pro Gly Asp Ile Gln Val
        115                 120                 125

Val Pro Ile Gly Val Gly Pro Asn Ala Asn Val Gln Glu Leu Glu Arg
    130                 135                 140

Ile Gly Trp Pro Asn Ala Pro Ile Leu Ile Gln Asp Phe Glu Thr Leu
145                 150                 155                 160

Pro Arg Glu Ala Pro Asp Leu Val Leu Gln Arg Cys Cys
                165                 170

<210> SEQ ID NO 12
<211> LENGTH: 204
<212> TYPE: PRT
<213> ORGANISM: Artificial Sequence
<220> FEATURE:
<223> OTHER INFORMATION: Synthetic construct

<400> SEQUENCE: 12

Ser Gly Glu Gly Leu Gln Ile Pro Thr Leu Ser Pro Ala Pro Asp Cys
1               5                   10                  15

Ser Gln Pro Leu Asp Val Ile Leu Leu Leu Asp Gly Ser Ser Ser Phe
            20                  25                  30

Pro Ala Ser Tyr Phe Asp Glu Met Lys Ser Phe Ala Lys Ala Phe Ile
        35                  40                  45

Ser Lys Ala Asn Ile Gly Pro Arg Leu Thr Gln Val Ser Val Leu Gln
    50                  55                  60

Tyr Gly Ser Ile Thr Thr Ile Asp Val Pro Trp Asn Val Val Pro Glu
65                  70                  75                  80

Lys Ala His Leu Leu Ser Leu Val Asp Val Met Gln Arg Glu Gly Gly
                85                  90                  95

Pro Ser Gln Ile Gly Asp Ala Leu Gly Phe Ala Val Arg Tyr Leu Thr
            100                 105                 110

Ser Glu Met His Gly Ala Arg Pro Gly Ala Ser Lys Ala Val Val Ile

```
                115                 120                 125
Leu Val Thr Asp Val Ser Val Asp Ser Val Asp Ala Ala Asp Ala
            130                 135                 140

Ala Arg Ser Asn Arg Val Thr Val Phe Pro Ile Gly Ile Gly Asp Arg
145                 150                 155                 160

Tyr Asp Ala Ala Gln Leu Arg Ile Leu Ala Gly Pro Ala Gly Asp Ser
                165                 170                 175

Asn Val Val Lys Leu Gln Arg Ile Glu Asp Leu Pro Thr Met Val Thr
            180                 185                 190

Leu Gly Asn Ser Phe Leu His Lys Leu Cys Ser Gly
            195                 200

<210> SEQ ID NO 13
<211> LENGTH: 380
<212> TYPE: PRT
<213> ORGANISM: Artificial Sequence
<220> FEATURE:
<223> OTHER INFORMATION: Synthetic construct

<400> SEQUENCE: 13

Phe Val Arg Ile Cys Met Asp Glu Asp Gly Asn Glu Lys Arg Pro Gly
1               5                   10                  15

Asp Val Trp Thr Leu Pro Asp Gln Cys His Thr Val Thr Cys Gln Pro
            20                  25                  30

Asp Gly Gln Thr Leu Leu Lys Ser His Arg Val Asn Cys Asp Arg Gly
        35                  40                  45

Leu Arg Pro Ser Cys Pro Asn Ser Gln Ser Pro Val Lys Val Glu Glu
50                  55                  60

Thr Cys Gly Cys Arg Trp Thr Cys Pro Val Cys Thr Gly Ser Ser
65                  70                  75                  80

Thr Arg His Ile Val Thr Phe Asp Gly Gln Asn Phe Lys Leu Thr Gly
                85                  90                  95

Ser Cys Ser Tyr Val Leu Phe Gln Asn Lys Glu Gln Asp Leu Glu Val
            100                 105                 110

Ile Leu His Asn Gly Ala Cys Ser Pro Gly Ala Arg Gln Gly Cys Met
            115                 120                 125

Lys Ser Ile Glu Val Lys His Ser Ala Leu Ser Val Glu Leu His Ser
130                 135                 140

Asp Met Glu Val Thr Val Asn Gly Arg Leu Val Ser Val Pro Tyr Val
145                 150                 155                 160

Gly Gly Asn Met Glu Val Asn Val Tyr Gly Ala Ile Met His Glu Val
                165                 170                 175

Arg Phe Asn His Leu Gly His Ile Phe Thr Phe Thr Pro Gln Asn Asn
            180                 185                 190

Glu Phe Gln Leu Gln Leu Ser Pro Lys Thr Phe Ala Ser Lys Thr Tyr
        195                 200                 205

Gly Leu Cys Gly Ile Cys Asp Glu Asn Gly Ala Asn Asp Phe Met Leu
    210                 215                 220

Arg Asp Gly Thr Val Thr Thr Asp Trp Lys Thr Leu Val Gln Glu Trp
225                 230                 235                 240

Thr Val Gln Arg Pro Gly Gln Thr Cys Gln Pro Ile Leu Glu Glu Gln
                245                 250                 255

Cys Leu Val Pro Asp Ser Ser His Cys Gln Val Leu Leu Leu Pro Leu
            260                 265                 270

Phe Ala Glu Cys His Lys Val Leu Ala Pro Ala Thr Phe Tyr Ala Ile
```

```
            275                 280                 285
Cys Gln Gln Asp Ser Cys His Gln Glu Gln Val Cys Glu Val Ile Ala
        290                 295                 300
Ser Tyr Ala His Leu Cys Arg Thr Asn Gly Val Cys Val Asp Trp Arg
305                 310                 315                 320
Thr Pro Asp Phe Cys Ala Met Ser Cys Pro Pro Ser Leu Val Tyr Asn
                325                 330                 335
His Cys Glu His Gly Cys Pro Arg His Cys Asp Gly Asn Val Ser Ser
            340                 345                 350
Cys Gly Asp His Pro Ser Glu Gly Cys Phe Cys Pro Pro Asp Lys Val
        355                 360                 365
Met Leu Glu Gly Ser Cys Val Pro Glu Glu Ala Cys
370                 375                 380

<210> SEQ ID NO 14
<211> LENGTH: 79
<212> TYPE: PRT
<213> ORGANISM: Artificial Sequence
<220> FEATURE:
<223> OTHER INFORMATION: Synthetic construct

<400> SEQUENCE: 14

Thr Gln Cys Ile Gly Glu Asp Gly Val Gln His Gln Phe Leu Glu Ala
1               5                   10                  15
Trp Val Pro Asp His Gln Pro Cys Gln Ile Cys Thr Cys Leu Ser Gly
                20                  25                  30
Arg Lys Val Asn Cys Thr Thr Gln Pro Cys Pro Thr Ala Lys Ala Pro
            35                  40                  45
Thr Cys Gly Leu Cys Glu Val Ala Arg Leu Arg Gln Asn Ala Asp Gln
    50                  55                  60
Cys Cys Pro Glu Tyr Glu Cys Val Cys Asp Pro Val Ser Cys Asp
65                  70                  75

<210> SEQ ID NO 15
<211> LENGTH: 69
<212> TYPE: PRT
<213> ORGANISM: Artificial Sequence
<220> FEATURE:
<223> OTHER INFORMATION: Synthetic construct

<400> SEQUENCE: 15

Leu Pro Pro Val Pro His Cys Glu Arg Gly Leu Gln Pro Thr Leu Thr
1               5                   10                  15
Asn Pro Gly Glu Cys Arg Pro Asn Phe Thr Cys Ala Cys Arg Lys Glu
                20                  25                  30
Glu Cys Lys Arg Val Ser Pro Pro Ser Cys Pro Pro His Arg Leu Pro
            35                  40                  45
Thr Leu Arg Lys Thr Gln Cys Cys Asp Glu Tyr Glu Cys Ala Cys Asn
    50                  55                  60
Cys Val Asn Ser Thr
65

<210> SEQ ID NO 16
<211> LENGTH: 26
<212> TYPE: PRT
<213> ORGANISM: Artificial Sequence
<220> FEATURE:
<223> OTHER INFORMATION: Synthetic construct

<400> SEQUENCE: 16
```

```
Val Ser Cys Pro Leu Gly Tyr Leu Ala Ser Thr Ala Thr Asn Asp Cys
1               5                   10                  15

Gly Cys Thr Thr Thr Thr Cys Leu Pro Asp
            20              25
```

<210> SEQ ID NO 17
<211> LENGTH: 68
<212> TYPE: PRT
<213> ORGANISM: Artificial Sequence
<220> FEATURE:
<223> OTHER INFORMATION: Synthetic construct

<400> SEQUENCE: 17

```
Lys Val Cys Val His Arg Ser Thr Ile Tyr Pro Val Gly Gln Phe Trp
1               5                   10                  15

Glu Glu Gly Cys Asp Val Cys Thr Cys Thr Asp Met Glu Asp Ala Val
                20                  25                  30

Met Gly Leu Arg Val Ala Gln Cys Ser Gln Lys Pro Cys Glu Asp Ser
            35                  40                  45

Cys Arg Ser Gly Phe Thr Tyr Val Leu His Glu Gly Glu Cys Cys Gly
    50                  55                  60

Arg Cys Leu Pro
65
```

<210> SEQ ID NO 18
<211> LENGTH: 81
<212> TYPE: PRT
<213> ORGANISM: Artificial Sequence
<220> FEATURE:
<223> OTHER INFORMATION: Synthetic construct

<400> SEQUENCE: 18

```
Ser Ala Cys Glu Val Val Thr Gly Ser Pro Arg Gly Asp Ser Gln Ser
1               5                   10                  15

Ser Trp Lys Ser Val Gly Ser Gln Trp Ala Ser Pro Glu Asn Pro Cys
                20                  25                  30

Leu Ile Asn Glu Cys Val Arg Val Lys Glu Glu Val Phe Ile Gln Gln
            35                  40                  45

Arg Asn Val Ser Cys Pro Gln Leu Glu Val Pro Val Cys Pro Ser Gly
    50                  55                  60

Phe Gln Leu Ser Cys Lys Thr Ser Ala Cys Cys Pro Ser Cys Arg Cys
65                  70                  75                  80

Glu
```

<210> SEQ ID NO 19
<211> LENGTH: 69
<212> TYPE: PRT
<213> ORGANISM: Artificial Sequence
<220> FEATURE:
<223> OTHER INFORMATION: Synthetic construct

<400> SEQUENCE: 19

```
Arg Met Glu Ala Cys Met Leu Asn Gly Thr Val Ile Gly Pro Gly Lys
1               5                   10                  15

Thr Val Met Ile Asp Val Cys Thr Thr Cys Arg Cys Met Val Gln Val
                20                  25                  30

Gly Val Ile Ser Gly Phe Lys Leu Glu Cys Arg Lys Thr Thr Cys Asn
            35                  40                  45

Pro Cys Pro Leu Gly Tyr Lys Glu Glu Asn Asn Thr Gly Glu Cys Cys
```

Gly Arg Cys Leu Pro
65

<210> SEQ ID NO 20
<211> LENGTH: 74
<212> TYPE: PRT
<213> ORGANISM: Artificial Sequence
<220> FEATURE:
<223> OTHER INFORMATION: Synthetic construct

<400> SEQUENCE: 20

Thr Ala Cys Thr Ile Gln Leu Arg Gly Gly Gln Ile Met Thr Leu Lys
1               5                   10                  15

Arg Asp Glu Thr Leu Gln Asp Gly Cys Asp Thr His Phe Cys Lys Val
            20                  25                  30

Asn Glu Arg Gly Glu Tyr Phe Trp Glu Lys Arg Val Thr Gly Cys Pro
        35                  40                  45

Pro Phe Asp Glu His Lys Cys Leu Ala Glu Gly Gly Lys Ile Met Lys
    50                  55                  60

Ile Pro Gly Thr Cys Cys Asp Thr Cys Glu
65                  70

<210> SEQ ID NO 21
<211> LENGTH: 93
<212> TYPE: PRT
<213> ORGANISM: Artificial Sequence
<220> FEATURE:
<223> OTHER INFORMATION: Synthetic construct

<400> SEQUENCE: 21

Glu Pro Glu Cys Asn Asp Ile Thr Ala Arg Leu Gln Tyr Val Lys Val
1               5                   10                  15

Gly Ser Cys Lys Ser Glu Val Glu Val Asp Ile His Tyr Cys Gln Gly
            20                  25                  30

Lys Cys Ala Ser Lys Ala Met Tyr Ser Ile Asp Ile Asn Asp Val Gln
        35                  40                  45

Asp Gln Cys Ser Cys Cys Ser Pro Thr Arg Thr Glu Pro Met Gln Val
    50                  55                  60

Ala Leu His Cys Thr Asn Gly Ser Val Val Tyr His Glu Val Leu Asn
65                  70                  75                  80

Ala Met Glu Cys Lys Cys Ser Pro Arg Lys Cys Ser Lys
                85                  90

<210> SEQ ID NO 22
<211> LENGTH: 2538
<212> TYPE: DNA
<213> ORGANISM: Artificial Sequence
<220> FEATURE:
<223> OTHER INFORMATION: Synthetic construct

<400> SEQUENCE: 22
tttgttagga tttgcatgga tgaggatggg aatgagaaga ggcccgggga cgtctggacc      60
ttgccagacc agtgccacac cgtgacttgc cagccagatg ccagaccttt gctgaagagt     120
catcgggtca actgtgaccg ggggctgagg ccttcgtgcc ctaacagcca gtcccctgtt     180
aaagtggaag agacctgtgg ctgccgctgg acctgcccct gcgtgtgcac aggcagctcc     240
actcggcaca tcgtgacctt tgatgggcag aatttcaagc tgactggcag ctgttcttat     300
gtcctatttc aaaacaagga gcaggacctg gaggtgattc tccataatgg tgcctgcagc     360

```
cctggagcaa ggcagggctg catgaaatcc atcgaggtga agcacagtgc cctctccgtc    420
gagctgcaca gtgacatgga ggtgacgtg aatgggagac tggtctctgt tccttacgtg     480
ggtgggaaca tggaagtcaa cgtttatggt gccatcatgc atgaggtcag attcaatcac    540
cttggtcaca tcttcacatt cactccacaa aacaatgagt tccaactgca gctcagcccc    600 aagactttg cttcaaagac gtatggtctg tgtgggatct gtgatgagaa cggagccaat     660
gacttcatgc tgagggatgg cacagtcacc acagactgga aaacacttgt tcaggaatgg    720
actgtgcagc ggccagggca gacgtgccag cccatcctgg aggagcagtg tcttgtcccc    780
gacagctccc actgccaggt cctcctctta ccactgtttg ctgaatgcca aaggtcctg     840 gctccagcca cattctatgc catctgccag caggacagtt gccaccagga gcaagtgtgt    900
gaggtgatcg cctcttatgc ccacctctgt cggaccaacg ggtctgcgt tgactggagg     960 acacctgatt tctgtgctat gtcatgccca ccatctctgg tctacaacca ctgtgagcat    1020
ggctgtcccc ggcactgtga tggcaacgtg agctcctgtg ggaccatcc ctccgaaggc     1080 tgtttctgcc ctccagataa agtcatgttg gaaggcagct gtgtccctga gaggcctgc     1140 actcagtgca ttggtgagga tggagtccag caccagttcc tggaagcctg ggtcccggac    1200
caccagccct gtcagatctg cacatgcctc agcgggcgga aggtcaactg cacaacgcag    1260 ccctgccca cggccaaagc tcccacgtgt ggcctgtgtg aagtagcccg cctccgccag     1320
aatgcagacc agtgctgccc cgagtatgag tgtgtgtgtg acccagtgag ctgtgacctg    1380
cccccagtgc ctcactgtga acgtggcctc cagcccacac tgaccaaccc tggcgagtgc    1440
agacccaact tcacctgcgc ctgcaggaag gaggagtgca aaagagtgtc cccacccctcc   1500 tgcccccgc accgtttgcc caccttcgg aagacccagt gctgtgatga gtatgagtgt     1560
gcctgcaact gtgtcaactc cacagtgagc tgtcccttg ggtacttggc ctcaaccgcc    1620
accaatgact gtggctgtac cacaaccacc tgccttcccg acaaggtgtg tgtccaccga    1680
agcaccatct accctgtggg ccagttctgg gaggagggct gcgatgtgtg cacctgcacc    1740
gacatggagg atgccgtgat gggcctccgc gtgcccagt gctcccagaa gccctgtgag    1800
gacagctgtc ggtcgggctt cacttacgtt ctgcatgaag gcgagtgctg tggaaggtgc    1860
ctgccatctg cctgtgaggt ggtgactggc tcaccgcggg gggactccca gtcttcctgg    1920
aagagtgtcg gctcccagtg ggcctccccg gagaaccct gcctcatcaa tgagtgtgtc    1980
cgagtgaagg aggaggtctt tatacaacaa aggaacgtct cctgcccccca gctggaggtc    2040 cctgtctgcc cctcgggctt tcagctgagc tgtaagacct cagcgtgctg cccaagctgt    2100
cgctgtgagc gcatggaggc ctgcatgctc aatggcactg tcattgggcc cgggaagact    2160
gtgatgatcg atgtgtgcac gacctgccgc tgcatggtgc aggtggggt catctctgga    2220 ttcaagctgg agtgcaggaa gaccacctgc aacccctgcc ccctgggtta caaggaagaa    2280
aataacacag gtgaatgttg tgggagatgt ttgcctacgg cttgcaccat tcagctaaga    2340
ggaggacaga tcatgacact gaagcgtgat gagacgctcc aggatggctg tgatactcac    2400
ttctgcaagg tcaatgagag aggagagtac ttctgggaga gagggtcac aggctgccca    2460 ccctttgatg aacacaagtg tctggctgag ggaggtaaaa ttatgaaaat tccaggcacc    2520
tgctgtgaca catgtgag                                                 2538
```

<210> SEQ ID NO 23
<211> LENGTH: 22
<212> TYPE: PRT

```
<213> ORGANISM: Artificial Sequence
<220> FEATURE:
<223> OTHER INFORMATION: Synthetic construct

<400> SEQUENCE: 23

Met Ile Pro Ala Arg Phe Ala Gly Val Leu Leu Ala Leu Ala Leu Ile
1               5                   10                  15

Leu Pro Gly Thr Leu Cys
            20

<210> SEQ ID NO 24
<211> LENGTH: 741
<212> TYPE: PRT
<213> ORGANISM: Artificial Sequence
<220> FEATURE:
<223> OTHER INFORMATION: Synthetic construct

<400> SEQUENCE: 24

Ala Glu Gly Thr Arg Gly Arg Ser Ser Thr Ala Arg Cys Ser Leu Phe
1               5                   10                  15

Gly Ser Asp Phe Val Asn Thr Phe Asp Gly Ser Met Tyr Ser Phe Ala
            20                  25                  30

Gly Tyr Cys Ser Tyr Leu Leu Ala Gly Gly Cys Gln Lys Arg Ser Phe
        35                  40                  45

Ser Ile Ile Gly Asp Phe Gln Asn Gly Lys Arg Val Ser Leu Ser Val
    50                  55                  60

Tyr Leu Gly Glu Phe Phe Asp Ile His Leu Phe Val Asn Gly Thr Val
65                  70                  75                  80

Thr Gln Gly Asp Gln Arg Val Ser Met Pro Tyr Ala Ser Lys Gly Leu
                85                  90                  95

Tyr Leu Glu Thr Glu Ala Gly Tyr Tyr Lys Leu Ser Gly Glu Ala Tyr
            100                 105                 110

Gly Phe Val Ala Arg Ile Asp Gly Ser Gly Asn Phe Gln Val Leu Leu
        115                 120                 125

Ser Asp Arg Tyr Phe Asn Lys Thr Cys Gly Leu Cys Gly Asn Phe Asn
    130                 135                 140

Ile Phe Ala Glu Asp Asp Phe Met Thr Gln Glu Gly Thr Leu Thr Ser
145                 150                 155                 160

Asp Pro Tyr Asp Phe Ala Asn Ser Trp Ala Leu Ser Ser Gly Glu Gln
                165                 170                 175

Trp Cys Glu Arg Ala Ser Pro Pro Ser Ser Ser Cys Asn Ile Ser Ser
            180                 185                 190

Gly Glu Met Gln Lys Gly Leu Trp Glu Gln Cys Gln Leu Leu Lys Ser
        195                 200                 205

Thr Ser Val Phe Ala Arg Cys His Pro Leu Val Asp Pro Glu Pro Phe
    210                 215                 220

Val Ala Leu Cys Glu Lys Thr Leu Cys Glu Cys Ala Gly Gly Leu Glu
225                 230                 235                 240

Cys Ala Cys Pro Ala Leu Leu Glu Tyr Ala Arg Thr Cys Ala Gln Glu
                245                 250                 255

Gly Met Val Leu Tyr Gly Trp Thr Asp His Ser Ala Cys Ser Pro Val
            260                 265                 270

Cys Pro Ala Gly Met Glu Tyr Arg Gln Cys Val Ser Pro Cys Ala Arg
        275                 280                 285

Thr Cys Gln Ser Leu His Ile Asn Glu Met Cys Gln Glu Arg Cys Val
    290                 295                 300
```

```
Asp Gly Cys Ser Cys Pro Glu Gly Gln Leu Leu Asp Glu Gly Leu Cys
305                 310                 315                 320

Val Glu Ser Thr Glu Cys Pro Cys Val His Ser Gly Lys Arg Tyr Pro
            325                 330                 335

Pro Gly Thr Ser Leu Ser Arg Asp Cys Asn Thr Cys Ile Cys Arg Asn
        340                 345                 350

Ser Gln Trp Ile Cys Ser Asn Glu Glu Cys Pro Gly Glu Cys Leu Val
    355                 360                 365

Thr Gly Gln Ser His Phe Lys Ser Phe Asp Asn Arg Tyr Phe Thr Phe
370                 375                 380

Ser Gly Ile Cys Gln Tyr Leu Leu Ala Arg Asp Cys Gln Asp His Ser
385                 390                 395                 400

Phe Ser Ile Val Ile Glu Thr Val Gln Cys Ala Asp Asp Arg Asp Ala
            405                 410                 415

Val Cys Thr Arg Ser Val Thr Val Arg Leu Pro Gly Leu His Asn Ser
            420                 425                 430

Leu Val Lys Leu Lys His Gly Ala Gly Val Ala Met Asp Gly Gln Asp
        435                 440                 445

Ile Gln Leu Pro Leu Leu Lys Gly Asp Leu Arg Ile Gln His Thr Val
    450                 455                 460

Thr Ala Ser Val Arg Leu Ser Tyr Gly Glu Asp Leu Gln Met Asp Trp
465                 470                 475                 480

Asp Gly Arg Gly Arg Leu Leu Val Lys Leu Ser Pro Val Tyr Ala Gly
                485                 490                 495

Lys Thr Cys Gly Leu Cys Gly Asn Tyr Asn Gly Asn Gln Gly Asp Asp
            500                 505                 510

Phe Leu Thr Pro Ser Gly Leu Ala Glu Pro Arg Val Glu Asp Phe Gly
    515                 520                 525

Asn Ala Trp Lys Leu His Gly Asp Cys Gln Asp Leu Gln Lys Gln His
530                 535                 540

Ser Asp Pro Cys Ala Leu Asn Pro Arg Met Thr Arg Phe Ser Glu Glu
545                 550                 555                 560

Ala Cys Ala Val Leu Thr Ser Pro Thr Phe Glu Ala Cys His Arg Ala
            565                 570                 575

Val Ser Pro Leu Pro Tyr Leu Arg Asn Cys Arg Tyr Asp Val Cys Ser
            580                 585                 590

Cys Ser Asp Gly Arg Glu Cys Leu Cys Gly Ala Leu Ala Ser Tyr Ala
        595                 600                 605

Ala Ala Cys Ala Gly Arg Gly Val Arg Val Ala Trp Arg Glu Pro Gly
610                 615                 620

Arg Cys Glu Leu Asn Cys Pro Lys Gly Gln Val Tyr Leu Gln Cys Gly
625                 630                 635                 640

Thr Pro Cys Asn Leu Thr Cys Arg Ser Leu Ser Tyr Pro Asp Glu Glu
            645                 650                 655

Cys Asn Glu Ala Cys Leu Glu Gly Cys Phe Cys Pro Pro Gly Leu Tyr
            660                 665                 670

Met Asp Glu Arg Gly Asp Cys Val Pro Lys Ala Gln Cys Pro Cys Tyr
        675                 680                 685

Tyr Asp Gly Glu Ile Phe Gln Pro Glu Asp Ile Phe Ser Asp His His
        690                 695                 700

Thr Met Cys Tyr Cys Glu Asp Gly Phe Met His Cys Thr Met Ser Gly
705                 710                 715                 720

Val Pro Gly Ser Leu Leu Pro Asp Ala Val Leu Ser Ser Pro Leu Ser
```

His Arg Ser Lys Arg
            740

<210> SEQ ID NO 25
<211> LENGTH: 101
<212> TYPE: PRT
<213> ORGANISM: Artificial Sequence
<220> FEATURE:
<223> OTHER INFORMATION: Synthetic construct

<400> SEQUENCE: 25

Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp
            100

<210> SEQ ID NO 26
<211> LENGTH: 406
<212> TYPE: PRT
<213> ORGANISM: Artificial Sequence
<220> FEATURE:
<223> OTHER INFORMATION: Synthetic construct

<400> SEQUENCE: 26

Ala Thr Cys Ser Thr Ile Gly Met Ala His Tyr Leu Thr Phe Asp Gly
1               5                   10                  15

Leu Lys Tyr Leu Phe Pro Gly Glu Cys Gln Tyr Val Leu Val Gln Asp
            20                  25                  30

Tyr Cys Gly Ser Asn Pro Gly Thr Phe Arg Ile Leu Val Gly Asn Lys
        35                  40                  45

Gly Cys Ser His Pro Ser Val Lys Cys Lys Lys Arg Val Thr Ile Leu
    50                  55                  60

Val Glu Gly Gly Glu Ile Glu Leu Phe Asp Gly Glu Val Asn Val Lys
65                  70                  75                  80

Arg Pro Met Lys Asp Glu Thr His Phe Glu Val Val Glu Ser Gly Arg
                85                  90                  95

Tyr Ile Ile Leu Leu Leu Gly Lys Ala Leu Ser Val Val Trp Asp Arg
            100                 105                 110

His Leu Ser Ile Ser Val Val Leu Lys Gln Thr Tyr Gln Glu Lys Val
        115                 120                 125

Cys Gly Leu Cys Gly Asn Phe Asp Gly Ile Gln Asn Asn Asp Leu Thr
    130                 135                 140

Ser Ser Asn Leu Gln Val Glu Glu Asp Pro Val Asp Phe Gly Asn Ser
145                 150                 155                 160

Trp Lys Val Ser Ser Gln Cys Ala Asp Thr Arg Lys Val Pro Leu Asp
                165                 170                 175

```
Ser Ser Pro Ala Thr Cys His Asn Asn Ile Met Lys Gln Thr Met Val
            180                 185                 190

Asp Ser Ser Cys Arg Ile Leu Thr Ser Asp Val Phe Gln Asp Cys Asn
            195                 200                 205

Lys Leu Val Asp Pro Glu Pro Tyr Leu Asp Val Cys Ile Tyr Asp Thr
            210                 215                 220

Cys Ser Cys Glu Ser Ile Gly Asp Cys Ala Cys Phe Cys Asp Thr Ile
225                 230                 235                 240

Ala Ala Tyr Ala His Val Cys Ala Gln His Gly Lys Val Val Thr Trp
            245                 250                 255

Arg Thr Ala Thr Leu Cys Pro Gln Ser Cys Glu Glu Arg Asn Leu Arg
            260                 265                 270

Glu Asn Gly Tyr Glu Cys Glu Trp Arg Tyr Asn Ser Cys Ala Pro Ala
            275                 280                 285

Cys Gln Val Thr Cys Gln His Pro Glu Pro Leu Ala Cys Pro Val Gln
            290                 295                 300

Cys Val Glu Gly Cys His Ala His Cys Pro Pro Gly Lys Ile Leu Asp
305                 310                 315                 320

Glu Leu Leu Gln Thr Cys Val Asp Pro Glu Asp Cys Pro Val Cys Glu
            325                 330                 335

Val Ala Gly Arg Arg Phe Ala Ser Gly Lys Lys Val Thr Leu Asn Pro
            340                 345                 350

Ser Asp Pro Glu His Cys Gln Ile Cys His Cys Asp Val Val Asn Leu
            355                 360                 365

Thr Cys Glu Ala Cys Gln Glu Pro Gly Gly Leu Val Val Pro Pro Thr
            370                 375                 380

Asp Ala Pro Val Ser Pro Thr Thr Leu Tyr Val Glu Asp Ile Ser Glu
385                 390                 395                 400

Pro Pro Leu His Asp Phe
            405

<210> SEQ ID NO 27
<211> LENGTH: 183
<212> TYPE: PRT
<213> ORGANISM: Artificial Sequence
<220> FEATURE:
<223> OTHER INFORMATION: Synthetic construct

<400> SEQUENCE: 27

Tyr Cys Ser Arg Leu Leu Asp Leu Val Phe Leu Leu Asp Gly Ser Ser
1               5                   10                  15

Arg Leu Ser Glu Ala Glu Phe Glu Val Leu Lys Ala Phe Val Val Asp
            20                  25                  30

Met Met Glu Arg Leu Arg Ile Ser Gln Lys Trp Val Arg Val Ala Val
            35                  40                  45

Val Glu Tyr His Asp Gly Ser His Ala Tyr Ile Gly Leu Lys Asp Arg
        50                  55                  60

Lys Arg Pro Ser Glu Leu Arg Arg Ile Ala Ser Gln Val Lys Tyr Ala
65                  70                  75                  80

Gly Ser Gln Val Ala Ser Thr Ser Glu Val Leu Lys Tyr Thr Leu Phe
            85                  90                  95

Gln Ile Phe Ser Lys Ile Asp Arg Pro Glu Ala Ser Arg Ile Ala Leu
            100                 105                 110

Leu Leu Met Ala Ser Gln Glu Pro Gln Arg Met Ser Arg Asn Phe Val
            115                 120                 125
```

```
Arg Tyr Val Gln Gly Leu Lys Lys Lys Val Ile Val Ile Pro Val
            130                 135                 140

Gly Ile Gly Pro His Ala Asn Leu Lys Gln Ile Arg Leu Ile Glu Lys
145                 150                 155                 160

Gln Ala Pro Glu Asn Lys Ala Phe Val Leu Ser Ser Val Asp Glu Leu
                165                 170                 175

Glu Gln Gln Arg Asp Glu Ile
            180

<210> SEQ ID NO 28
<211> LENGTH: 44
<212> TYPE: PRT
<213> ORGANISM: Artificial Sequence
<220> FEATURE:
<223> OTHER INFORMATION: Synthetic construct

<400> SEQUENCE: 28

Val Ser Tyr Leu Cys Asp Leu Ala Pro Glu Ala Pro Pro Thr Leu
1               5                   10                  15

Pro Pro His Met Ala Gln Val Thr Val Gly Pro Gly Leu Leu Gly Val
                20                  25                  30

Ser Thr Leu Gly Pro Lys Arg Asn Ser Met Val Leu
            35                  40

<210> SEQ ID NO 29
<211> LENGTH: 173
<212> TYPE: PRT
<213> ORGANISM: Artificial Sequence
<220> FEATURE:
<223> OTHER INFORMATION: Synthetic construct

<400> SEQUENCE: 29

Asp Val Ala Phe Val Leu Glu Gly Ser Asp Lys Ile Gly Glu Ala Asp
1               5                   10                  15

Phe Asn Arg Ser Lys Glu Phe Met Glu Glu Val Ile Gln Arg Met Asp
                20                  25                  30

Val Gly Gln Asp Ser Ile His Val Thr Val Leu Gln Tyr Ser Tyr Met
            35                  40                  45

Val Thr Val Glu Tyr Pro Phe Ser Glu Ala Gln Ser Lys Gly Asp Ile
50                  55                  60

Leu Gln Arg Val Arg Glu Ile Arg Tyr Gln Gly Gly Asn Arg Thr Asn
65                  70                  75                  80

Thr Gly Leu Ala Leu Arg Tyr Leu Ser Asp His Ser Phe Leu Val Ser
                85                  90                  95

Gln Gly Asp Arg Glu Gln Ala Pro Asn Leu Val Tyr Met Val Thr Gly
            100                 105                 110

Asn Pro Ala Ser Asp Glu Ile Lys Arg Leu Pro Gly Asp Ile Gln Val
            115                 120                 125

Val Pro Ile Gly Val Gly Pro Asn Ala Asn Val Gln Glu Leu Glu Arg
        130                 135                 140

Ile Gly Trp Pro Asn Ala Pro Ile Leu Ile Gln Asp Phe Glu Thr Leu
145                 150                 155                 160

Pro Arg Glu Ala Pro Asp Leu Val Leu Gln Arg Cys Cys
                165                 170

<210> SEQ ID NO 30
<211> LENGTH: 204
<212> TYPE: PRT
<213> ORGANISM: Artificial Sequence
```

```
<220> FEATURE:
<223> OTHER INFORMATION: Synthetic construct

<400> SEQUENCE: 30

Ser Gly Glu Gly Leu Gln Ile Pro Thr Leu Ser Pro Ala Pro Asp Cys
1               5                   10                  15

Ser Gln Pro Leu Asp Val Ile Leu Leu Leu Asp Gly Ser Ser Ser Phe
            20                  25                  30

Pro Ala Ser Tyr Phe Asp Glu Met Lys Ser Phe Ala Lys Ala Phe Ile
        35                  40                  45

Ser Lys Ala Asn Ile Gly Pro Arg Leu Thr Gln Val Ser Val Leu Gln
50                  55                  60

Tyr Gly Ser Ile Thr Thr Ile Asp Val Pro Trp Asn Val Val Pro Glu
65                  70                  75                  80

Lys Ala His Leu Leu Ser Leu Val Asp Val Met Gln Arg Glu Gly Gly
                85                  90                  95

Pro Ser Gln Ile Gly Asp Ala Leu Gly Phe Ala Val Arg Tyr Leu Thr
            100                 105                 110

Ser Glu Met His Gly Ala Arg Pro Gly Ala Ser Lys Ala Val Val Ile
        115                 120                 125

Leu Val Thr Asp Val Ser Val Asp Ser Val Asp Ala Ala Ala Asp Ala
130                 135                 140

Ala Arg Ser Asn Arg Val Thr Val Phe Pro Ile Gly Ile Gly Asp Arg
145                 150                 155                 160

Tyr Asp Ala Ala Gln Leu Arg Ile Leu Ala Gly Pro Ala Gly Asp Ser
                165                 170                 175

Asn Val Val Lys Leu Gln Arg Ile Glu Asp Leu Pro Thr Met Val Thr
            180                 185                 190

Leu Gly Asn Ser Phe Leu His Lys Leu Cys Ser Gly
        195                 200

<210> SEQ ID NO 31
<211> LENGTH: 93
<212> TYPE: PRT
<213> ORGANISM: Artificial Sequence
<220> FEATURE:
<223> OTHER INFORMATION: Synthetic construct

<400> SEQUENCE: 31

Glu Pro Glu Cys Asn Asp Ile Thr Ala Arg Leu Gln Tyr Val Lys Val
1               5                   10                  15

Gly Ser Cys Lys Ser Glu Val Val Asp Ile His Tyr Cys Gln Gly
            20                  25                  30

Lys Cys Ala Ser Lys Ala Met Tyr Ser Ile Asp Ile Asn Asp Val Gln
        35                  40                  45

Asp Gln Cys Ser Cys Cys Ser Pro Thr Arg Thr Glu Pro Met Gln Val
50                  55                  60

Ala Leu His Cys Thr Asn Gly Ser Val Val Tyr His Glu Val Leu Asn
65                  70                  75                  80

Ala Met Glu Cys Lys Cys Ser Pro Arg Lys Cys Ser Lys
                85                  90

<210> SEQ ID NO 32
<211> LENGTH: 4
<212> TYPE: PRT
<213> ORGANISM: Artificial Sequence
<220> FEATURE:
<223> OTHER INFORMATION: Synthetic construct
```

```
<400> SEQUENCE: 32

Arg Gly Asp Ser
1

<210> SEQ ID NO 33
<211> LENGTH: 4
<212> TYPE: PRT
<213> ORGANISM: Artificial Sequence
<220> FEATURE:
<223> OTHER INFORMATION: Synthetic construct

<400> SEQUENCE: 33

Arg Gly Gly Ser
1
```